(12) United States Patent
Hermon-Taylor

(10) Patent No.: US 12,186,382 B2
(45) Date of Patent: *Jan. 7, 2025

(54) IMMUNOGENIC COMPOSITION FOR PARATUBERCULOSIS

(71) Applicant: HAV VACCINES LIMITED, Milton Keynes (GB)

(72) Inventor: John Hermon-Taylor, London (GB)

(73) Assignee: HAV VACCINES LIMITED, Milton Keynes (GB)

( * ) Notice: Subject to any disclaimer, the term of this patent is extended or adjusted under 35 U.S.C. 154(b) by 943 days.

This patent is subject to a terminal disclaimer.

(21) Appl. No.: 17/259,075

(22) PCT Filed: Jul. 10, 2019

(86) PCT No.: PCT/GB2019/051933
§ 371 (c)(1),
(2) Date: Jan. 8, 2021

(87) PCT Pub. No.: WO2020/012177
PCT Pub. Date: Jan. 16, 2020

(65) Prior Publication Data
US 2021/0338791 A1 Nov. 4, 2021

(30) Foreign Application Priority Data

Jul. 11, 2018 (GB) .................................... 1811382

(51) Int. Cl.
| | |
|---|---|
| A61K 39/02 | (2006.01) |
| A61K 39/04 | (2006.01) |
| A61K 45/06 | (2006.01) |
| A61P 31/04 | (2006.01) |
| C07K 14/35 | (2006.01) |
| A61K 39/00 | (2006.01) |

(52) U.S. Cl.
CPC .............. *A61K 39/04* (2013.01); *A61K 45/06* (2013.01); *A61P 31/04* (2018.01); *C07K 14/35* (2013.01); *A61K 2039/5256* (2013.01)

(58) Field of Classification Search
None
See application file for complete search history.

(56) References Cited

U.S. PATENT DOCUMENTS

| | | | |
|---|---|---|---|
| 5,225,324 | A | 7/1993 | McFadden et al. |
| 6,156,322 | A | 12/2000 | Hermon-Taylor et al. |
| 7,541,181 | B2 | 6/2009 | Hermon-Taylor et al. |
| 7,867,704 | B2 * | 1/2011 | Kapur .................... C12Q 1/689 |
| | | | 435/6.15 |
| 7,892,566 | B2 | 2/2011 | Hermon-Taylor et al. |
| 8,147,850 | B2 | 4/2012 | Hermon-Taylor et al. |
| 11,714,085 | B2 * | 8/2023 | Hermon-Taylor ...... A61P 17/06 |
| | | | 424/139.1 |
| 2007/0042383 | A1 | 2/2007 | Kapur et al. |
| 2011/0129502 | A1 | 6/2011 | Hermon-Taylor et al. |

FOREIGN PATENT DOCUMENTS

| | | |
|---|---|---|
| EP | 0288306 | 10/1988 |
| WO | WO 88/08456 | 11/1988 |
| WO | WO 97/23624 | 7/1997 |
| WO | WO 99/49054 | 9/1999 |
| WO | WO 2007/017635 | 2/2007 |
| WO | WO 2010/142423 | 12/2010 |
| WO | WO 2011/013034 | 2/2011 |
| WO | WO 2012/159121 | 11/2012 |
| WO | WO 2014/016737 | 1/2014 |
| WO | WO 2014/114812 | 7/2014 |
| WO | WO 2018/130836 | 7/2018 |

OTHER PUBLICATIONS

Botsaris et al. "Detection of viable *Mycobacterium avium* subspecies *paratuberculosis* in powdered infant formula by phage-PCR and confirmed culture," International Journal of Food Microbiology, 2016, vol. 216, pp. 91-94.

Bull et al. "Detection and Verification of *Mycobacterium avium* subsp. *paratuberculosis* in Fresh Ileocolonic Mucosal Biopsy Specimens from Individuals with and without Crohn's Disease," Journal of Clinical Microbiology, Jul. 2003, vol. 41, No. 7, pp. 2915-2923.

Bull et al. "Immunity, safety and protection of an Adenovirus 5 prime—Modified Vaccinia virus Ankara boost subunit vaccine against *Mycobacterium avium* subspecies *paratuberculosis* infection in calves," Veterinary Research, 2014, vol. 45, 112, 17 pages.

Cucino et al. "The Comorbid Occurrence of Other Diagnoses in Patients With Ulcerative Colitis and Crohn's Disease," The American Journal of Gastroenterology, 2001, vol. 96, No. 7, pp. 2107-2112.

Fridy et al. "A robust pipeline for rapid production of versatile nanobody repertoires," Nature Methods, Dec. 2014, vol. 11, No. 12, pp. 1253-1260.

Green et al. "Sequence and characteristics of IS900, an insertion element identified in a human Crohn's disease isolate of *Mycobacterium paratuberculosis*," Nucleic Acids Research, 1989, vol. 17, No. 22, pp. 9063-9073.

Hartlova et al. "LRRK2 is a negative regulator of *Mycobacterium tuberculosis* phagosome maturation in macrophages," The EMBO Journal, 2018, vol. 37, article e98694, 17 pages.

Hermon-Taylor "*Mycobacterium avium* subspecies *paratuberculosis*, Crohn's disease and the Doomsday Scenario," Gut Pathogens, Feb. 2009, 1:15, 7 pages.

Hui et al. "Functional variants in the LRRK2 gene confer shared effects on risk for Crohn's disease and Parkinson's disease," Science Translational Medicine, Jan. 2018, vol. 10, eaai7795, 13 pages.

(Continued)

*Primary Examiner* — Jennifer E Graser
(74) *Attorney, Agent, or Firm* — Sheridan Ross P.C.

(57) ABSTRACT

A vaccine comprising a polypeptide comprising an amino acid sequence of at least 9 contiguous amino acids from the N-terminal region of MAP P900, or a polynucleotide encoding said polypeptide, for use in a method of treating or preventing MAP infection or a condition or symptom associated with MAP infection in a subject.

11 Claims, 9 Drawing Sheets

Specification includes a Sequence Listing.

(56) References Cited

OTHER PUBLICATIONS

Li et al. "The complete genome sequence of *Mycobacterium avium* subspecies *paratuberculosis*," PNAS, Aug. 2005, vol. 102, No. 35, pp. 12344-12349.
Li et al. "Early detection of *Mycobacterium avium* subsp. *paratuberculosis* infection in cattle with multiplex-bead based immunoassays," PLOS One, Dec. 2017, vol. 12, No. 12, e0189783, 16 pages.
Liu et al. "Systematic comparison of 2A peptides for cloning multi-genes in polycistronic vector," Scientific Reports, 2017, vol. 7, article 2193, 9 pages.
Lombard et al. "Herd-level prevalence of *Mycobacterium avium* subsp. *paratuberculosis* infection in United States dairy herds in 2007," Preventive Veterinary Medicine, 2013, vol. 108, pp. 234-238.
Morris et al. "Simian adenoviruses as vaccine vectors," Future Virology, 2016, vol. 11, No. 9, pp. 649-659.
Nacy et al. "*Mycobacterium Avium paratuberculosis*: Infrequent Human pathogen or Public Health Threat?" American Academy of Microbiology, 2008, 41 pages.
Naser et al. "In situ identification of mycobacteria in Crohn's disease patient tissue using confocal scanning laser microscopy," Molecular and Cellular Probes, 2002, vol. 16, pp. 41-48.
Radon et al. "Contact With Farm Animals in Early Life and Juvenile Inflammatory Bowel Disease: A Case-Control Study," Pediatrics, Aug. 2007, vol. 120, No. 2, pp. 354-361.
Ricchi et al. "Exploring MALDI-TOF MS approach for a rapid identification of *Mycobacterium avium* ssp. *paratuberculosis* field isolates," Journal of Applied Microbiology, 2016, vol. 122, pp. 568-577.
Richardson et al. "Presence of *Mycobacterium avium* Subspecies *paratuberculosis* Monitored Over Varying Temporal and Spatial Scales in River Catchments: Persistent Routes for Human Exposure," Microorganisms, 2019, vol. 7, article 136, 15 pages.
Scanu et al. "*Mycobacterium avium* Subspecies *paratuberculosis* Infection in Cases of Irritable Bowel Syndrome and Comparison with Crohn's Disease and Johne's Disease: Common Neural and Immune Pathogenicities," Journal of Clinical Microbiology, Dec. 2007, vol. 45, No. 12, pp. 3883-3890.
Sheridan "Ablynx's nanobody fragments go places antibodies cannot," Nature Biotechnology, Dec. 2017, vol. 34, No. 12, pp. 1115-1117.
Tizard et al. "p43, the protein product of the atypical insertion sequence IS900, is expressed in *Mycobacterium paratuberculosis*," Journal of General Microbiology, Aug. 1992, vol. 138, No. 8, pp. 1729-1736.
Van Der Burg et al. "Vaccines for established cancer: overcoming the challenges posed by immune evasion," Nature Reviews Cancer, Apr. 2016, vol. 16, pp. 219-233.
Official Action for European Patent Application No. 19752222.0, dated Feb. 21, 2024, 5 pages.
Bull et al. "A Novel Multi-Antigen Virally Vectored Vaccine against *Mycobacterium avium* Subspecies *paratuberculosis* ," PLOS One, Nov. 2007, vol. 2, No. 11, article e1229, 14 pages.
Park et al. "Development of vaccines to *Mycobacterium avium* subsp. *paratuberculosis* infection," Clinical and Experimental Vaccine Research, Jan. 2016, vol. 5, No. 2, pp. 108-116.
International Search Report and Written Opinion for International (PCT) Patent Application No. PCT/GB2019/01933, dated Oct. 4, 2019, 10 pages.
Yang Yilong "Protective Immunity of Targeting *Staphylococcus aureus* Surface Protein A (SasA)," Institute of Bioengineering, Academy of Military Medical Sciences, May 10, 2016, 93 pages (English abstract).
Official Action with English Translation for China Patent Application No. 201980059761.5, dated Jun. 28, 2024, 10 pages.

\* cited by examiner

SEQUENCE LISTING

<160> NUMBER OF SEQ ID NOS: 146

<210> SEQ ID NO 1
<211> LENGTH: 213
<212> TYPE: DNA
<213> ORGANISM: Mycobacterium avium paratuberculosis

<400> SEQUENCE: 1

```
atgaccgtga ccgaggtggt ggtggcccag cccgtgtggg ccggcgtgga cgccggcaag    60
gccgaccact actgcatggt gatcaacgac gacgcccaga ggctgctgag ccagagggtg   120
gccaacgacg aggccgccct gctggagctg atcgccgccg tgaccaccct ggccgacggc   180
ggcgaggtga cctgggccat cgacctgaac gcc                                213
```

<210> SEQ ID NO 2
<211> LENGTH: 71
<212> TYPE: PRT
<213> ORGANISM: Mycobacterium avium paratuberculosis

<400> SEQUENCE: 2

```
Met Thr Val Thr Glu Val Val Val Ala Gln Pro Val Trp Ala Gly Val
  1               5                  10                  15

Asp Ala Gly Lys Ala Asp His Tyr Cys Met Val Ile Asn Asp Asp Ala
             20                  25                  30

Gln Arg Leu Leu Ser Gln Arg Val Ala Asn Asp Glu Ala Ala Leu Leu
         35                  40                  45

Glu Leu Ile Ala Ala Val Thr Thr Leu Ala Asp Gly Gly Glu Val Thr
     50                  55                  60

Trp Ala Ile Asp Leu Asn Ala
 65                  70
```

-continued

```
<210> SEQ ID NO 3
<211> LENGTH: 14
<212> TYPE: PRT
<213> ORGANISM: Mycobacterium avium paratuberculosis

<400> SEQUENCE: 3

Met Val Ile Asn Asp Asp Ala Gln Arg Leu Leu Ser Gln Arg
1               5                   10

<210> SEQ ID NO 4
<211> LENGTH: 26
<212> TYPE: PRT
<213> ORGANISM: Mycobacterium avium paratuberculosis

<400> SEQUENCE: 4

Met Val Ile Asn Asp Asp Ala Gln Arg Leu Leu Ser Gln Arg Val Ala
1               5                   10                  15

Asn Asp Glu Ala Ala Leu Leu Glu Leu Ile
            20                  25

<210> SEQ ID NO 5
<211> LENGTH: 14
<212> TYPE: PRT
<213> ORGANISM: Artificial Sequence
<220> FEATURE:
<223> OTHER INFORMATION: Phosphorylated A0X short peptide
<220> FEATURE:
<221> NAME/KEY: MOD_RES
<222> LOCATION: (12)..(12)
<223> OTHER INFORMATION: PHOSPHORYLATION

<400> SEQUENCE: 5

Met Val Ile Asn Asp Asp Ala Gln Arg Leu Leu Ser Gln Arg
1               5                   10

<210> SEQ ID NO 6
<211> LENGTH: 26
<212> TYPE: PRT
<213> ORGANISM: Artificial Sequence
<220> FEATURE:
<223> OTHER INFORMATION: Phosphorylated A0X long peptide
<220> FEATURE:
<221> NAME/KEY: MOD_RES
<222> LOCATION: (12)..(12)
<223> OTHER INFORMATION: PHOSPHORYLATION

<400> SEQUENCE: 6

Met Val Ile Asn Asp Asp Ala Gln Arg Leu Leu Ser Gln Arg Val Ala
1               5                   10                  15

Asn Asp Glu Ala Ala Leu Leu Glu Leu Ile
            20                  25

<210> SEQ ID NO 7
<211> LENGTH: 15
<212> TYPE: PRT
<213> ORGANISM: Mycobacterium avium paratuberculosis

<400> SEQUENCE: 7

Val Thr Thr Leu Ala Asp Gly Gly Glu Val Thr Trp Ala Ile Asp
1               5                   10                  15

<210> SEQ ID NO 8
<211> LENGTH: 18
<212> TYPE: PRT
```

```
<213> ORGANISM: Mycobacterium avium paratuberculosis

<400> SEQUENCE: 8

Val Thr Thr Leu Ala Asp Gly Gly Glu Val Th

```
<210> SEQ ID NO 13
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (26)..(27)
<223> OTHER INFORMATION: Peptide linker, A, or AA between residues 26
      and 27

<400> SEQUENCE: 13

Met Val Ile Asn Asp Asp Ala Gln Arg Leu Leu Ser Gln Arg Val Ala
1               5                   10                  15

Asn Asp Glu Ala Ala Leu Leu Glu Leu Ile Val Thr Thr Leu Ala Asp
            20                  25                  30

Gly Gly Glu Val Thr Trp Ala Ile Asp
        35                  40

<210> SEQ ID NO 14
<211> LENGTH: 44
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (26)..(27)
<223> OTHER INFORMATION: Peptide linker, A, or AA between residues 26
      and 27

<400> SEQUENCE: 14

Met Val Ile Asn Asp Asp Ala Gln Arg Leu Leu Ser Gln Arg Val Ala
1               5                   10                  15

Asn Asp Glu Ala Ala Leu Leu Glu Leu Ile Val Thr Thr Leu Ala Asp
            20                  25                  30

Gly Gly Glu Val Thr Trp Ala Ile Asp Leu Asn Ala
        35                  40

<210> SEQ ID NO 15
<211> LENGTH: 34
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (20)..(21)
<223> OTHER INFORMATION: Peptide linker or C between residues 20 and 21

<400> SEQUENCE: 15

Glu Val Val Val Ala Gln Pro Val Trp Ala Gly Val Asp Ala Gly Lys
1               5                   10                  15

Ala Asp His Tyr Met Val Ile Asn Asp Asp Ala Gln Arg Leu Leu Ser
            20                  25                  30

Gln Arg

<210> SEQ ID NO 16
<211> LENGTH: 46
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

<222> LOCATION: (20)..(21)
<223> OTHER INFORMATION: Peptide linker or C between residues 20 and 21

<400> SEQUENCE: 16

Glu Val Val Ala Gln Pro Val Trp Ala Gly Val Asp Ala Gly Lys
1               5                   10                  15

Ala Asp His Tyr Met Val Ile Asn Asp Asp Ala Gln Arg Leu Ser
                20                  25                  30

Gln Arg Val Ala Asn Asp Glu Ala Ala Leu Leu Glu Leu Ile
            35                  40                  45

<210> SEQ ID NO 17
<211> LENGTH: 38
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(25)
<223> OTHER INFORMATION: Peptide linker or C between residues 24 and 25

<400> SEQUENCE: 17

Met Thr Val Thr Glu Val Val Val Ala Gln Pro Val Trp Ala Gly Val
1               5                   10                  15

Asp Ala Gly Lys Ala Asp His Tyr Met Val Ile Asn Asp Asp Ala Gln
                20                  25                  30

Arg Leu Leu Ser Gln Arg
            35

<210> SEQ ID NO 18
<211> LENGTH: 50
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(25)
<223> OTHER INFORMATION: Peptide linker or C between residues 24 and 25

<400> SEQUENCE: 18

Met Thr Val Thr Glu Val Val Val Ala Gln Pro Val Trp Ala Gly Val
1               5                   10                  15

Asp Ala Gly Lys Ala Asp His Tyr Met Val Ile Asn Asp Asp Ala Gln
                20                  25                  30

Arg Leu Leu Ser Gln Arg Val Ala Asn Asp Glu Ala Ala Leu Leu Glu
            35                  40                  45

Leu Ile
    50

<210> SEQ ID NO 19
<211> LENGTH: 64
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (20)..(21)
<223> OTHER INFORMATION: Peptide linker or C between residues 20 and 21
<220> FEATURE:
<221> NAME/KEY: MISC_FEATURE
<222> LOCATION: (46)..(47)
<223> OTHER INFORMATION: Peptide linker, A, or AA between residues 46
    and 47

<400> SEQUENCE: 19

Glu Val Val Ala Gln Pro Val Trp Ala Gly Val Asp Ala Gly Lys
1               5                   10                  15

Ala Asp His Tyr Met Val Ile Asn Asp Ala Gln Arg Leu Leu Ser
            20                  25                  30

Gln Arg Val Ala Asn Asp Glu Ala Ala Leu Leu Glu Leu Ile Val Thr
        35                  40                  45

Thr Leu Ala Asp Gly Gly Glu Val Thr Trp Ala Ile Asp Leu Asn Ala
    50                  55                  60

<210> SEQ ID NO 20
<211> LENGTH: 68
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (24)..(25)
<223> OTHER INFORMATION: Peptide linker or C between residues 24 and 25
<220> FEATURE:
<221> NAME/KEY: MISC_FEATURE
<222> LOCATION: (50)..(51)
<223> OTHER INFORMATION: Peptide linker, A, or AA between residues 50
      and 51

<400> SEQUENCE: 20

Met Thr Val Thr Glu Val Val Ala Gln Pro Val Trp Ala Gly Val
1               5                   10                  15

Asp Ala Gly Lys Ala Asp His Tyr Met Val Ile Asn Asp Ala Gln
            20                  25                  30

Arg Leu Leu Ser Gln Arg Val Ala Asn Asp Glu Ala Ala Leu Leu Glu
        35                  40                  45

Leu Ile Val Thr Thr Leu Ala Asp Gly Gly Glu Val Thr Trp Ala Ile
    50                  55                  60

Asp Leu Asn Ala
65

<210> SEQ ID NO 21
<211> LENGTH: 606
<212> TYPE: DNA
<213> ORGANISM: Mycobacterium avium paratuberculosis

<400> SEQUENCE: 21
atgcctctgc tgaccatcgg cgatcagttc cccgcctacg agcttgaccg cgtgatcgcg        60
ggcgacctgt ccaaggtcga cgccaagcag cccggtgact acttcaccac cgtcaccagc       120
gaggaccacg ccggcaagtg cgcgtggtg ttcttctggc ccaaggactt caccttcgtc        180
tgccccaccg agatcgccac cttcggcaag ctcaacgacg agttcgagga ccgcgacgcc       240
caggtgctcg cgtctcgat cgacagcgag ttcgtccact tcaactggcg cgcccagcac        300
gaggacctga gaacctgcc gttcccgatg ctctcggaca tcaagcgcga actgagcctg        360
gccaccggtg ttctcaacgc cgacggcgtg gccgaccggg ccaccttcat cgtcgacccg       420
aacaacgaga tccagttcgt ctcggtcacc gcgggttcgg tgggccgcaa cgtcgaggaa       480
gtgctgcggg tgctggatgc gctgcagtcc gacgagctgt gcgcgtgcaa ctggcgcaag       540 ggtgaccccga cgctgaacgc caccgaactg ctcaaggcct tgcttaaaaa gggcgaattc       600
gtttaa                                                                   606

<210> SEQ ID NO 22
<211> LENGTH: 195
<212> TYPE: PRT
<213> ORGANISM: Mycobacterium avium paratuberculosis

<400> SEQUENCE: 22

```
Met Pro Leu Leu Thr Ile Gly Asp Gln Phe Pro Ala Tyr Glu Leu Asp
1               5                   10                  15

Arg Val Ile Ala Gly Asp Leu Ser Lys Val Asp Ala Lys Gln Pro Gly
            20                  25                  30

Asp Tyr Phe Thr Thr Val Thr Ser Glu Asp His Ala Gly Lys Trp Arg
        35                  40                  45

Val Val Phe Phe Trp Pro Lys Asp Phe Thr Phe Val Cys Pro Thr Glu
    50                  55                  60

Ile Ala Thr Phe Gly Lys Leu Asn Asp Glu Phe Glu Asp Arg Asp Ala
65                  70                  75                  80

Gln Val Leu Gly Val Ser Ile Asp Ser Glu Phe Val His Phe Asn Trp
                85                  90                  95

Arg Ala Gln His Glu Asp Leu Lys Asn Leu Pro Phe Pro Met Leu Ser
            100                 105                 110

Asp Ile Lys Arg Glu Leu Ser Leu Ala Thr Gly Val Leu Asn Ala Asp
        115                 120                 125

Gly Val Ala Asp Arg Ala Thr Phe Ile Val Asp Pro Asn Asn Glu Ile
    130                 135                 140

Gln Phe Val Ser Val Thr Ala Gly Ser Val Gly Arg Asn Val Glu Glu
145                 150                 155                 160

Val Leu Arg Val Leu Asp Ala Leu Gln Ser Asp Glu Leu Cys Ala Cys
                165                 170                 175

Asn Trp Arg Lys Gly Asp Pro Thr Leu Asn Ala Thr Glu Leu Leu Lys
            180                 185                 190

Ala Ser Ala
        195
```

<210> SEQ ID NO 23
<211> LENGTH: 801
<212> TYPE: DNA
<213> ORGANISM: Mycobacterium avium

<400> SEQUENCE: 23

```
atgactgcgc cagtgttctc gataattatc cctaccttca atgcagcggt gacgctgcaa      60
gcctgcctcg gaagcatcgt cgggcagacc taccgggaag tggaagtggt ccttgtcgac     120
ggcggttcga ccgatcggac cctcgacatc gcgaacagtt tccgcccgga actcggctcg     180
cgactggtcg ttcacagcgg gcccgatgat ggccctacg acgccatgaa ccgcggcgtc      240
ggcgtagcca caggcgaatg ggtacttttt ttaggcgccg acgacaccct ctacgaacca     300
accacgttgg cccaggtagc cgcttttctc ggcgaccatg cggcaagcca tcttgtctat     360
ggcgatgttg tgatgcgttc gacgaaaagc cggcatgccg gacctttcga cctcgaccgc     420
ctcctatttg agacgaattt gtgccaccaa tcgatctttt accgccgtga gcttttcgac     480
ggcatcggcc cttacaacct gcgctaccga gtctgggcgg actgggactt caatattcgc     540
tgcttctcca acccggcgct gattacccgc tacatggacg tcgtgatttc gaatacaaac     600
gacatgaccg gcttcagcat gaggcagggg actgataaag agttcagaaa acggctgcca     660
atgtacttct gggttgcagg gtgggagact tgcaggcgca tgctggcgtt tttgaaagac     720
```

-continued

```
aaggagaatc gccgtctggc cttgcgtacg cggttgataa gggttaaggc cgtctccaaa    780
gaacgaagcg cagaaccgta g                                              801
```

<210> SEQ ID NO 24
<211> LENGTH: 266
<212> TYPE: PRT
<213> ORGANISM: Mycobacterium avium paratuberculosis

<400> SEQUENCE: 24

```
Met Thr Ala Pro Val Phe Ser Ile Ile Pro Thr Phe Asn Ala Ala
1               5                   10                  15

Val Thr Leu Gln Ala Cys Leu Gly Ser Ile Val Gly Gln Thr Tyr Arg
            20                  25                  30

Glu Val Glu Val Val Leu Val Asp Gly Gly Ser Thr Asp Arg Thr Leu
        35                  40                  45

Asp Ile Ala Asn Ser Phe Arg Pro Glu Leu Gly Ser Arg Leu Val Val
    50                  55                  60

His Ser Gly Pro Asp Asp Gly Pro Tyr Asp Ala Met Asn Arg Gly Val
65                  70                  75                  80

Gly Val Ala Thr Gly Glu Trp Val Leu Phe Leu Gly Ala Asp Asp Thr
                85                  90                  95

Leu Tyr Glu Pro Thr Thr Leu Ala Gln Val Ala Ala Phe Leu Gly Asp
            100                 105                 110

His Ala Ala Ser His Leu Val Tyr Gly Asp Val Val Met Arg Ser Thr
        115                 120                 125

Lys Ser Arg His Ala Gly Pro Phe Asp Leu Asp Arg Leu Leu Phe Glu
    130                 135                 140

Thr Asn Leu Cys His Gln Ser Ile Phe Tyr Arg Arg Glu Leu Phe Asp
145                 150                 155                 160

Gly Ile Gly Pro Tyr Asn Leu Arg Tyr Arg Val Trp Ala Asp Trp Asp
                165                 170                 175

Phe Asn Ile Arg Cys Phe Ser Asn Pro Ala Leu Ile Thr Arg Tyr Met
            180                 185                 190

Asp Val Val Ile Ser Glu Tyr Asn Asp Met Thr Gly Phe Ser Met Arg
        195                 200                 205

Gln Gly Thr Asp Lys Glu Phe Arg Lys Arg Leu Pro Met Tyr Phe Trp
    210                 215                 220

Val Ala Gly Trp Glu Thr Cys Arg Arg Met Leu Ala Phe Leu Lys Asp
225                 230                 235                 240

Lys Glu Asn Arg Arg Leu Ala Leu Arg Thr Arg Leu Ile Arg Val Lys
                245                 250                 255

Ala Val Ser Lys Glu Arg Ser Ala Glu Pro
            260                 265
```

<210> SEQ ID NO 25
<211> LENGTH: 417
<212> TYPE: DNA
<213> ORGANISM: Mycobacterium avium paratuberculosis

<400> SEQUENCE: 25

```
cgatttcgcc gccaccgcca cgccgaaatc atcctgagca tgcccggatt cggcgtcatc    60
ctgggcgctg agttcctcgc cgccaccggc ggggacatgg ccgcattcgc ctccgccgac   120
cgcctcgccg cgtcgccgg cctggcgccg gtaccacgag attccggccg catcagcgga   180
aacctcaaac gccccgacg ctacgaccgg cgcctgctgc cgcctgcta cctgtcggcc   240
```

```
ttggtcagca tccgcaccga cccctcctcg cgcacctact acgaccgaaa acgcaccgaa    300
ggaaaacgcc acacccaagc cgtcctcgcc ctggcccgcc gccgcctcaa cgtcctgtgg    360
gccatgctgc gcgaccacgc tgtctaccac cccgcaacca ctaccgcggc ggcttga       417
```

<210> SEQ ID NO 26
<211> LENGTH: 138
<212> TYPE: PRT
<213> ORGANISM: Mycobacterium avium

<400> SEQUENCE: 26

```
Arg Phe Arg Arg His Arg His Ala Glu Ile Ile Leu Ser Met Pro Gly
1               5                   10                  15

Phe Gly Val Ile Leu Gly Ala Glu Phe Leu Ala Ala Thr Gly Gly Asp
            20                  25                  30

Met Ala Ala Phe Ala Ser Ala Asp Arg Leu Ala Gly Val Ala Gly Leu
        35                  40                  45

Ala Pro Val Pro Arg Asp Ser Gly Arg Ile Ser Gly Asn Leu Lys Arg
    50                  55                  60

Pro Arg Arg Tyr Asp Arg Arg Leu Leu Arg Ala Cys Tyr Leu Ser Ala
65                  70                  75                  80

Leu Val Ser Ile Arg Thr Asp Pro Ser Ser Arg Thr Tyr Tyr Asp Arg
                85                  90                  95

Lys Arg Thr Glu Gly Lys Arg His Thr Gln Ala Val Leu Ala Leu Ala
            100                 105                 110

Arg Arg Arg Leu Asn Val Leu Trp Ala Met Leu Arg Asp His Ala Val
        115                 120                 125

Tyr His Pro Ala Thr Thr Thr Ala Ala Ala
    130                 135
```

<210> SEQ ID NO 27
<211> LENGTH: 402
<212> TYPE: DNA
<213> ORGANISM: Mycobacterium avium paratuberculosis

<400> SEQUENCE: 27

```
cgatttcgcc gccaccgcca cgccgaaatc atcctgagca tgcccggatt cggcgtcatc     60
ctgggcgctg agttcctcgc cgccaccggc ggggacatgg ccgcattcgc ctccgccgac    120
cgcctcgccg gcgtcgccgg cctggcgccg gtaccacgag attccggccg catcagcgga    180
aacctcaaac gccccgacg ctacgaccgg cgcctgctgc gcgcctgcgt cagcatccgc     240
accgacccct cctcgcgcac ctactacgac cgaaaacgca ccgaaggaaa acgccacacc    300
caagccgtcc tcgccctggc cgccgccgcc ctcaacgtcc tgtgggccat gctgcgcgac    360
cacgctgtct accaccccgc aaccactacc gcggcggctt ga                       402
```

<210> SEQ ID NO 28
<211> LENGTH: 133
<212> TYPE: PRT
<213> ORGANISM: Mycobacterium avium paratuberculosis

<400> SEQUENCE: 28

```
Arg Phe Arg Arg His Arg His Ala Glu Ile Ile Leu Ser Met Pro Gly
1               5                   10                  15

Phe Gly Val Ile Leu Gly Ala Glu Phe Leu Ala Ala Thr Gly Gly Asp
            20                  25                  30

Met Ala Ala Phe Ala Ser Ala Asp Arg Leu Ala Gly Val Ala Gly Leu
        35                  40                  45
```

Ala Pro Val Pro Arg Asp Ser Gly Arg Ile Ser Gly Asn Leu Lys Arg
     50                  55                  60

Pro Arg Arg Tyr Asp Arg Arg Leu Leu Arg Ala Cys Val Ser Ile Arg
 65              70                  75                  80

Thr Asp Pro Ser Ser Arg Thr Tyr Tyr Asp Lys Arg Thr Glu Gly
                 85                  90                  95

Lys Arg His Thr Gln Ala Val Leu Ala Leu Ala Arg Arg Arg Leu Asn
             100                 105                 110

Val Leu Trp Ala Met Leu Arg Asp His Ala Val Tyr His Pro Ala Thr
         115                 120                 125

Thr Thr Ala Ala Ala
     130

<210> SEQ ID NO 29
<211> LENGTH: 1335
<212> TYPE: DNA
<213> ORGANISM: Mycobacterium avium paratuberculosis

<400> SEQUENCE: 29
gtgactgaag ccaatgagtg caactcggcg tcgcgaaagg tttcagtcgc ggttgagcaa      60
gacaccgcaa gactactgga gtgcgtgcac aagcgccccc agctcgcggc tgaaagcgga     120
tgcaaagggg ttcgaagctt gagcaacatg cgaaggggag aacggcctat gagcctggga     180
caggttttcg acccgcgcgc gaatgcactt aatgcgtggc gcttggtgtt ggcgagcggg     240
gtgatcctat ggcattcgtt tccgctcact ggacgtatgc cgtgggcgcc gttcgtccag     300
ttgcttggcc ttggatgcgt tgatggtttc tttgcggtct ccggctatct catcgtctcg     360
agctggcttc gcaacccgca tcccgcccaa tacttcaccg ctcgatgtct tcgtattctc     420
ccgggtctgt ggatctgtct catcttgacg gcgtttgtca tcgctccgat aggtgtgggc     480
gcccagggcg gttcggccgc gaaactactg atgtccggcg ctccgatcga gtatgtgcta     540
aaagacagtg cggtttggat ggttaagttc gatatcggtg gcacacctcg cgatattcca     600
gttgcgggta tttggaacgg ttctctgtgg acattgggtt gggaggtgct ttgctatatc     660
ggcgtagcag tatttggtat gctcggactt cttagtcgcc gttggttcgt tccagggata     720
ttgatcctgg cgctgtcgtg gtcggtgttc ttgccggcat ggggcggaat acacgcgatc     780
gcctccaatg ctgcgcgatt cgctgtgatg ttttcggccg gagcgttgct gtatcaattc     840
cgtaacgtga ttccggctcg gtggtccttc gttgccgtcg gcctcattat cgttgtggtt     900
tcctctgccg tgctgccgga ctaccggttg gtggcggccc ttccgatggc gtacctaatc     960
atcgcttcgg gttcgctcat ccacaatcaa aggatgaggt ccgcaccga tctatcctat    1020 ggagtatata tttatgcgtt tccaattcag caagtgctgg tcctgtgtgg attcgccgag    1080
ataaatccaa tcgctttctg cgcgatttct gtcgcagcta ttttgccgct cgccgcgctc    1140
agttggttct tggtcgagaa acctgcgttg tcctggaaga gtcgtctccg gcggaaaaac    1200
agttcaattg cgctagccaa tatggaagat ggtggatcag tcggccgctc aaatgacatt    1260
cccggaaggc gggcccgctt tattggcgag aaagccgaag atcctcccgc gccgagccca    1320
agaccggctt tgtaa                                                    1335

<210> SEQ ID NO 30
<211> LENGTH: 444
<212> TYPE: PRT
<213> ORGANISM: Mycobacterium avium paratuberculosis

```
<400> SEQUENCE: 30

Val Thr Glu Ala Asn Glu Cys Asn Ser Ala Ser Arg Lys Val Ser Val
1               5                   10                  15

Ala Val Glu Gln Asp Thr Ala Arg Leu Leu Glu Cys Val His Lys Arg
            20                  25                  30

Pro Gln Leu Ala Ala Glu Ser Gly Cys Lys Gly Val Arg Ser Leu Ser
        35                  40                  45

Asn Met Arg Arg Gly Glu Arg Pro Met Ser Leu Gly Gln Val Phe Asp
    50                  55                  60

Pro Arg Ala Asn Ala Leu Asn Ala Trp Arg Leu Val Leu Ala Ser Gly
65                  70                  75                  80

Val Ile Leu Trp His Ser Phe Pro Leu Thr Gly Arg Met Pro Trp Ala
                85                  90                  95

Pro Phe Val Gln Leu Leu Gly Leu Gly Cys Val Asp Gly Phe Ala
            100                 105                 110

Val Ser Gly Tyr Leu Ile Val Ser Ser Trp Leu Arg Asn Pro His Pro
            115                 120                 125

Ala Gln Tyr Phe Thr Ala Arg Cys Leu Arg Ile Leu Pro Gly Leu Trp
        130                 135                 140

Ile Cys Leu Ile Leu Thr Ala Phe Val Ile Ala Pro Ile Gly Val Gly
145                 150                 155                 160

Ala Gln Gly Gly Ser Ala Ala Lys Leu Leu Met Ser Gly Ala Pro Ile
                165                 170                 175

Glu Tyr Val Leu Lys Asp Ser Ala Val Trp Met Val Lys Phe Asp Ile
            180                 185                 190

Gly Gly Thr Pro Arg Asp Ile Pro Val Ala Gly Ile Trp Asn Gly Ser
        195                 200                 205

Leu Trp Thr Leu Gly Trp Glu Val Leu Cys Tyr Ile Gly Val Ala Val
210                 215                 220

Phe Gly Met Leu Gly Leu Leu Ser Arg Arg Trp Phe Val Pro Gly Ile
225                 230                 235                 240

Leu Ile Leu Ala Leu Ser Trp Ser Val Phe Leu Pro Ala Trp Gly Gly
                245                 250                 255

Ile His Ala Ile Ala Ser Asn Ala Ala Arg Phe Ala Val Met Phe Ser
            260                 265                 270

Ala Gly Ala Leu Leu Tyr Gln Phe Arg Asn Val Ile Pro Ala Arg Trp
        275                 280                 285

Ser Phe Val Ala Val Gly Leu Ile Ile Val Val Ser Ser Ala Val
    290                 295                 300

Leu Pro Asp Tyr Arg Leu Val Ala Ala Leu Pro Met Ala Tyr Leu Ile
305                 310                 315                 320

Ile Ala Ser Gly Ser Leu Ile His Asn Gln Arg Met Arg Phe Arg Thr
                325                 330                 335

Asp Leu Ser Tyr Gly Val Tyr Ile Tyr Ala Phe Pro Ile Gln Gln Val
            340                 345                 350

Leu Val Leu Cys Gly Phe Ala Glu Ile Asn Pro Ile Ala Phe Cys Ala
        355                 360                 365

Ile Ser Val Ala Ala Ile Leu Pro Leu Ala Ala Leu Ser Trp Phe Leu
    370                 375                 380

Val Glu Lys Pro Ala Leu Ser Trp Lys Ser Arg Leu Arg Arg Lys Asn
385                 390                 395                 400

Ser Ser Ile Ala Leu Ala Asn Met Glu Asp Gly Gly Ser Val Gly Arg
                405                 410                 415
```

Ser Asn Asp Ile Pro Gly Arg Arg Ala Arg Phe Ile Gly Glu Lys Ala
            420                 425                 430

Glu Asp Pro Pro Ala Pro Ser Pro Arg Pro Ala Leu
        435                 440

<210> SEQ ID NO 31
<211> LENGTH: 585
<212> TYPE: DNA
<213> ORGANISM: Artificial Sequence
<220> FEATURE:
<223> OTHER INFORMATION: Codon Optimised ahpC

<400> SEQUENCE: 31 cccctCtctca ctatcggaga ccagttcccc gcttacgaac ttacagctct tatcgctgga    60
gatctgagta aggttgacgc caaacagccc ggcgattatt tcactaccgt taccagtgag   120
gatcacgcag gtaaatggag agtcgtcttc ttctggccta agacttcac ctttgtgtgc    180 cctactgaga tcgcaacatt cgggaagctg aacgatgagt tcgaagatcg agacgcacag   240
gttttgggcg tgtctatcga ttccgagttc gtgcacttca actggagagc acagcatgaa   300
gatctcaaga accttccatt ccccatgctc agcgacatca agagaaact gagcttggca    360 acaggtgttc tgaatgctga tggcgttgct gacagagcaa cattcattgt tgaccccaat   420
aacgagatcc agttcgtttc cgttactgct ggttctgtcg gtagaaacgt tgaagaggtc   480
ctgagagttc tcgacgcact tcagagtgat gaactgtgtg cctgcaattg gcggaaagga   540
gatcctactc tcaatgccac agagctgctt aaagcaagtg ctctc                    585

<210> SEQ ID NO 32
<211> LENGTH: 195
<212> TYPE: PRT
<213> ORGANISM: Mycobacterium avium paratuberculosis

<400> SEQUENCE: 32

Pro Leu Leu Thr Ile Gly Asp Gln Phe Pro Ala Tyr Glu Leu Thr Ala
1               5                   10                  15

Leu Ile Ala Gly Asp Leu Ser Lys Val Asp Ala Lys Gln Pro Gly Asp
            20                  25                  30

Tyr Phe Thr Thr Val Thr Ser Glu Asp His Ala Gly Lys Trp Arg Val
        35                  40                  45

Val Phe Phe Trp Pro Lys Asp Phe Thr Phe Val Cys Pro Thr Glu Ile
    50                  55                  60

Ala Thr Phe Gly Lys Leu Asn Asp Glu Phe Glu Asp Arg Asp Ala Gln
65                  70                  75                  80

Val Leu Gly Val Ser Ile Asp Ser Glu Phe Val His Phe Asn Trp Arg
                85                  90                  95

Ala Gln His Glu Asp Leu Lys Asn Leu Pro Phe Pro Met Leu Ser Asp
            100                 105                 110

Ile Lys Arg Glu Leu Ser Leu Ala Thr Gly Val Leu Asn Ala Asp Gly
        115                 120                 125

Val Ala Asp Arg Ala Thr Phe Ile Val Asp Pro Asn Asn Glu Ile Gln
    130                 135                 140

Phe Val Ser Val Thr Ala Gly Ser Val Gly Arg Asn Val Glu Glu Val
145                 150                 155                 160

Leu Arg Val Leu Asp Ala Leu Gln Ser Asp Glu Leu Cys Ala Cys Asn
                165                 170                 175

Trp Arg Lys Gly Asp Pro Thr Leu Asn Ala Thr Glu Leu Leu Lys Ala

Ser Ala Leu
    195

<210> SEQ ID NO 33
<211> LENGTH: 729
<212> TYPE: DNA
<213> ORGANISM: Artificial Sequence
<220> FEATURE:
<223> OTHER INFORMATION: Modified Gsd

<400> SEQUENCE: 33

```
ggatccattg tcggacagac ctatagagag gtggaagttg tcctggtcga tggtggatct    60
acagatagga ctctcgacat tgccaactcc tttagaccag agctcggttc aaggctcgtt   120
gttcattctg gaccagatga tggaccatac gacgccatga acagaggtgt tggagttgct   180
acaggagaat gggtcttgtt ccttggagct gatgacactc tgtacgaacc gactacattg   240
gctcaggttg cagcattttt gggagatcat gcagcttctc accttgtgta cggagatgtg   300
gtcatgagat ccaccaagtc cagacatgct ggaccattcg atcttgacag actcctgttc   360
gagaccaacc tctgtcatca gagcatcttc tacagacggg aactcttcga cggaattgga   420
ccttacaacc tcaggtacag ggtttgggca gactgggatt caacatcag gtgcttctcg    480
aacccagctt tgatcacacg gtacatggat gttgtgatct ccgagtacaa cgatatgacc   540
ggcttctcca tgagacaggg aaccgacaaa gagttcagga agcgcttgcc aatgtacttc   600
tgggttgctg gatgggaaac atgtcggaga atgcttgctt tcctgaagga caaggagaac   660
aggagacttg ctctcaggac tagactcatc agggtcaaag cagtgtccaa ggaaaggagt   720
gctgaacct                                                           729
```

<210> SEQ ID NO 34
<211> LENGTH: 243
<212> TYPE: PRT
<213> ORGANISM: Mycobacterium avium paratuberculosis

<400> SEQUENCE: 34

Gly Ser Ile Val Gly Gln Thr Tyr Arg Glu Val Glu Val Val Leu Val
1               5                   10                  15

Asp Gly Gly Ser Thr Asp Arg Thr Leu Asp Ile Ala Asn Ser Phe Arg
            20                  25                  30

Pro Glu Leu Gly Ser Arg Leu Val Val His Ser Gly Pro Asp Asp Gly
        35                  40                  45

Pro Tyr Asp Ala Met Asn Arg Gly Val Gly Val Ala Thr Gly Glu Trp
    50                  55                  60

Val Leu Phe Leu Gly Ala Asp Asp Thr Leu Tyr Glu Pro Thr Thr Leu
65                  70                  75                  80

Ala Gln Val Ala Ala Phe Leu Gly Asp His Ala Ala Ser His Leu Val
                85                  90                  95

Tyr Gly Asp Val Val Met Arg Ser Thr Lys Ser Arg His Ala Gly Pro
            100                 105                 110

Phe Asp Leu Asp Arg Leu Leu Phe Glu Thr Asn Leu Cys His Gln Ser
        115                 120                 125

Ile Phe Tyr Arg Arg Glu Leu Phe Asp Gly Ile Gly Pro Tyr Asn Leu
    130                 135                 140

Arg Tyr Arg Val Trp Ala Asp Trp Asp Phe Asn Ile Arg Cys Phe Ser
145                 150                 155                 160

```
Asn Pro Ala Leu Ile Thr Arg Tyr Met Asp Val Val Ile Ser Glu Tyr
                165                 170                 175

Asn Asp Met Thr Gly Phe Ser Met Arg Gln Gly Thr Asp Lys Glu Phe
            180                 185                 190

Arg Lys Arg Leu Pro Met Tyr Phe Trp Val Ala Gly Trp Glu Thr Cys
        195                 200                 205

Arg Arg Met Leu Ala Phe Leu Lys Asp Lys Glu Asn Arg Arg Leu Ala
    210                 215                 220

Leu Arg Thr Arg Leu Ile Arg Val Lys Ala Val Ser Lys Glu Arg Ser
225                 230                 235                 240

Ala Glu Pro

<210> SEQ ID NO 35
<211> LENGTH: 420
<212> TYPE: DNA
<213> ORGANISM: Artificial Sequence
<220> FEATURE:
<223> OTHER INFORMATION: Codon Optimised P12

<400> SEQUENCE: 35
agaattcgga gacatagaca tgcagagatc atcctgagca tgcctggatt tggcgttatc      60
ctcggagctg aatttcttgc agcaacagga ggtgatatgg cagcttttcgc atcagctgac    120 agattggctg gagttgcagg tttggctcca gttccaagag attcagggag aatcagcggt    180
aacctcaaga gacctagacg ctacgacaga agactgctta gagcctgcta tctgagtgct    240
ttggttagca ttagaaccga cccctctagt cgaacctact acgataggaa gcggactgaa    300
ggtaagagac atacccaggc agtgttggca cttgctagaa gacggcttaa tgttctgtgg    360
gctatgctga gagatcatgc cgtgtaccat cctgctacca aacagctgc tgctagactt     420

<210> SEQ ID NO 36
<211> LENGTH: 140
<212> TYPE: PRT
<213> ORGANISM: Mycobacterium avium paratuberculosis

<400> SEQUENCE: 36

Arg Ile Arg Arg His Arg His Ala Glu Ile Ile Leu Ser Met Pro Gly
1               5                   10                  15

Phe Gly Val Ile Leu Gly Ala Glu Phe Leu Ala Ala Thr Gly Gly Asp
            20                  25                  30

Met Ala Ala Phe Ala Ser Ala Asp Arg Leu Gly Val Ala Gly Leu
        35                  40                  45

Ala Pro Val Pro Arg Asp Ser Gly Arg Ile Ser Gly Asn Leu Lys Arg
    50                  55                  60

Pro Arg Arg Tyr Asp Arg Arg Leu Leu Arg Ala Cys Tyr Leu Ser Ala
65                  70                  75                  80

Leu Val Ser Ile Arg Thr Asp Pro Ser Ser Arg Thr Tyr Tyr Asp Arg
                85                  90                  95

Lys Arg Thr Glu Gly Lys Arg His Thr Gln Ala Val Leu Ala Leu Ala
            100                 105                 110

Arg Arg Arg Leu Asn Val Leu Trp Ala Met Leu Arg Asp His Ala Val
        115                 120                 125

Tyr His Pro Ala Thr Thr Thr Ala Ala Ala Arg Leu
    130                 135                 140

<210> SEQ ID NO 37
<211> LENGTH: 405
```

```
<212> TYPE: DNA
<213> ORGANISM: Artificial Sequence
<220> FEATURE:
<223> OTHER INFORMATION: Modified P12

<400> SEQUENCE: 37
agaattcgga gacatagaca tgcagagatc atcctgagca tgcctggatt tggcgttatc      60
ctcggagctg aatttcttgc agcaacagga ggtgatatgg cagctttcgc atcagctgac     120
agattggctg gagttgcagg tttggctcca gttccaagag attcaggag aatcagcggt      180 aacctcaaga gacctagacg ctacgacaga agactgctta gagcctgcgt tagcattaga    240 accgaccct ctagtcgaac ctactacgat aggaagcgga ctgaaggtaa gagacatacc     300
caggcagtgt tggcacttgc tagaagacgg cttaatgttc tgtgggctat gctgagagat    360
catgccgtgt accatcctgc taccacaaca gctgctgcta gactt                    405

<210> SEQ ID NO 38
<211> LENGTH: 135
<212> TYPE: PRT
<213> ORGANISM: Mycobacterium avium paratuberculosis

<400> SEQUENCE: 38

Arg Ile Arg Arg His Arg His Ala Glu Ile Ile Leu Ser Met Pro Gly
1

```
tctgtgagtt cagccgtgtt gccaaactat agacttgttg ctgctctccc catggcctac    480
cataatcagc gaatgaggtt tcggacagat ctgtcctatg gtgtgtacgg gttcgctgaa    540
atcaatccca tcgctctggt tgagaaacct gccctgtctt ggaaatccag actgagacgg    600
aagaactctt ccatcgctct cgcaaacatg aagatggtg gtagtgttgg aaggagtaac     660
gacatccctg ggaggagggc tagatttatt ggtgagaaag ccgaagatcc tcctgctcca    720
tctcctagac ccgccttg                                                  738
```

```
<210> SEQ ID NO 40
<211> LENGTH: 246
<212> TYPE: PRT
<213> ORGANISM: Mycobacterium avium paratuberculosis

<400> SEQUENCE: 40
```

Lys Leu Arg Arg Gly Glu Arg Pro Met Ser Leu Gly Gln Val Phe Asp
1               5                   10                  15

Pro Arg Ala Asn Ala Leu His Ser Phe Pro Leu Thr Gly Arg Met Pro
            20                  25                  30

Trp Ala Pro Phe Ile Val Ser Ser Trp Leu Arg Asn Pro His Pro Ala
        35                  40                  45

Gln Tyr Phe Thr Ala Arg Cys Leu Arg Ile Leu Pro Gly Leu Trp Ile
    50                  55                  60

Gly Ala Gln Gly Gly Ser Ala Ala Lys Leu Leu Met Ser Gly Ala Pro
65                  70                  75                  80

Ile Glu Tyr Val Leu Lys Asp Ser Ala Val Trp Met Phe Lys Phe Asp
                85                  90                  95

Ile Gly Gly Thr Pro Arg Asp Ile Pro Val Ala Gly Ile Trp Asn Gly
            100                 105                 110

Ser Leu Trp Thr Pro Ala Trp Gly Gly Ile His Ala Ile Ala Ser Asn
        115                 120                 125

Ala Tyr Gln Phe Arg Asn Val Ile Pro Ala Arg Trp Ser Val Ser Ser
    130                 135                 140

Ala Val Leu Pro Asn Tyr Arg Leu Val Ala Ala Leu Pro Met Ala Tyr
145                 150                 155                 160

His Asn Gln Arg Met Arg Phe Arg Thr Asp Leu Ser Tyr Gly Val Tyr
                165                 170                 175

Gly Phe Ala Glu Ile Asn Pro Ile Ala Leu Val Glu Lys Pro Ala Leu
            180                 185                 190

Ser Trp Lys Ser Arg Leu Arg Arg Lys Asn Ser Ser Ile Ala Leu Ala
        195                 200                 205

Asn Met Glu Asp Gly Gly Ser Val Gly Arg Ser Asn Asp Ile Pro Gly
    210                 215                 220

Arg Arg Ala Arg Phe Ile Gly Glu Lys Ala Glu Asp Pro Pro Ala Pro
225                 230                 235                 240

Ser Pro Arg Pro Ala Leu
                245

```
<210> SEQ ID NO 41
<211> LENGTH: 833
<212> TYPE: PRT
<213> ORGANISM: Artificial Sequence
<220> FEATURE:
<223> OTHER INFORMATION: vaccine polypeptide

<400> SEQUENCE: 41
```

```
Met Gln Ile Phe Val Lys Leu Pro Leu Leu Thr Ile Gly Asp Gln Phe
1               5                   10                  15

Pro Ala Tyr Glu Leu Thr Ala Leu Ile Ala Gly Asp Leu Ser Lys Val
            20                  25                  30

Asp Ala Lys Gln Pro Gly Asp Tyr Phe Thr Thr Val Thr Ser Glu Asp
            35                  40                  45

His Ala Gly Lys Trp Arg Val Phe Phe Trp Pro Lys Asp Phe Thr
    50                  55                  60

Gly Pro Glu Ile Ala Thr Phe Gly Lys Leu Asn Asp Glu Phe Glu Asp
65                  70                  75                  80

Arg Asp Ala Gln Val Leu Gly Val Ser Ile Asp Ser Glu Phe Val His
            85                  90                  95

Phe Asn Trp Arg Ala Gln His Glu Asp Leu Lys Asn Leu Pro Phe Pro
            100                 105                 110

Met Leu Ser Asp Ile Lys Arg Glu Leu Ser Leu Ala Thr Gly Val Leu
            115                 120                 125

Asn Ala Asp Gly Val Ala Asp Arg Ala Thr Phe Ile Val Asp Pro Asn
130                 135                 140

Asn Glu Ile Gln Phe Val Ser Val Thr Ala Gly Ser Val Gly Arg Asn
145                 150                 155                 160

Val Glu Glu Val Leu Arg Val Leu Asp Ala Leu Gln Ser Asp Glu Leu
            165                 170                 175

Cys Ala Cys Asn Trp Arg Lys Gly Asp Pro Thr Leu Asn Ala Thr Glu
            180                 185                 190

Leu Leu Lys Ala Ser Ala Leu Gly Ser Ile Val Gly Gln Thr Tyr Arg
            195                 200                 205

Glu Val Glu Val Val Leu Val Asp Gly Gly Ser Thr Asp Arg Thr Leu
            210                 215                 220

Asp Ile Ala Asn Ser Phe Arg Pro Glu Leu Gly Ser Arg Leu Val Val
225                 230                 235                 240

His Ser Gly Pro Asp Asp Gly Pro Tyr Asp Ala Met Asn Arg Gly Val
            245                 250                 255

Gly Val Ala Thr Gly Glu Trp Val Leu Phe Leu Gly Ala Asp Asp Thr
            260                 265                 270

Leu Tyr Glu Pro Thr Thr Leu Ala Gln Val Ala Ala Phe Leu Gly Asp
            275                 280                 285

His Ala Ala Ser His Leu Val Tyr Gly Asp Val Val Met Arg Ser Thr
            290                 295                 300

Lys Ser Arg His Ala Gly Pro Phe Asp Leu Asp Arg Leu Leu Phe Glu
305                 310                 315                 320

Thr Asn Leu Cys His Gln Ser Ile Phe Tyr Arg Arg Glu Leu Phe Asp
            325                 330                 335

Gly Ile Gly Pro Tyr Asn Leu Arg Tyr Arg Val Trp Ala Asp Trp Asp
            340                 345                 350

Phe Asn Ile Arg Cys Phe Ser Asn Pro Ala Leu Ile Thr Arg Tyr Met
            355                 360                 365

Asp Val Val Ile Ser Glu Tyr Asn Asp Met Thr Gly Phe Ser Met Arg
            370                 375                 380

Gln Gly Thr Asp Lys Glu Phe Arg Lys Arg Leu Pro Met Tyr Phe Trp
385                 390                 395                 400

Val Ala Gly Trp Glu Thr Cys Arg Arg Met Leu Ala Phe Leu Lys Asp
            405                 410                 415

Lys Glu Asn Arg Arg Leu Ala Leu Arg Thr Arg Leu Ile Arg Val Lys
```

```
            420             425             430
Ala Val Ser Lys Glu Arg Ser Ala Glu Pro Arg Ile Arg Arg His Arg
            435             440             445
His Ala Glu Ile Ile Leu Ser Met Pro Gly Phe Gly Val Ile Leu Gly
            450             455             460
Ala Glu Phe Leu Ala Ala Thr Gly Gly Asp Met Ala Ala Phe Ala Ser
465             470             475             480
Ala Asp Arg Leu Ala Gly Val Ala Gly Leu Ala Pro Val Pro Arg Asp
            485             490             495
Ser Gly Arg Ile Ser Gly Asn Leu Lys Arg Pro Arg Arg Tyr Asp Arg
            500             505             510
Arg Leu Leu Arg Ala Cys Val Ser Ile Arg Thr Asp Pro Ser Ser Arg
            515             520             525
Thr Tyr Tyr Asp Arg Lys Arg Thr Glu Gly Lys Arg His Thr Gln Ala
            530             535             540
Val Leu Ala Leu Ala Arg Arg Arg Leu Asn Val Leu Trp Ala Met Leu
545             550             555             560
Arg Asp His Ala Val Tyr His Pro Ala Thr Thr Ala Ala Ala Arg
            565             570             575
Leu Lys Leu Arg Arg Gly Glu Arg Pro Met Ser Leu Gly Gln Val Phe
            580             585             590
Asp Pro Arg Ala Asn Ala Leu His Ser Phe Pro Leu Thr Gly Arg Met
            595             600             605
Pro Trp Ala Pro Phe Ile Val Ser Ser Trp Leu Arg Asn Pro His Pro
            610             615             620
Ala Gln Tyr Phe Thr Ala Arg Cys Leu Arg Ile Leu Pro Gly Leu Trp
625             630             635             640
Ile Gly Ala Gln Gly Gly Ser Ala Ala Lys Leu Leu Met Ser Gly Ala
            645             650             655
Pro Ile Glu Tyr Val Leu Lys Asp Ser Ala Val Trp Met Phe Lys Phe
            660             665             670
Asp Ile Gly Gly Thr Pro Arg Asp Ile Pro Val Ala Gly Ile Trp Asn
            675             680             685
Gly Ser Leu Trp Thr Pro Ala Trp Gly Gly Ile His Ala Ile Ala Ser
            690             695             700
Asn Ala Tyr Gln Phe Arg Asn Val Ile Pro Ala Arg Trp Ser Val Ser
705             710             715             720
Ser Ala Val Leu Pro Asn Tyr Arg Leu Val Ala Ala Leu Pro Met Ala
            725             730             735
Tyr His Asn Gln Arg Met Arg Phe Arg Thr Asp Leu Ser Tyr Gly Val
            740             745             750
Tyr Gly Phe Ala Glu Ile Asn Pro Ile Ala Leu Val Glu Lys Pro Ala
            755             760             765
Leu Ser Trp Lys Ser Arg Leu Arg Arg Lys Asn Ser Ser Ile Ala Leu
            770             775             780
Ala Asn Met Glu Asp Gly Gly Ser Val Gly Arg Ser Asn Asp Ile Pro
785             790             795             800
Gly Arg Arg Ala Arg Phe Ile Gly Glu Lys Ala Glu Asp Pro Pro Ala
            805             810             815
Pro Ser Pro Arg Pro Ala Leu Arg Ile Pro Asn Pro Leu Leu Gly Leu
            820             825             830
Asp
```

```
<210> SEQ ID NO 42
<211> LENGTH: 838
<212> TYPE: PRT
<213> ORGANISM: Artificial Sequence
<220> FEATURE:
<223> OTHER INFORMATION: vaccine polypeptide

<400> SEQUENCE: 42

Met Gln Ile Phe Val Lys Leu Pro Leu Leu Thr Ile Gly Asp Gln Phe
1               5                   10                  15

Pro Ala Tyr Glu Leu Thr Ala Leu Ile Ala Gly Asp Leu Ser Lys Val
            20                  25                  30

Asp Ala Lys Gln Pro Gly Asp Tyr Phe Thr Thr Val Thr Ser Glu Asp
        35                  40                  45

His Ala Gly Lys Trp Arg Val Val Phe Phe Trp Pro Lys Asp Phe Thr
    50                  55                  60

Gly Pro Glu Ile Ala Thr Phe Gly Lys Leu Asn Asp Glu Phe Glu Asp
65                  70                  75                  80

Arg Asp Ala Gln Val Leu Gly Val Ser Ile Asp Ser Glu Phe Val His
                85                  90                  95

Phe Asn Trp Arg Ala Gln His Glu Asp Leu Lys Asn Leu Pro Phe Pro
            100                 105                 110

Met Leu Ser Asp Ile Lys Arg Glu Leu Ser Leu Ala Thr Gly Val Leu
        115                 120                 125

Asn Ala Asp Gly Val Ala Asp Arg Ala Thr Phe Ile Val Asp Pro Asn
    130                 135                 140

Asn Glu Ile Gln Phe Val Ser Val Thr Ala Gly Ser Val Gly Arg Asn
145                 150                 155                 160

Val Glu Glu Val Leu Arg Val Leu Asp Ala Leu Gln Ser Asp Glu Leu
                165                 170                 175

Cys Ala Cys Asn Trp Arg Lys Gly Asp Pro Thr Leu Asn Ala Thr Glu
            180                 185                 190

Leu Leu Lys Ala Ser Ala Leu Gly Ser Ile Val Gly Gln Thr Tyr Arg
        195                 200                 205

Glu Val Glu Val Val Leu Val Asp Gly Gly Ser Thr Asp Arg Thr Leu
    210                 215                 220

Asp Ile Ala Asn Ser Phe Arg Pro Glu Leu Gly Ser Arg Leu Val Val
225                 230                 235                 240

His Ser Gly Pro Asp Asp Gly Pro Tyr Asp Ala Met Asn Arg Gly Val
                245                 250                 255

Gly Val Ala Thr Gly Glu Trp Val Leu Phe Leu Gly Ala Asp Asp Thr
            260                 265                 270

Leu Tyr Glu Pro Thr Thr Leu Ala Gln Val Ala Ala Phe Leu Gly Asp
        275                 280                 285

His Ala Ala Ser His Leu Val Tyr Gly Asp Val Val Met Arg Ser Thr
    290                 295                 300

Lys Ser Arg His Ala Gly Pro Phe Asp Leu Asp Arg Leu Leu Phe Glu
305                 310                 315                 320

Thr Asn Leu Cys His Gln Ser Ile Phe Tyr Arg Arg Glu Leu Phe Asp
                325                 330                 335

Gly Ile Gly Pro Tyr Asn Leu Arg Tyr Arg Val Trp Ala Asp Trp Asp
            340                 345                 350

Phe Asn Ile Arg Cys Phe Ser Asn Pro Ala Leu Ile Thr Arg Tyr Met
        355                 360                 365
```

```
Asp Val Val Ile Ser Glu Tyr Asn Asp Met Thr Gly Phe Ser Met Arg
    370                 375                 380

Gln Gly Thr Asp Lys Glu Phe Arg Lys Arg Leu Pro Met Tyr Phe Trp
385                 390                 395                 400

Val Ala Gly Trp Glu Thr Cys Arg Arg Met Leu Ala Phe Leu Lys Asp
                405                 410                 415

Lys Glu Asn Arg Arg Leu Ala Leu Arg Thr Arg Leu Ile Arg Val Lys
                420                 425                 430

Ala Val Ser Lys Glu Arg Ser Ala Glu Pro Arg Ile Arg His Arg
            435                 440                 445

His Ala Glu Ile Ile Leu Ser Met Pro Gly Phe Gly Val Ile Leu Gly
    450                 455                 460

Ala Glu Phe Leu Ala Ala Thr Gly Gly Asp Met Ala Ala Phe Ala Ser
465                 470                 475                 480

Ala Asp Arg Leu Ala Gly Val Ala Gly Leu Ala Pro Val Pro Arg Asp
                485                 490                 495

Ser Gly Arg Ile Ser Gly Asn Leu Lys Arg Pro Arg Arg Tyr Asp Arg
                500                 505                 510

Arg Leu Leu Arg Ala Cys Tyr Leu Ser Ala Leu Val Ser Ile Arg Thr
    515                 520                 525

Asp Pro Ser Ser Arg Thr Tyr Tyr Asp Arg Lys Arg Thr Glu Gly Lys
    530                 535                 540

Arg His Thr Gln Ala Val Leu Ala Leu Ala Arg Arg Leu Asn Val
545                 550                 555                 560

Leu Trp Ala Met Leu Arg Asp His Ala Val Tyr His Pro Ala Thr Thr
                565                 570                 575

Thr Ala Ala Arg Leu Lys Leu Arg Arg Gly Glu Arg Pro Met Ser
                580                 585                 590

Leu Gly Gln Val Phe Asp Pro Arg Ala Asn Ala Leu His Ser Phe Pro
    595                 600                 605

Leu Thr Gly Arg Met Pro Trp Ala Pro Phe Ile Val Ser Ser Trp Leu
    610                 615                 620

Arg Asn Pro His Pro Ala Gln Tyr Phe Thr Ala Arg Cys Leu Arg Ile
625                 630                 635                 640

Leu Pro Gly Leu Trp Ile Gly Ala Gln Gly Gly Ser Ala Ala Lys Leu
                645                 650                 655

Leu Met Ser Gly Ala Pro Ile Glu Tyr Val Leu Lys Asp Ser Ala Val
                660                 665                 670

Trp Met Phe Lys Phe Asp Ile Gly Gly Thr Pro Arg Asp Ile Pro Val
                675                 680                 685

Ala Gly Ile Trp Asn Gly Ser Leu Trp Thr Pro Ala Trp Gly Gly Ile
                690                 695                 700

His Ala Ile Ala Ser Asn Ala Tyr Gln Phe Arg Asn Val Ile Pro Ala
705                 710                 715                 720

Arg Trp Ser Val Ser Ser Ala Val Leu Pro Asn Tyr Arg Leu Val Ala
                725                 730                 735

Ala Leu Pro Met Ala Tyr His Asn Gln Arg Met Arg Phe Arg Thr Asp
                740                 745                 750

Leu Ser Tyr Gly Val Tyr Gly Phe Ala Glu Ile Asn Pro Ile Ala Leu
            755                 760                 765

Val Glu Lys Pro Ala Leu Ser Trp Lys Ser Arg Leu Arg Arg Lys Asn
770                 775                 780

Ser Ser Ile Ala Leu Ala Asn Met Glu Asp Gly Gly Ser Val Gly Arg
```

```
                785                 790                 795                 800
Ser Asn Asp Ile Pro Gly Arg Arg Ala Arg Phe Ile Gly Glu Lys Ala
                    805                 810                 815

Glu Asp Pro Pro Ala Pro Ser Pro Arg Pro Ala Leu Arg Ile Pro Asn
                820                 825                 830

Pro Leu Leu Gly Leu Asp
            835

<210> SEQ ID NO 43
<211> LENGTH: 406
<212> TYPE: PRT
<213> ORGANISM: Mycobacterium avium paratuberculosis

<400> SEQUENCE: 43

Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Ala
                20                  25                  30

Gln Arg Leu Leu Ser Gln Arg Val Ala Asn Asp Glu Ala Ala Leu Leu
                35                  40                  45

Glu Leu Ile Ala Ala Val Thr Thr Leu Ala Asp Gly Gly Glu Val Thr
50                      55                  60

Trp Ala Ile Asp Leu Asn Ala Gly Gly Ala Ala Leu Leu Ile Ala Leu
65                  70                  75                  80

Leu Ile Ala Ala Gly Gln Arg Leu Leu Tyr Ile Pro Gly Arg Thr Val
                    85                  90                  95

His His Ala Ala Gly Ser Tyr Arg Gly Glu Gly Lys Thr Asp Ala Lys
                100                 105                 110

Asp Ala Ala Ile Ile Ala Asp Gln Ala Arg Met Arg His Asp Leu Gln
                115                 120                 125

Pro Leu Arg Ala Gly Asp Asp Ile Ala Val Glu Leu Arg Ile Leu Thr
                130                 135                 140

Ser Arg Arg Ser Asp Leu Val Ala Asp Arg Thr Arg Ala Ile Asn Arg
145                 150                 155                 160

Met Arg Ala Gln Leu Leu Glu Tyr Phe Pro Ala Leu Glu Arg Ala Phe
                165                 170                 175

Asp Tyr Asn Lys Ser Arg Ala Ala Leu Ile Leu Leu Thr Gly Tyr Gln
                180                 185                 190

Thr Pro Asp Ala Leu Arg Ser Ala Gly Gly Ala Arg Val Ala Ala Phe
                195                 200                 205

Leu Arg Lys Arg Lys Ala Arg Asn Ala Asp Thr Val Ala Ala Thr Ala
210                 215                 220

Leu Gln Ala Ala Asn Ala Gln His Ser Ile Val Pro Gly Gln Gln Leu
225                 230                 235                 240

Ala Ala Thr Val Val Ala Arg Leu Ala Lys Glu Val Met Ala Leu Asp
                245                 250                 255

Thr Glu Ile Gly Asp Thr Asp Ala Met Ile Glu Glu Arg Phe Arg Arg
                260                 265                 270

His Arg His Ala Glu Ile Ile Leu Ser Met Pro Gly Phe Gly Val Ile
                275                 280                 285

Leu Gly Ala Glu Phe Leu Ala Ala Thr Gly Gly Asp Met Ala Ala Phe
            290                 295                 300

Ala Ser Ala Asp Arg Leu Ala Gly Val Ala Gly Leu Ala Pro Val Pro
305                 310                 315                 320
```

```
Arg Asp Ser Gly Arg Ile Ser Gly Asn Leu Lys Arg Pro Arg Tyr
            325                 330                 335

Asp Arg Arg Leu Leu Arg Ala Cys Tyr Leu Ser Ala Leu Val Ser Ile
            340                 345                 350

Arg Thr Asp Pro Ser Ser Arg Thr Tyr Tyr Asp Arg Lys Arg Thr Glu
            355                 360                 365

Gly Lys Arg His Thr Gln Ala Val Leu Ala Leu Ala Arg Arg Leu
    370                 375                 380

Asn Val Leu Trp Ala Met Leu Arg Asp His Ala Val Tyr His Pro Ala
385                 390                 395                 400

Thr Thr Thr Ala Ala Ala
                405

<210> SEQ ID NO 44
<211> LENGTH: 10
<212> TYPE: PRT
<213> ORGANISM: Mycobacterium avium paratuberculosis

<400> SEQUENCE: 44

Val Ser Ile Arg Thr Asp Pro Ser Ser Arg
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Phosphorylated A4 peptide
<220> FEATURE:
<221> NAME/KEY: MOD_RES
<222> LOCATION: (8)..(8)
<223> OTHER INFORMATION: PHOSPHORYLATION

<400> SEQUENCE: 45

Val Ser Ile Arg Thr Asp Pro Ser Ser Arg
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Phosphorylated A4 peptide
<220> FEATURE:
<221> NAME/KEY: MOD_RES
<222> LOCATION: (9)..(9)
<223> OTHER INFORMATION: PHOSPHORYLATION

<400> SEQUENCE: 46

Val Ser Ile Arg Thr Asp Pro Ser Ser Arg
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Phosphorylated A4 peptide
<220> FEATURE:
<221> NAME/KEY: MOD_RES
<222> LOCATION: (8)..(9)
<223> OTHER INFORMATION: PHOSPHORYLATION

<400> SEQUENCE: 47

Val Ser Ile Arg Thr Asp Pro Ser Ser Arg
1               5                   10
```

<210> SEQ ID NO 48
<211> LENGTH: 10
<212> TYPE: PRT
<213> ORGANISM: Mycobacterium avium paratuberculosis

<400> SEQUENCE: 48

Asn Leu Lys Arg Pro Arg Arg Tyr Asp Arg
1               5                   10

<210> SEQ ID NO 49
<211> LENGTH: 2522
<212> TYPE: DNA
<213> ORGANISM: Artificial Sequence
<220> FEATURE:
<223> OTHER INFORMATION: vaccine polynucleotide sequence

<400> SEQUENCE: 49

```
atgcagatct tcgtcaaact gccccttctc actatcggag accagttccc cgcttacgaa      60
cttacagctc ttatcgctgg agatctgagt aaggttgacg ccaaacagcc cggcgattat     120
ttcactaccg ttaccagtga ggatcacgca ggtaaatgga gagtcgtctt cttctggcct     180
aaagacttca cctttgtgtg ccctactgag atcgcaacat tcgggaagct gaacgatgag     240
ttcgaagatc gagacgcaca ggttttgggc gtgtctatcg attccgagtt cgtgcacttc     300
aactggagag cacagcatga agatctcaag aaccttccat tccccatgct cagcgacatc     360
aagagagaac tgagcttggc aacaggtgtt ctgaatgctg atggcgttgc tgacagagca     420
acattcattg ttgaccccaa taacgagatc cagttcgttt ccgttactgc tggttctgtc     480
ggtagaaacg ttgaagaggt cctgagagtt ctcgacgcac ttcagagtga tgaactgtgt     540
gcctgcaatt ggcggaaagg agatcctact ctcaatgcca cagagctgct aaagcaagt     600
gctctcggat ccattgtcgg acagacctat agagaggtgg aagttgtcct ggtcgatggt     660
ggatctacag ataggactct cgacattgcc aactccttta gaccagagct cggttcaagg     720
ctcgttgttc attctggacc agatgatgga ccatacgacg ccatgaacag aggtgttgga     780
gttgctacag gagaatgggt cttgttcctt ggagctgatg acactctgta cgaaccgact     840
acattggctc aggttgcagc attttttggga gatcatgcag cttctcacct tgtgtacgga     900
gatgtggtca tgagatccac caagtccaga catgctggac cattcgatct tgacagactc     960
ctgttcgaga ccaacctctg tcatcagagc atcttctaca cgggaact cttcgacgga    1020
attggaccttt acaacctcag gtacaggggtt tgggcagact gggatttcaa catcaggtgc    1080
ttctcgaacc cagctttgat cacacggtac atggatgttg tgatctccga gtacaacgat    1140
atgaccggct ctccatgag acagggaacc gacaaagagt tcaggaagcg cttgccaatg    1200
tacttctggg ttgctggatg ggaaacatgt cggagaatgc ttgctttcct gaaggacaag    1260
gagaacagga gacttgctct caggactaga ctcatcaggg tcaaagcagt gtccaaggaa    1320
aggagtgctg aacctagaat tcggagacat agacatgcag agatcatcct gagcatgcct    1380
ggatttggcg ttatcctcgg agctgaattt cttgcagcaa caggaggtga tatggcagct    1440
ttcgcatcag ctgacagatt ggctggagtt gcaggtttgg ctccagttcc aagagattca    1500
gggagaatca gcggtaacct caagagacct agacgctacg acagaagact gcttagagcc    1560
tgctatctga gtgctttggt tagcattaga accgacccct ctagtcgaac ctactacgat    1620
aggaagcgga ctgaaggtaa agacataccc aggcagtgt tggcacttgc tagaagacgg    1680
cttaatgttc tgtgggctat gctgagagat catgccgtgt accatcctgc taccacaaca    1740
```

```
gctgctgcta gacttaagct tcgcagaggt gagagaccta tgagtcttgg ccaggtcttt    1800
gatcctagag ctaatgcact gcactctttc cctcttacag gacgcatgcc ttgggctcca    1860
tttatcgtta gttcctggct cagaaaccct catccagctc agtacttcac agccagatgt    1920
ctcagaatcc ttcctggtct ttggattgga gcacagggtg gttccgcagc taagctgttg    1980
atgagtggtg caccaatcga atacgtcctg aaagactcag cagtgtggat gttcaagttc    2040
gacattggag gaacaccaag ggatattcct gtcgctggta tctggaatgg aagtttgtgg    2100
accccagcat ggggaggtat tcatgctatc gcttccaacg cttaccagtt ccgaaatgtg    2160
atccctgcaa gatggtctgt gagttcagcc gtgttgccaa actatagact tgttgctgct    2220
ctccccatgg cctaccataa tcagcgaatg aggtttcgga cagatctgtc ctatggtgtg    2280
tacgggttcg ctgaaatcaa tcccatcgct ctggttgaga aacctgccct gtcttggaaa    2340
tccagactga gacggaagaa ctcttccatc gctctcgcaa acatggaaga tggtggtagt    2400
gttggaagga gtaacgacat ccctgggagg agggctagta ttattggtga aaagccgaa    2460 gatcctcctg ctccatctcc tagacccgcc ttgaggattc caaaccctct tctcggtctt    2520
ga                                                                   2522
```

<210> SEQ ID NO 50
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 50

Val Asp Ala Gly Lys Ala Asp His Tyr
1               5

<210> SEQ ID NO 51
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 51

Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Asp Ala
                20                  25                  30

Gln Arg Leu Leu Ser Gln Arg Val Ala Asn Asp Glu Ala Leu Leu
        35                  40                  45

Glu Leu Ile Ala Ala Val Thr Thr Leu Ala Asp Gly Gly Glu Val Thr
    50                  55                  60

Trp Ala Ile Asp
65

<210> SEQ ID NO 52
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 52

Met Val Ile Asn Asp Asp Ala Gln Arg Leu Leu Ser Gln Arg Val Asp
1               5                   10                  15

```
Ala Gly Lys Ala Asp His Tyr Ala Val Thr Thr Leu Ala Asp Gly Gly
                20                  25                  30

Glu Val Thr Trp Ala Ile Asp
        35
```

<210> SEQ ID NO 53
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 53

```
Leu Asn Ala Gly Gly Ala Ala Leu Leu Ile Ala Leu Leu Ile Ala Ala
1               5                   10                  15

Gly Gln Arg Leu Leu Tyr
            20
```

<210> SEQ ID NO 54
<211> LENGTH: 16
<212> TYPE: PRT
<213> ORGANISM: Artificial Sequence
<220> FEATURE:
<223> OTHER INFORMATION: Synthetic peptide

<400> SEQUENCE: 54

```
Ile Pro Gly Arg Thr Val His His Ala Ala Gly Ser Tyr Arg Gly Glu
1               5                   10                  15
```

<210> SEQ ID NO 55
<211> LENGTH: 16
<212> TYPE: PRT
<213> ORGANISM: Artificial Sequence
<220> FEATURE:
<223> OTHER INFORMATION: Synthetic peptide

<400> SEQUENCE: 55

```
Ile Pro Gly Ala Thr Val His His Ala Ala Gly Ser Tyr Arg Gly Glu
1               5                   10                  15
```

<210> SEQ ID NO 56
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 56

```
Leu Asn Ala Gly Gly Ala Ala Leu Leu Ile Ala Leu Leu Ile Ala Ala
1               5                   10                  15

Gly Gln Arg Leu Leu Tyr Ile Pro Gly Arg Thr Val His His Ala Ala
            20                  25                  30

Gly Ser Tyr Arg Gly Glu
        35
```

<210> SEQ ID NO 57
<211> LENGTH: 38
<212> TYPE: PRT
<213> ORGANISM: Artificial Sequence
<220> FEATURE:
<223> OTHER INFORMATION: Synthetic polypeptide

<400> SEQUENCE: 57

```
Leu Asn Ala Gly Gly Ala Ala Leu Leu Ile Ala Leu Leu Ile Ala Ala
```

```
                1               5                  10                  15
Gly Gln Arg Leu Leu Tyr Ile Pro Gly Ala Thr Val His His Ala Ala
                    20                  25                  30

Gly Ser Tyr Arg Gly Glu
            35
```

<210> SEQ ID NO 58
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 58

```
Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Asp Ala
                    20                  25                  30

Gln Arg Leu Leu Ser Gln Arg Val Ala Asn Asp Glu Ala Ala Leu Leu
                35                  40                  45

Glu Leu Ile Ala Ala Val Thr Thr Leu Ala Asp Gly Gly Glu Val Thr
    50                  55                  60

Trp Ala Ile Asp Leu Asn Ala Gly Ala Ala Leu Leu Ile Ala Leu
65                  70                  75                  80

Leu Ile Ala Ala Gly Gln Arg Leu Leu Tyr Ile Pro Gly Arg Thr Val
                    85                  90                  95

His His Ala Ala Gly Ser Tyr Arg Gly Glu
                100                 105
```

<210> SEQ ID NO 59
<211> LENGTH: 106
<212> TYPE: PRT
<213> ORGANISM: Artificial Sequence
<220> FEATURE:
<223> OTHER INFORMATION: Synthetic polypeptide

<400> SEQUENCE: 59

```
Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Asp Ala
                    20                  25                  30

Gln Arg Leu Leu Ser Gln Arg Val Ala Asn Asp Glu Ala Ala Leu Leu
                35                  40                  45

Glu Leu Ile Ala Ala Val Thr Thr Leu Ala Asp Gly Gly Glu Val Thr
    50                  55                  60

Trp Ala Ile Asp Leu Asn Ala Gly Ala Ala Leu Leu Ile Ala Leu
65                  70                  75                  80

Leu Ile Ala Ala Gly Gln Arg Leu Leu Tyr Ile Pro Gly Ala Thr Val
                    85                  90                  95

His His Ala Ala Gly Ser Tyr Arg Gly Glu
                100                 105
```

<210> SEQ ID NO 60
<211> LENGTH: 77
<212> TYPE: PRT
<213> ORGANISM: Artificial Sequence
<220> FEATURE:
<223> OTHER INFORMATION: Synthetic polypeptide

<400> SEQUENCE: 60

```
Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
            20                  25                  30

Glu Val Thr Trp Ala Ile Asp Leu Asn Ala Gly Gly Ala Ala Leu Leu
        35                  40                  45

Ile Ala Leu Leu Ile Ala Ala Gly Gln Arg Leu Leu Tyr Ile Pro Gly
    50                  55                  60

Arg Thr Val His His Ala Ala Gly Ser Tyr Arg Gly Glu
65                  70                  75

<210> SEQ ID NO 61
<211> LENGTH: 77
<212> TYPE: PRT
<213> ORGANISM: Artificial Sequence
<220> FEATURE:
<223> OTHER INFORMATION: Synthetic polypeptide

<400> SEQUENCE: 61

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
            20                  25                  30

Glu Val Thr Trp Ala Ile Asp Leu Asn Ala Gly Gly Ala Ala Leu Leu
        35                  40                  45

Ile Ala Leu Leu Ile Ala Ala Gly Gln Arg Leu Leu Tyr Ile Pro Gly
    50                  55                  60

Ala Thr Val His His Ala Ala Gly Ser Tyr Arg Gly Glu
65                  70                  75

<210> SEQ ID NO 62
<211> LENGTH: 968
<212> TYPE: PRT
<213> ORGANISM: Artificial Sequence
<220> FEATURE:
<223> OTHER INFORMATION: Vaccine polypeptide

<400> SEQUENCE: 62

Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Asp Ala
            20                  25                  30

Gln Arg Leu Leu Ser Gln Arg Val Ala Asn Asp Glu Ala Ala Leu Leu
            35                  40                  45

Glu Leu Ile Ala Ala Val Thr Thr Leu Ala Asp Gly Gly Glu Val Thr
    50                  55                  60

Trp Ala Ile Asp Leu Asn Ala Gly Gly Ala Ala Leu Leu Ile Ala Leu
65                  70                  75                  80

Leu Ile Ala Ala Gly Gln Arg Leu Leu Tyr Ile Pro Gly Ala Thr Val
            85                  90                  95

His His Ala Ala Gly Ser Tyr Arg Gly Glu Ala Pro Val Lys Gln Thr
                100                 105                 110

Leu Asn Phe Asp Leu Leu Lys Leu Ala Gly Asp Val Glu Ser Asn Pro
            115                 120                 125

Gly Pro Met Gln Ile Phe Val Lys Leu Pro Leu Leu Thr Ile Gly Asp
        130                 135                 140

Gln Phe Pro Ala Tyr Glu Leu Thr Ala Leu Ile Ala Gly Asp Leu Ser
```

-continued

```
            145                 150                 155                 160
Lys Val Asp Ala Lys Gln Pro Gly Asp Tyr Phe Thr Thr Val Thr Ser
                    165                 170                 175
Glu Asp His Ala Gly Lys Trp Arg Val Val Phe Phe Trp Pro Lys Asp
                180                 185                 190
Phe Thr Gly Pro Glu Ile Ala Thr Phe Gly Lys Leu Asn Asp Glu Phe
            195                 200                 205
Glu Asp Arg Asp Ala Gln Val Leu Gly Val Ser Ile Asp Ser Glu Phe
        210                 215                 220
Val His Phe Asn Trp Arg Ala Gln His Glu Asp Leu Lys Asn Leu Pro
225                 230                 235                 240
Phe Pro Met Leu Ser Asp Ile Lys Arg Glu Leu Ser Leu Ala Thr Gly
                245                 250                 255
Val Leu Asn Ala Asp Gly Val Ala Asp Arg Ala Thr Phe Ile Val Asp
                260                 265                 270
Pro Asn Asn Glu Ile Gln Phe Val Ser Val Thr Ala Gly Ser Val Gly
            275                 280                 285
Arg Asn Val Glu Glu Val Leu Arg Val Leu Asp Ala Leu Gln Ser Asp
        290                 295                 300
Glu Leu Cys Ala Cys Asn Trp Arg Lys Gly Asp Pro Thr Leu Asn Ala
305                 310                 315                 320
Thr Glu Leu Leu Lys Ala Ser Ala Leu Gly Ser Ile Val Gly Gln Thr
                325                 330                 335
Tyr Arg Glu Val Glu Val Val Leu Val Asp Gly Gly Ser Thr Asp Arg
                340                 345                 350
Thr Leu Asp Ile Ala Asn Ser Phe Arg Pro Glu Leu Gly Ser Arg Leu
            355                 360                 365
Val Val His Ser Gly Pro Asp Asp Gly Pro Tyr Asp Ala Met Asn Arg
        370                 375                 380
Gly Val Gly Val Ala Thr Gly Glu Trp Val Leu Phe Leu Gly Ala Asp
385                 390                 395                 400
Asp Thr Leu Tyr Glu Pro Thr Thr Leu Ala Gln Val Ala Ala Phe Leu
                405                 410                 415
Gly Asp His Ala Ala Ser His Leu Val Tyr Gly Asp Val Val Met Arg
                420                 425                 430
Ser Thr Lys Ser Arg His Ala Gly Pro Phe Asp Leu Asp Arg Leu Leu
            435                 440                 445
Phe Glu Thr Asn Leu Cys His Gln Ser Ile Phe Tyr Arg Arg Glu Leu
        450                 455                 460
Phe Asp Gly Ile Gly Pro Tyr Asn Leu Arg Tyr Arg Val Trp Ala Asp
465                 470                 475                 480
Trp Asp Phe Asn Ile Arg Cys Phe Ser Asn Pro Ala Leu Ile Thr Arg
                485                 490                 495
Tyr Met Asp Val Val Ile Ser Glu Tyr Asn Asp Met Thr Gly Phe Ser
                500                 505                 510
Met Arg Gln Gly Thr Asp Lys Glu Phe Arg Lys Arg Leu Pro Met Tyr
            515                 520                 525
Phe Trp Val Ala Gly Trp Glu Thr Cys Arg Arg Met Leu Ala Phe Leu
        530                 535                 540
Lys Asp Lys Glu Asn Arg Arg Leu Ala Leu Thr Arg Leu Ile Arg
545                 550                 555                 560
Val Lys Ala Val Ser Lys Glu Arg Ser Ala Glu Pro Arg Ile Arg Arg
                565                 570                 575
```

His Arg His Ala Glu Ile Ile Leu Ser Met Pro Gly Phe Gly Val Ile
            580                 585                 590

Leu Gly Ala Glu Phe Leu Ala Ala Thr Gly Gly Asp Met Ala Ala Phe
        595                 600                 605

Ala Ser Ala Asp Arg Leu Ala Gly Val Ala Gly Leu Ala Pro Val Pro
610                 615                 620

Arg Asp Ser Gly Arg Ile Ser Gly Asn Leu Lys Arg Pro Arg Arg Tyr
625                 630                 635                 640

Asp Arg Arg Leu Leu Arg Ala Cys Tyr Leu Ser Ala Leu Val Ser Ile
            645                 650                 655

Arg Thr Asp Pro Ser Ser Arg Thr Tyr Tyr Asp Arg Lys Arg Thr Glu
            660                 665                 670

Gly Lys Arg His Thr Gln Ala Val Leu Ala Leu Ala Arg Arg Arg Leu
        675                 680                 685

Asn Val Leu Trp Ala Met Leu Arg Asp His Ala Val Tyr His Pro Ala
    690                 695                 700

Thr Thr Thr Ala Ala Ala Arg Leu Lys Leu Arg Arg Gly Glu Arg Pro
705                 710                 715                 720

Met Ser Leu Gly Gln Val Phe Asp Pro Arg Ala Asn Ala Leu His Ser
            725                 730                 735

Phe Pro Leu Thr Gly Arg Met Pro Trp Ala Pro Phe Ile Val Ser Ser
            740                 745                 750

Trp Leu Arg Asn Pro His Pro Ala Gln Tyr Phe Thr Ala Arg Cys Leu
        755                 760                 765

Arg Ile Leu Pro Gly Leu Trp Ile Gly Ala Gln Gly Gly Ser Ala Ala
    770                 775                 780

Lys Leu Leu Met Ser Gly Ala Pro Ile Glu Tyr Val Leu Lys Asp Ser
785                 790                 795                 800

Ala Val Trp Met Phe Lys Phe Asp Ile Gly Gly Thr Pro Arg Asp Ile
            805                 810                 815

Pro Val Ala Gly Ile Trp Asn Gly Ser Leu Trp Thr Pro Ala Trp Gly
            820                 825                 830

Gly Ile His Ala Ile Ala Ser Asn Ala Tyr Gln Phe Arg Asn Val Ile
        835                 840                 845

Pro Ala Arg Trp Ser Val Ser Ser Ala Val Leu Pro Asn Tyr Arg Leu
    850                 855                 860

Val Ala Ala Leu Pro Met Ala Tyr His Asn Gln Arg Met Arg Phe Arg
865                 870                 875                 880

Thr Asp Leu Ser Tyr Gly Val Tyr Gly Phe Ala Glu Ile Asn Pro Ile
            885                 890                 895

Ala Leu Val Glu Lys Pro Ala Leu Ser Trp Lys Ser Arg Leu Arg Arg
        900                 905                 910

Lys Asn Ser Ser Ile Ala Leu Ala Asn Met Glu Asp Gly Gly Ser Val
    915                 920                 925

Gly Arg Ser Asn Asp Ile Pro Gly Arg Arg Ala Arg Phe Ile Gly Glu
    930                 935                 940

Lys Ala Glu Asp Pro Pro Ala Pro Ser Pro Arg Pro Ala Leu Arg Ile
945                 950                 955                 960

Pro Asn Pro Leu Leu Gly Leu Asp
            965

<210> SEQ ID NO 63
<211> LENGTH: 963

<212> TYPE: PRT
<213> ORGANISM: Artificial Sequence
<220> FEATURE:
<223> OTHER INFORMATION: Vaccine polypeptide

<400> SEQUENCE: 63

Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Ala
            20                  25                  30

Gln Arg Leu Leu Ser Gln Arg Val Ala Asn Asp Glu Ala Ala Leu Leu
        35                  40                  45

Glu Leu Ile Ala Ala Val Thr Thr Leu Ala Asp Gly Gly Glu Val Thr
    50                  55                  60

Trp Ala Ile Asp Leu Asn Ala Gly Gly Ala Ala Leu Leu Ile Ala Leu
65                  70                  75                  80

Leu Ile Ala Ala Gly Gln Arg Leu Leu Tyr Ile Pro Gly Ala Thr Val
                85                  90                  95

His His Ala Ala Gly Ser Tyr Arg Gly Glu Ala Pro Val Lys Gln Thr
            100                 105                 110

Leu Asn Phe Asp Leu Leu Lys Leu Ala Gly Asp Val Glu Ser Asn Pro
        115                 120                 125

Gly Pro Met Gln Ile Phe Val Lys Leu Pro Leu Leu Thr Ile Gly Asp
    130                 135                 140

Gln Phe Pro Ala Tyr Glu Leu Thr Ala Leu Ile Ala Gly Asp Leu Ser
145                 150                 155                 160

Lys Val Asp Ala Lys Gln Pro Gly Asp Tyr Phe Thr Thr Val Thr Ser
                165                 170                 175

Glu Asp His Ala Gly Lys Trp Arg Val Val Phe Phe Trp Pro Lys Asp
            180                 185                 190

Phe Thr Gly Pro Glu Ile Ala Thr Phe Gly Lys Leu Asn Asp Glu Phe
        195                 200                 205

Glu Asp Arg Asp Ala Gln Val Leu Gly Val Ser Ile Asp Ser Glu Phe
    210                 215                 220

Val His Phe Asn Trp Arg Ala Gln His Glu Asp Leu Lys Asn Leu Pro
225                 230                 235                 240

Phe Pro Met Leu Ser Asp Ile Lys Arg Glu Leu Ser Leu Ala Thr Gly
                245                 250                 255

Val Leu Asn Ala Asp Gly Val Ala Asp Arg Ala Thr Phe Ile Val Asp
            260                 265                 270

Pro Asn Asn Glu Ile Gln Phe Val Ser Val Thr Ala Gly Ser Val Gly
        275                 280                 285

Arg Asn Val Glu Glu Val Leu Arg Val Leu Asp Ala Leu Gln Ser Asp
    290                 295                 300

Glu Leu Cys Ala Cys Asn Trp Arg Lys Gly Asp Pro Thr Leu Asn Ala
305                 310                 315                 320

Thr Glu Leu Leu Lys Ala Ser Ala Leu Gly Ser Ile Val Gly Gln Thr
                325                 330                 335

Tyr Arg Glu Val Glu Val Leu Val Asp Gly Gly Ser Thr Asp Arg
            340                 345                 350

Thr Leu Asp Ile Ala Asn Ser Phe Arg Pro Glu Leu Gly Ser Arg Leu
        355                 360                 365

Val Val His Ser Gly Pro Asp Asp Gly Pro Tyr Asp Ala Met Asn Arg
    370                 375                 380

```
Gly Val Gly Val Ala Thr Gly Glu Trp Val Leu Phe Leu Gly Ala Asp
385                 390                 395                 400

Asp Thr Leu Tyr Glu Pro Thr Thr Leu Ala Gln Val Ala Ala Phe Leu
                405                 410                 415

Gly Asp His Ala Ala Ser His Leu Val Tyr Gly Asp Val Val Met Arg
            420                 425                 430

Ser Thr Lys Ser Arg His Ala Gly Pro Phe Asp Leu Asp Arg Leu Leu
        435                 440                 445

Phe Glu Thr Asn Leu Cys His Gln Ser Ile Phe Tyr Arg Arg Glu Leu
    450                 455                 460

Phe Asp Gly Ile Gly Pro Tyr Asn Leu Arg Tyr Arg Val Trp Ala Asp
465                 470                 475                 480

Trp Asp Phe Asn Ile Arg Cys Phe Ser Asn Pro Ala Leu Ile Thr Arg
                485                 490                 495

Tyr Met Asp Val Val Ile Ser Glu Tyr Asn Asp Met Thr Gly Phe Ser
            500                 505                 510

Met Arg Gln Gly Thr Asp Lys Glu Phe Arg Lys Arg Leu Pro Met Tyr
        515                 520                 525

Phe Trp Val Ala Gly Trp Glu Thr Cys Arg Arg Met Leu Ala Phe Leu
    530                 535                 540

Lys Asp Lys Glu Asn Arg Arg Leu Ala Leu Arg Thr Arg Leu Ile Arg
545                 550                 555                 560

Val Lys Ala Val Ser Lys Glu Arg Ser Ala Glu Pro Arg Ile Arg Arg
                565                 570                 575

His Arg His Ala Glu Ile Ile Leu Ser Met Pro Gly Phe Gly Val Ile
            580                 585                 590

Leu Gly Ala Glu Phe Leu Ala Ala Thr Gly Gly Asp Met Ala Ala Phe
        595                 600                 605

Ala Ser Ala Asp Arg Leu Ala Gly Val Ala Gly Leu Ala Pro Val Pro
    610                 615                 620

Arg Asp Ser Gly Arg Ile Ser Gly Asn Leu Lys Arg Pro Arg Arg Tyr
625                 630                 635                 640

Asp Arg Arg Leu Leu Arg Ala Cys Val Ser Ile Arg Thr Asp Pro Ser
                645                 650                 655

Ser Arg Thr Tyr Tyr Asp Arg Lys Arg Thr Glu Gly Lys Arg His Thr
            660                 665                 670

Gln Ala Val Leu Ala Leu Ala Arg Arg Leu Asn Val Leu Trp Ala
        675                 680                 685

Met Leu Arg Asp His Ala Val Tyr His Pro Ala Thr Thr Thr Ala Ala
    690                 695                 700

Ala Arg Leu Lys Leu Arg Arg Gly Glu Arg Pro Met Ser Leu Gly Gln
705                 710                 715                 720

Val Phe Asp Pro Arg Ala Asn Ala Leu His Ser Phe Pro Leu Thr Gly
                725                 730                 735

Arg Met Pro Trp Ala Pro Phe Ile Val Ser Ser Trp Leu Arg Asn Pro
            740                 745                 750

His Pro Ala Gln Tyr Phe Thr Ala Arg Cys Leu Arg Ile Leu Pro Gly
        755                 760                 765

Leu Trp Ile Gly Ala Gln Gly Gly Ser Ala Ala Lys Leu Leu Met Ser
    770                 775                 780

Gly Ala Pro Ile Glu Tyr Val Leu Lys Asp Ser Ala Val Trp Met Phe
785                 790                 795                 800

Lys Phe Asp Ile Gly Gly Thr Pro Arg Asp Ile Pro Val Ala Gly Ile
```

-continued

```
                    805                 810                 815

Trp Asn Gly Ser Leu Trp Thr Pro Ala Trp Gly Gly Ile His Ala Ile
            820                 825                 830

Ala Ser Asn Ala Tyr Gln Phe Arg Asn Val Ile Pro Ala Arg Trp Ser
            835                 840                 845

Val Ser Ser Ala Val Leu Pro Asn Tyr Arg Leu Val Ala Ala Leu Pro
        850                 855                 860

Met Ala Tyr His Asn Gln Arg Met Arg Phe Arg Thr Asp Leu Ser Tyr
865                 870                 875                 880

Gly Val Tyr Gly Phe Ala Glu Ile Asn Pro Ile Ala Leu Val Glu Lys
                885                 890                 895

Pro Ala Leu Ser Trp Lys Ser Arg Leu Arg Arg Lys Asn Ser Ser Ile
            900                 905                 910

Ala Leu Ala Asn Met Glu Asp Gly Gly Ser Val Gly Arg Ser Asn Asp
        915                 920                 925

Ile Pro Gly Arg Arg Ala Arg Phe Ile Gly Glu Lys Ala Glu Asp Pro
930                 935                 940

Pro Ala Pro Ser Pro Arg Pro Ala Leu Arg Ile Pro Asn Pro Leu Leu
945                 950                 955                 960

Gly Leu Asp

<210> SEQ ID NO 64
<211> LENGTH: 968
<212> TYPE: PRT
<213> ORGANISM: Artificial Sequence
<220> FEATURE:
<223> OTHER INFORMATION: Vaccine polypeptide

<400> SEQUENCE: 64

Met Thr Val Thr Glu Val Val Ala Gln Pro Val Trp Ala Gly Val
1               5                  10                  15

Asp Ala Gly Lys Ala Asp His Tyr Cys Met Val Ile Asn Asp Asp Ala
                20                  25                  30

Gln Arg Leu Leu Ser Gln Arg Val Ala Asn Asp Glu Ala Ala Leu Leu
            35                  40                  45

Glu Leu Ile Ala Ala Val Thr Thr Leu Ala Asp Gly Gly Glu Val Thr
        50                  55                  60

Trp Ala Ile Asp Leu Asn Ala Gly Gly Ala Ala Leu Leu Ile Ala Leu
65                  70                  75                  80

Leu Ile Ala Ala Gly Gln Arg Leu Leu Tyr Ile Pro Gly Arg Thr Val
                85                  90                  95

His His Ala Ala Gly Ser Tyr Arg Gly Glu Ala Pro Val Lys Gln Thr
            100                 105                 110

Leu Asn Phe Asp Leu Leu Lys Leu Ala Gly Asp Val Glu Ser Asn Pro
        115                 120                 125

Gly Pro Met Gln Ile Phe Val Lys Leu Pro Leu Leu Thr Ile Gly Asp
    130                 135                 140

Gln Phe Pro Ala Tyr Glu Leu Thr Ala Leu Ile Ala Gly Asp Leu Ser
145                 150                 155                 160

Lys Val Asp Ala Lys Gln Pro Gly Asp Tyr Phe Thr Val Thr Ser
                165                 170                 175

Glu Asp His Ala Gly Lys Trp Arg Val Val Phe Phe Trp Pro Lys Asp
            180                 185                 190

Phe Thr Gly Pro Glu Ile Ala Thr Phe Gly Lys Leu Asn Asp Glu Phe
        195                 200                 205
```

```
Glu Asp Arg Asp Ala Gln Val Leu Gly Val Ser Ile Asp Ser Glu Phe
    210                 215                 220

Val His Phe Asn Trp Arg Ala Gln His Glu Asp Leu Lys Asn Leu Pro
225                 230                 235                 240

Phe Pro Met Leu Ser Asp Ile Lys Arg Glu Leu Ser Leu Ala Thr Gly
                245                 250                 255

Val Leu Asn Ala Asp Gly Val Ala Asp Arg Ala Thr Phe Ile Val Asp
            260                 265                 270

Pro Asn Asn Glu Ile Gln Phe Val Ser Val Thr Ala Gly Ser Val Gly
        275                 280                 285

Arg Asn Val Glu Glu Val Leu Arg Val Leu Asp Ala Leu Gln Ser Asp
    290                 295                 300

Glu Leu Cys Ala Cys Asn Trp Arg Lys Gly Asp Pro Thr Leu Asn Ala
305                 310                 315                 320

Thr Glu Leu Leu Lys Ala Ser Ala Leu Gly Ser Ile Val Gly Gln Thr
                325                 330                 335

Tyr Arg Glu Val Glu Val Leu Val Asp Gly Gly Ser Thr Asp Arg
            340                 345                 350

Thr Leu Asp Ile Ala Asn Ser Phe Arg Pro Glu Leu Gly Ser Arg Leu
            355                 360                 365

Val Val His Ser Gly Pro Asp Asp Gly Pro Tyr Asp Ala Met Asn Arg
    370                 375                 380

Gly Val Gly Val Ala Thr Gly Glu Trp Val Leu Phe Leu Gly Ala Asp
385                 390                 395                 400

Asp Thr Leu Tyr Glu Pro Thr Thr Leu Ala Gln Val Ala Ala Phe Leu
                405                 410                 415

Gly Asp His Ala Ala Ser His Leu Val Tyr Gly Asp Val Val Met Arg
            420                 425                 430

Ser Thr Lys Ser Arg His Ala Gly Pro Phe Asp Leu Asp Arg Leu Leu
            435                 440                 445

Phe Glu Thr Asn Leu Cys His Gln Ser Ile Phe Tyr Arg Arg Glu Leu
    450                 455                 460

Phe Asp Gly Ile Gly Pro Tyr Asn Leu Arg Tyr Arg Val Trp Ala Asp
465                 470                 475                 480

Trp Asp Phe Asn Ile Arg Cys Phe Ser Asn Pro Ala Leu Ile Thr Arg
                485                 490                 495

Tyr Met Asp Val Val Ile Ser Glu Tyr Asn Asp Met Thr Gly Phe Ser
            500                 505                 510

Met Arg Gln Gly Thr Asp Lys Glu Phe Arg Lys Arg Leu Pro Met Tyr
            515                 520                 525

Phe Trp Val Ala Gly Trp Glu Thr Cys Arg Arg Met Leu Ala Phe Leu
    530                 535                 540

Lys Asp Lys Glu Asn Arg Arg Leu Ala Leu Arg Thr Arg Leu Ile Arg
545                 550                 555                 560

Val Lys Ala Val Ser Lys Glu Arg Ser Ala Glu Pro Arg Ile Arg Arg
                565                 570                 575

His Arg His Ala Glu Ile Ile Leu Ser Met Pro Gly Phe Gly Val Ile
            580                 585                 590

Leu Gly Ala Glu Phe Leu Ala Ala Thr Gly Gly Asp Met Ala Ala Phe
            595                 600                 605

Ala Ser Ala Asp Arg Leu Ala Gly Val Ala Gly Leu Ala Pro Val Pro
    610                 615                 620
```

-continued

```
Arg Asp Ser Gly Arg Ile Ser Gly Asn Leu Lys Pro Arg Arg Tyr
625                 630                 635                 640

Asp Arg Arg Leu Leu Arg Ala Cys Tyr Leu Ser Ala Leu Val Ser Ile
            645                 650                 655

Arg Thr Asp Pro Ser Ser Arg Thr Tyr Tyr Asp Arg Lys Arg Thr Glu
        660                 665                 670

Gly Lys Arg His Thr Gln Ala Val Leu Ala Leu Ala Arg Arg Arg Leu
    675                 680                 685

Asn Val Leu Trp Ala Met Leu Arg Asp His Ala Val Tyr His Pro Ala
690                 695                 700

Thr Thr Thr Ala Ala Ala Arg Leu Lys Leu Arg Arg Gly Glu Arg Pro
705                 710                 715                 720

Met Ser Leu Gly Gln Val Phe Asp Pro Arg Ala Asn Ala Leu His Ser
                725                 730                 735

Phe Pro Leu Thr Gly Arg Met Pro Trp Ala Pro Phe Ile Val Ser Ser
            740                 745                 750

Trp Leu Arg Asn Pro His Pro Ala Gln Tyr Phe Thr Ala Arg Cys Leu
        755                 760                 765

Arg Ile Leu Pro Gly Leu Trp Ile Gly Ala Gln Gly Gly Ser Ala Ala
    770                 775                 780

Lys Leu Leu Met Ser Gly Ala Pro Ile Glu Tyr Val Leu Lys Asp Ser
785                 790                 795                 800

Ala Val Trp Met Phe Lys Phe Asp Ile Gly Thr Pro Arg Asp Ile
                805                 810                 815

Pro Val Ala Gly Ile Trp Asn Gly Ser Leu Trp Thr Pro Ala Trp Gly
            820                 825                 830

Gly Ile His Ala Ile Ala Ser Asn Ala Tyr Gln Phe Arg Asn Val Ile
        835                 840                 845

Pro Ala Arg Trp Ser Val Ser Ser Ala Val Leu Pro Asn Tyr Arg Leu
    850                 855                 860

Val Ala Ala Leu Pro Met Ala Tyr His Asn Gln Arg Met Arg Phe Arg
865                 870                 875                 880

Thr Asp Leu Ser Tyr Gly Val Tyr Gly Phe Ala Glu Ile Asn Pro Ile
                885                 890                 895

Ala Leu Val Glu Lys Pro Ala Leu Ser Trp Lys Ser Arg Leu Arg Arg
            900                 905                 910

Lys Asn Ser Ser Ile Ala Leu Ala Asn Met Glu Asp Gly Gly Ser Val
        915                 920                 925

Gly Arg Ser Asn Asp Ile Pro Gly Arg Arg Ala Arg Phe Ile Gly Glu
    930                 935                 940

Lys Ala Glu Asp Pro Pro Ala Pro Ser Pro Arg Pro Ala Leu Arg Ile
945                 950                 955                 960

Pro Asn Pro Leu Leu Gly Leu Asp
                965
```

<210> SEQ ID NO 65
<211> LENGTH: 963
<212> TYPE: PRT
<213> ORGANISM: Artificial Sequence
<220> FEATURE:
<223> OTHER INFORMATION: Vaccine polypeptide

<400> SEQUENCE: 65

```
Met Thr Val Thr Glu Val Val Ala Gln Pro Val Trp Ala Gly Val
1               5                   10                  15
```

```
Asp Ala Gly Lys Ala Asp His Tyr Cys Met Val Ile Asn Asp Ala
            20                  25                  30
Gln Arg Leu Leu Ser Gln Arg Val Ala Asn Asp Glu Ala Ala Leu Leu
        35                  40                  45
Glu Leu Ile Ala Ala Val Thr Thr Leu Ala Asp Gly Gly Glu Val Thr
50                  55                  60
Trp Ala Ile Asp Leu Asn Ala Gly Gly Ala Ala Leu Leu Ile Ala Leu
65                  70                  75                  80
Leu Ile Ala Ala Gly Gln Arg Leu Leu Tyr Ile Pro Gly Arg Thr Val
                85                  90                  95
His His Ala Ala Gly Ser Tyr Arg Gly Glu Ala Pro Val Lys Gln Thr
            100                 105                 110
Leu Asn Phe Asp Leu Leu Lys Leu Ala Gly Asp Val Glu Ser Asn Pro
        115                 120                 125
Gly Pro Met Gln Ile Phe Val Lys Leu Pro Leu Leu Thr Ile Gly Asp
130                 135                 140
Gln Phe Pro Ala Tyr Glu Leu Thr Ala Leu Ile Ala Gly Asp Leu Ser
145                 150                 155                 160
Lys Val Asp Ala Lys Gln Pro Gly Asp Tyr Phe Thr Thr Val Thr Ser
                165                 170                 175
Glu Asp His Ala Gly Lys Trp Arg Val Val Phe Phe Trp Pro Lys Asp
            180                 185                 190
Phe Thr Gly Pro Glu Ile Ala Thr Phe Gly Lys Leu Asn Asp Glu Phe
        195                 200                 205
Glu Asp Arg Asp Ala Gln Val Leu Gly Val Ser Ile Asp Ser Glu Phe
210                 215                 220
Val His Phe Asn Trp Arg Ala Gln His Glu Asp Leu Lys Asn Leu Pro
225                 230                 235                 240
Phe Pro Met Leu Ser Asp Ile Lys Arg Glu Leu Ser Leu Ala Thr Gly
                245                 250                 255
Val Leu Asn Ala Asp Gly Val Ala Asp Arg Ala Thr Phe Ile Val Asp
            260                 265                 270
Pro Asn Asn Glu Ile Gln Phe Val Ser Val Thr Ala Gly Ser Val Gly
        275                 280                 285
Arg Asn Val Glu Glu Val Leu Arg Val Leu Asp Ala Leu Gln Ser Asp
290                 295                 300
Glu Leu Cys Ala Cys Asn Trp Arg Lys Gly Asp Pro Thr Leu Asn Ala
305                 310                 315                 320
Thr Glu Leu Leu Lys Ala Ser Ala Leu Gly Ser Ile Val Gly Gln Thr
                325                 330                 335
Tyr Arg Glu Val Glu Val Val Leu Val Asp Gly Gly Ser Thr Asp Arg
            340                 345                 350
Thr Leu Asp Ile Ala Asn Ser Phe Arg Pro Glu Leu Gly Ser Arg Leu
        355                 360                 365
Val Val His Ser Gly Pro Asp Asp Gly Pro Tyr Asp Ala Met Asn Arg
370                 375                 380
Gly Val Gly Val Ala Thr Gly Glu Trp Val Leu Phe Leu Gly Ala Asp
385                 390                 395                 400
Asp Thr Leu Tyr Glu Pro Thr Leu Ala Gln Val Ala Ala Phe Leu
                405                 410                 415
Gly Asp His Ala Ala Ser His Leu Val Tyr Gly Asp Val Val Met Arg
            420                 425                 430
Ser Thr Lys Ser Arg His Ala Gly Pro Phe Asp Leu Asp Arg Leu Leu
```

```
           435                 440                 445
Phe Glu Thr Asn Leu Cys His Gln Ser Ile Phe Tyr Arg Arg Glu Leu
450                 455                 460

Phe Asp Gly Ile Gly Pro Tyr Asn Leu Arg Tyr Arg Val Trp Ala Asp
465                 470                 475                 480

Trp Asp Phe Asn Ile Arg Cys Phe Ser Asn Pro Ala Leu Ile Thr Arg
                485                 490                 495

Tyr Met Asp Val Val Ile Ser Glu Tyr Asn Asp Met Thr Gly Phe Ser
                500                 505                 510

Met Arg Gln Gly Thr Asp Lys Glu Phe Arg Lys Arg Leu Pro Met Tyr
                515                 520                 525

Phe Trp Val Ala Gly Trp Glu Thr Cys Arg Arg Met Leu Ala Phe Leu
530                 535                 540

Lys Asp Lys Glu Asn Arg Arg Leu Ala Leu Arg Thr Arg Leu Ile Arg
545                 550                 555                 560

Val Lys Ala Val Ser Lys Glu Arg Ser Ala Glu Pro Arg Ile Arg Arg
                565                 570                 575

His Arg His Ala Glu Ile Ile Leu Ser Met Pro Gly Phe Gly Val Ile
                580                 585                 590

Leu Gly Ala Glu Phe Leu Ala Ala Thr Gly Gly Asp Met Ala Ala Phe
                595                 600                 605

Ala Ser Ala Asp Arg Leu Ala Gly Val Ala Gly Leu Ala Pro Val Pro
610                 615                 620

Arg Asp Ser Gly Arg Ile Ser Gly Asn Leu Lys Arg Pro Arg Arg Tyr
625                 630                 635                 640

Asp Arg Arg Leu Leu Arg Ala Cys Val Ser Ile Arg Thr Asp Pro Ser
                645                 650                 655

Ser Arg Thr Tyr Tyr Asp Arg Lys Arg Thr Glu Gly Lys Arg His Thr
                660                 665                 670

Gln Ala Val Leu Ala Leu Ala Arg Arg Leu Asn Val Leu Trp Ala
                675                 680                 685

Met Leu Arg Asp His Ala Val Tyr His Pro Ala Thr Thr Thr Ala Ala
690                 695                 700

Ala Arg Leu Lys Leu Arg Arg Gly Glu Arg Pro Met Ser Leu Gly Gln
705                 710                 715                 720

Val Phe Asp Pro Arg Ala Asn Ala Leu His Ser Phe Pro Leu Thr Gly
                725                 730                 735

Arg Met Pro Trp Ala Pro Phe Ile Val Ser Ser Trp Leu Arg Asn Pro
                740                 745                 750

His Pro Ala Gln Tyr Phe Thr Ala Arg Cys Leu Arg Ile Leu Pro Gly
                755                 760                 765

Leu Trp Ile Gly Ala Gln Gly Gly Ser Ala Ala Lys Leu Leu Met Ser
770                 775                 780

Gly Ala Pro Ile Glu Tyr Val Leu Lys Asp Ser Ala Val Trp Met Phe
785                 790                 795                 800

Lys Phe Asp Ile Gly Gly Thr Pro Arg Asp Ile Pro Val Ala Gly Ile
                805                 810                 815

Trp Asn Gly Ser Leu Trp Thr Pro Ala Trp Gly Gly Ile His Ala Ile
                820                 825                 830

Ala Ser Asn Ala Tyr Gln Phe Arg Asn Val Ile Pro Ala Arg Trp Ser
                835                 840                 845

Val Ser Ser Ala Val Leu Pro Asn Tyr Arg Leu Val Ala Ala Leu Pro
850                 855                 860
```

```
Met Ala Tyr His Asn Gln Arg Met Arg Phe Arg Thr Asp Leu Ser Tyr
865                 870                 875                 880

Gly Val Tyr Gly Phe Ala Glu Ile Asn Pro Ile Ala Leu Val Glu Lys
                885                 890                 895

Pro Ala Leu Ser Trp Lys Ser Arg Leu Arg Arg Lys Asn Ser Ser Ile
            900                 905                 910

Ala Leu Ala Asn Met Glu Asp Gly Gly Ser Val Gly Arg Ser Asn Asp
        915                 920                 925

Ile Pro Gly Arg Arg Ala Arg Phe Ile Gly Glu Lys Ala Glu Asp Pro
    930                 935                 940

Pro Ala Pro Ser Pro Arg Pro Ala Leu Arg Ile Pro Asn Pro Leu Leu
945                 950                 955                 960

Gly Leu Asp

<210> SEQ ID NO 66
<211> LENGTH: 939
<212> TYPE: PRT
<213> ORGANISM: Artificial Sequence
<220> FEATURE:
<223> OTHER INFORMATION: Vaccine polypeptide

<400> SEQUENCE: 66

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
            20                  25                  30

Glu Val Thr Trp Ala Ile Asp Leu Asn Ala Gly Ala Ala Leu Leu
        35                  40                  45

Ile Ala Leu Leu Ile Ala Ala Gly Gln Arg Leu Leu Tyr Ile Pro Gly
50                  55                  60

Ala Thr Val His His Ala Ala Gly Ser Tyr Arg Gly Glu Ala Pro Val
65                  70                  75                  80

Lys Gln Thr Leu Asn Phe Asp Leu Leu Lys Leu Ala Gly Asp Val Glu
                85                  90                  95

Ser Asn Pro Gly Pro Met Gln Ile Phe Val Lys Leu Pro Leu Leu Thr
            100                 105                 110

Ile Gly Asp Gln Phe Pro Ala Tyr Glu Leu Thr Ala Leu Ile Ala Gly
        115                 120                 125

Asp Leu Ser Lys Val Asp Ala Lys Gln Pro Gly Asp Tyr Phe Thr Thr
    130                 135                 140

Val Thr Ser Glu Asp His Ala Gly Lys Trp Arg Val Val Phe Phe Trp
145                 150                 155                 160

Pro Lys Asp Phe Thr Gly Pro Glu Ile Ala Thr Phe Gly Lys Leu Asn
                165                 170                 175

Asp Glu Phe Glu Asp Arg Asp Ala Gln Val Leu Gly Val Ser Ile Asp
            180                 185                 190

Ser Glu Phe Val His Phe Asn Trp Arg Ala Gln His Glu Asp Leu Lys
        195                 200                 205

Asn Leu Pro Phe Pro Met Leu Ser Asp Ile Lys Arg Glu Leu Ser Leu
    210                 215                 220

Ala Thr Gly Val Leu Asn Ala Asp Gly Val Ala Asp Arg Ala Thr Phe
225                 230                 235                 240

Ile Val Asp Pro Asn Asn Glu Ile Gln Phe Val Ser Val Thr Ala Gly
                245                 250                 255
```

-continued

Ser Val Gly Arg Asn Val Glu Glu Val Leu Arg Val Leu Asp Ala Leu
            260                 265                 270

Gln Ser Asp Glu Leu Cys Ala Cys Asn Trp Arg Lys Gly Asp Pro Thr
        275                 280                 285

Leu Asn Ala Thr Glu Leu Leu Lys Ala Ser Ala Leu Gly Ser Ile Val
    290                 295                 300

Gly Gln Thr Tyr Arg Glu Val Glu Val Val Leu Val Asp Gly Gly Ser
305                 310                 315                 320

Thr Asp Arg Thr Leu Asp Ile Ala Asn Ser Phe Arg Pro Glu Leu Gly
                325                 330                 335

Ser Arg Leu Val Val His Ser Gly Pro Asp Asp Gly Pro Tyr Asp Ala
            340                 345                 350

Met Asn Arg Gly Val Gly Val Ala Thr Gly Glu Trp Val Leu Phe Leu
        355                 360                 365

Gly Ala Asp Asp Thr Leu Tyr Glu Pro Thr Thr Leu Ala Gln Val Ala
    370                 375                 380

Ala Phe Leu Gly Asp His Ala Ala Ser His Leu Val Tyr Gly Asp Val
385                 390                 395                 400

Val Met Arg Ser Thr Lys Ser Arg His Ala Gly Pro Phe Asp Leu Asp
                405                 410                 415

Arg Leu Leu Phe Glu Thr Asn Leu Cys His Gln Ser Ile Phe Tyr Arg
            420                 425                 430

Arg Glu Leu Phe Asp Gly Ile Gly Pro Tyr Asn Leu Arg Tyr Arg Val
        435                 440                 445

Trp Ala Asp Trp Asp Phe Asn Ile Arg Cys Phe Ser Asn Pro Ala Leu
    450                 455                 460

Ile Thr Arg Tyr Met Asp Val Val Ile Ser Glu Tyr Asn Asp Met Thr
465                 470                 475                 480

Gly Phe Ser Met Arg Gln Gly Thr Asp Lys Glu Phe Arg Lys Arg Leu
                485                 490                 495

Pro Met Tyr Phe Trp Val Ala Gly Trp Glu Thr Cys Arg Arg Met Leu
            500                 505                 510

Ala Phe Leu Lys Asp Lys Glu Asn Arg Arg Leu Ala Leu Arg Thr Arg
        515                 520                 525

Leu Ile Arg Val Lys Ala Val Ser Lys Glu Arg Ser Ala Glu Pro Arg
    530                 535                 540

Ile Arg Arg His Arg His Ala Glu Ile Ile Leu Ser Met Pro Gly Phe
545                 550                 555                 560

Gly Val Ile Leu Gly Ala Glu Phe Leu Ala Thr Gly Gly Asp Met
                565                 570                 575

Ala Ala Phe Ala Ser Ala Asp Arg Leu Ala Gly Val Ala Gly Leu Ala
            580                 585                 590

Pro Val Pro Arg Asp Ser Gly Arg Ile Ser Gly Asn Leu Lys Arg Pro
        595                 600                 605

Arg Arg Tyr Asp Arg Arg Leu Leu Arg Ala Cys Tyr Leu Ser Ala Leu
    610                 615                 620

Val Ser Ile Arg Thr Asp Pro Ser Ser Arg Thr Tyr Tyr Asp Arg Lys
625                 630                 635                 640

Arg Thr Glu Gly Lys Arg His Thr Gln Ala Val Leu Ala Leu Ala Arg
                645                 650                 655

Arg Arg Leu Asn Val Leu Trp Ala Met Leu Arg Asp His Ala Val Tyr
            660                 665                 670

His Pro Ala Thr Thr Thr Ala Ala Ala Arg Leu Lys Leu Arg Arg Gly

```
                675                 680                 685

Glu Arg Pro Met Ser Leu Gly Gln Val Phe Asp Pro Arg Ala Asn Ala
690                 695                 700

Leu His Ser Phe Pro Leu Thr Gly Arg Met Pro Trp Ala Pro Phe Ile
705                 710                 715                 720

Val Ser Ser Trp Leu Arg Asn Pro His Pro Ala Gln Tyr Phe Thr Ala
                725                 730                 735

Arg Cys Leu Arg Ile Leu Pro Gly Leu Trp Ile Gly Ala Gln Gly Gly
                740                 745                 750

Ser Ala Ala Lys Leu Leu Met Ser Gly Ala Pro Ile Glu Tyr Val Leu
                755                 760                 765

Lys Asp Ser Ala Val Trp Met Phe Lys Phe Asp Ile Gly Gly Thr Pro
770                 775                 780

Arg Asp Ile Pro Val Ala Gly Ile Trp Asn Gly Ser Leu Trp Thr Pro
785                 790                 795                 800

Ala Trp Gly Gly Ile His Ala Ile Ala Ser Asn Ala Tyr Gln Phe Arg
                805                 810                 815

Asn Val Ile Pro Ala Arg Trp Ser Val Ser Ser Ala Val Leu Pro Asn
                820                 825                 830

Tyr Arg Leu Val Ala Ala Leu Pro Met Ala Tyr His Asn Gln Arg Met
                835                 840                 845

Arg Phe Arg Thr Asp Leu Ser Tyr Gly Val Tyr Gly Phe Ala Glu Ile
850                 855                 860

Asn Pro Ile Ala Leu Val Glu Lys Pro Ala Leu Ser Trp Lys Ser Arg
865                 870                 875                 880

Leu Arg Arg Lys Asn Ser Ser Ile Ala Leu Ala Asn Met Glu Asp Gly
                885                 890                 895

Gly Ser Val Gly Arg Ser Asn Asp Ile Pro Gly Arg Arg Ala Arg Phe
                900                 905                 910

Ile Gly Glu Lys Ala Glu Asp Pro Pro Ala Pro Ser Pro Arg Pro Ala
                915                 920                 925

Leu Arg Ile Pro Asn Pro Leu Leu Gly Leu Asp
    930                 935

<210> SEQ ID NO 67
<211> LENGTH: 934
<212> TYPE: PRT
<213> ORGANISM: Artificial Sequence
<220> FEATURE:
<223> OTHER INFORMATION: Vaccine polypeptide

<400> SEQUENCE: 67

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
                20                  25                  30

Glu Val Thr Trp Ala Ile Asp Leu Asn Ala Gly Ala Ala Leu Leu
            35                  40                  45

Ile Ala Leu Leu Ile Ala Ala Gly Gln Arg Leu Leu Tyr Ile Pro Gly
    50                  55                  60

Ala Thr Val His His Ala Gly Ser Tyr Arg Gly Glu Ala Pro Val
65                  70                  75                  80

Lys Gln Thr Leu Asn Phe Asp Leu Leu Lys Leu Ala Gly Asp Val Glu
                85                  90                  95

Ser Asn Pro Gly Pro Met Gln Ile Phe Val Lys Leu Pro Leu Leu Thr
```

-continued

```
                100             105             110
Ile Gly Asp Gln Phe Pro Ala Tyr Glu Leu Thr Ala Leu Ile Ala Gly
            115             120             125
Asp Leu Ser Lys Val Asp Ala Lys Gln Pro Gly Asp Tyr Phe Thr Thr
            130             135             140
Val Thr Ser Glu Asp His Ala Gly Lys Trp Arg Val Phe Phe Trp
145             150             155             160
Pro Lys Asp Phe Thr Gly Pro Glu Ile Ala Thr Phe Gly Lys Leu Asn
                165             170             175
Asp Glu Phe Glu Asp Arg Asp Ala Gln Val Leu Gly Val Ser Ile Asp
            180             185             190
Ser Glu Phe Val His Phe Asn Trp Arg Ala Gln His Glu Asp Leu Lys
            195             200             205
Asn Leu Pro Phe Pro Met Leu Ser Asp Ile Lys Arg Glu Leu Ser Leu
            210             215             220
Ala Thr Gly Val Leu Asn Ala Asp Gly Val Ala Asp Arg Ala Thr Phe
225             230             235             240
Ile Val Asp Pro Asn Asn Glu Ile Gln Phe Val Ser Val Thr Ala Gly
            245             250             255
Ser Val Gly Arg Asn Val Glu Glu Val Leu Arg Val Leu Asp Ala Leu
            260             265             270
Gln Ser Asp Glu Leu Cys Ala Cys Asn Trp Arg Lys Gly Asp Pro Thr
            275             280             285
Leu Asn Ala Thr Glu Leu Leu Lys Ala Ser Ala Leu Gly Ser Ile Val
            290             295             300
Gly Gln Thr Tyr Arg Glu Val Glu Val Val Leu Val Asp Gly Gly Ser
305             310             315             320
Thr Asp Arg Thr Leu Asp Ile Ala Asn Ser Phe Arg Pro Glu Leu Gly
            325             330             335
Ser Arg Leu Val Val His Ser Gly Pro Asp Asp Gly Pro Tyr Asp Ala
            340             345             350
Met Asn Arg Gly Val Gly Val Ala Thr Gly Glu Trp Val Leu Phe Leu
            355             360             365
Gly Ala Asp Asp Thr Leu Tyr Glu Pro Thr Thr Leu Ala Gln Val Ala
            370             375             380
Ala Phe Leu Gly Asp His Ala Ser His Leu Val Tyr Gly Asp Val
385             390             395             400
Val Met Arg Ser Thr Lys Ser Arg His Ala Gly Pro Phe Asp Leu Asp
            405             410             415
Arg Leu Leu Phe Glu Thr Asn Leu Cys His Gln Ser Ile Phe Tyr Arg
            420             425             430
Arg Glu Leu Phe Asp Gly Ile Gly Pro Tyr Asn Leu Arg Tyr Arg Val
            435             440             445
Trp Ala Asp Trp Asp Phe Asn Ile Arg Cys Phe Ser Asn Pro Ala Leu
            450             455             460
Ile Thr Arg Tyr Met Asp Val Val Ile Ser Glu Tyr Asn Asp Met Thr
465             470             475             480
Gly Phe Ser Met Arg Gln Gly Thr Asp Lys Glu Phe Lys Arg Leu
            485             490             495
Pro Met Tyr Phe Trp Val Ala Gly Trp Glu Thr Cys Arg Arg Met Leu
            500             505             510
Ala Phe Leu Lys Asp Lys Glu Asn Arg Arg Leu Ala Leu Arg Thr Arg
            515             520             525
```

-continued

Leu Ile Arg Val Lys Ala Val Ser Lys Glu Arg Ser Ala Glu Pro Arg
    530                 535                 540

Ile Arg Arg His Arg His Ala Glu Ile Ile Leu Ser Met Pro Gly Phe
545                 550                 555                 560

Gly Val Ile Leu Gly Ala Glu Phe Leu Ala Ala Thr Gly Gly Asp Met
                565                 570                 575

Ala Ala Phe Ala Ser Ala Asp Arg Leu Ala Gly Val Ala Gly Leu Ala
            580                 585                 590

Pro Val Pro Arg Asp Ser Gly Arg Ile Ser Gly Asn Leu Lys Arg Pro
        595                 600                 605

Arg Arg Tyr Asp Arg Arg Leu Leu Arg Ala Cys Val Ser Ile Arg Thr
    610                 615                 620

Asp Pro Ser Ser Arg Thr Tyr Tyr Asp Arg Lys Arg Thr Glu Gly Lys
625                 630                 635                 640

Arg His Thr Gln Ala Val Leu Ala Leu Ala Arg Arg Arg Leu Asn Val
                645                 650                 655

Leu Trp Ala Met Leu Arg Asp His Ala Val Tyr His Pro Ala Thr Thr
            660                 665                 670

Thr Ala Ala Ala Arg Leu Lys Leu Arg Arg Gly Glu Arg Pro Met Ser
        675                 680                 685

Leu Gly Gln Val Phe Asp Pro Arg Ala Asn Ala Leu His Ser Phe Pro
    690                 695                 700

Leu Thr Gly Arg Met Pro Trp Ala Pro Phe Ile Val Ser Ser Trp Leu
705                 710                 715                 720

Arg Asn Pro His Pro Ala Gln Tyr Phe Thr Ala Arg Cys Leu Arg Ile
                725                 730                 735

Leu Pro Gly Leu Trp Ile Gly Ala Gln Gly Gly Ser Ala Ala Lys Leu
            740                 745                 750

Leu Met Ser Gly Ala Pro Ile Glu Tyr Val Leu Lys Asp Ser Ala Val
        755                 760                 765

Trp Met Phe Lys Phe Asp Ile Gly Gly Thr Pro Arg Asp Ile Pro Val
    770                 775                 780

Ala Gly Ile Trp Asn Gly Ser Leu Trp Thr Pro Ala Trp Gly Gly Ile
785                 790                 795                 800

His Ala Ile Ala Ser Asn Ala Tyr Gln Phe Arg Asn Val Ile Pro Ala
                805                 810                 815

Arg Trp Ser Val Ser Ser Ala Val Leu Pro Asn Tyr Arg Leu Val Ala
            820                 825                 830

Ala Leu Pro Met Ala Tyr His Asn Gln Arg Met Arg Phe Arg Thr Asp
        835                 840                 845

Leu Ser Tyr Gly Val Tyr Gly Phe Ala Glu Ile Asn Pro Ile Ala Leu
    850                 855                 860

Val Glu Lys Pro Ala Leu Ser Trp Lys Ser Arg Leu Arg Arg Lys Asn
865                 870                 875                 880

Ser Ser Ile Ala Leu Ala Asn Met Glu Asp Gly Gly Ser Val Gly Arg
                885                 890                 895

Ser Asn Asp Ile Pro Gly Arg Arg Ala Arg Phe Ile Gly Glu Lys Ala
            900                 905                 910

Glu Asp Pro Pro Ala Pro Ser Pro Arg Pro Ala Leu Arg Ile Pro Asn
        915                 920                 925

Pro Leu Leu Gly Leu Asp
    930

```
<210> SEQ ID NO 68
<211> LENGTH: 939
<212> TYPE: PRT
<213> ORGANISM: Artificial Sequence
<220> FEATURE:
<223> OTHER INFORMATION: Vaccine polypeptide

<400> SEQUENCE: 68
```

| Met | Val | Ile | Asn | Asp | Asp | Ala | Gln | Arg | Leu | Leu | Ser | Gln | Arg | Val | Asp |
|---|---|---|---|---|---|---|---|---|---|---|---|---|---|---|---|
| 1 | | | | 5 | | | | | 10 | | | | | 15 | |
| Ala | Gly | Lys | Ala | Asp | His | Tyr | Ala | Val | Thr | Thr | Leu | Ala | Asp | Gly | Gly |
| | | | 20 | | | | | 25 | | | | | 30 | | |
| Glu | Val | Thr | Trp | Ala | Ile | Asp | Leu | Asn | Ala | Gly | Gly | Ala | Ala | Leu | Leu |
| | | | 35 | | | | | 40 | | | | | 45 | | |
| Ile | Ala | Leu | Leu | Ile | Ala | Ala | Gly | Gln | Arg | Leu | Leu | Tyr | Ile | Pro | Gly |
| | 50 | | | | | 55 | | | | | 60 | | | | |
| Arg | Thr | Val | His | His | Ala | Ala | Gly | Ser | Tyr | Arg | Gly | Glu | Ala | Pro | Val |
| 65 | | | | | 70 | | | | | 75 | | | | | 80 |
| Lys | Gln | Thr | Leu | Asn | Phe | Asp | Leu | Leu | Lys | Leu | Ala | Gly | Asp | Val | Glu |
| | | | | 85 | | | | | 90 | | | | | 95 | |
| Ser | Asn | Pro | Gly | Pro | Met | Gln | Ile | Phe | Val | Lys | Leu | Pro | Leu | Leu | Thr |
| | | | 100 | | | | | 105 | | | | | 110 | | |
| Ile | Gly | Asp | Gln | Phe | Pro | Ala | Tyr | Glu | Leu | Thr | Ala | Leu | Ile | Ala | Gly |
| | | | | 115 | | | | | 120 | | | | | 125 | |
| Asp | Leu | Ser | Lys | Val | Asp | Ala | Lys | Gln | Pro | Gly | Asp | Tyr | Phe | Thr | Thr |
| | 130 | | | | | 135 | | | | | 140 | | | | |
| Val | Thr | Ser | Glu | Asp | His | Ala | Gly | Lys | Trp | Arg | Val | Phe | Phe | Trp |
| 145 | | | | | 150 | | | | | 155 | | | | | 160 |
| Pro | Lys | Asp | Phe | Thr | Gly | Pro | Glu | Ile | Ala | Thr | Phe | Gly | Lys | Leu | Asn |
| | | | | 165 | | | | | 170 | | | | | 175 | |
| Asp | Glu | Phe | Glu | Asp | Arg | Asp | Ala | Gln | Val | Leu | Gly | Val | Ser | Ile | Asp |
| | | | 180 | | | | | 185 | | | | | 190 | | |
| Ser | Glu | Phe | Val | His | Phe | Asn | Trp | Arg | Ala | Gln | His | Glu | Asp | Leu | Lys |
| | | | | 195 | | | | | 200 | | | | | 205 | |
| Asn | Leu | Pro | Phe | Pro | Met | Leu | Ser | Asp | Ile | Lys | Arg | Glu | Leu | Ser | Leu |
| | 210 | | | | | 215 | | | | | 220 | | | | |
| Ala | Thr | Gly | Val | Leu | Asn | Ala | Asp | Gly | Val | Ala | Asp | Arg | Ala | Thr | Phe |
| 225 | | | | | 230 | | | | | 235 | | | | | 240 |
| Ile | Val | Asp | Pro | Asn | Asn | Glu | Ile | Gln | Phe | Val | Ser | Val | Thr | Ala | Gly |
| | | | | 245 | | | | | 250 | | | | | 255 | |
| Ser | Val | Gly | Arg | Asn | Val | Glu | Glu | Val | Leu | Arg | Val | Leu | Asp | Ala | Leu |
| | | | 260 | | | | | 265 | | | | | 270 | | |
| Gln | Ser | Asp | Glu | Leu | Cys | Ala | Cys | Asn | Trp | Arg | Lys | Gly | Asp | Pro | Thr |
| | | | | 275 | | | | | 280 | | | | | 285 | |
| Leu | Asn | Ala | Thr | Glu | Leu | Leu | Lys | Ala | Ser | Ala | Leu | Gly | Ser | Ile | Val |
| | 290 | | | | | 295 | | | | | 300 | | | | |
| Gly | Gln | Thr | Tyr | Arg | Glu | Val | Glu | Val | Val | Leu | Val | Asp | Gly | Gly | Ser |
| 305 | | | | | 310 | | | | | 315 | | | | | 320 |
| Thr | Asp | Arg | Thr | Leu | Asp | Ile | Ala | Asn | Ser | Phe | Arg | Pro | Glu | Leu | Gly |
| | | | | 325 | | | | | 330 | | | | | 335 | |
| Ser | Arg | Leu | Val | Val | His | Ser | Gly | Pro | Asp | Asp | Gly | Pro | Tyr | Asp | Ala |
| | | | 340 | | | | | 345 | | | | | 350 | | |
| Met | Asn | Arg | Gly | Val | Gly | Val | Ala | Thr | Gly | Glu | Trp | Val | Leu | Phe | Leu |
| | | | | 355 | | | | | 360 | | | | | 365 | |

```
Gly Ala Asp Asp Thr Leu Tyr Glu Pro Thr Thr Leu Ala Gln Val Ala
    370                 375                 380

Ala Phe Leu Gly Asp His Ala Ala Ser His Leu Val Tyr Gly Asp Val
385                 390                 395                 400

Val Met Arg Ser Thr Lys Ser Arg His Ala Gly Pro Phe Asp Leu Asp
                405                 410                 415

Arg Leu Leu Phe Glu Thr Asn Leu Cys His Gln Ser Ile Phe Tyr Arg
                420                 425                 430

Arg Glu Leu Phe Asp Gly Ile Gly Pro Tyr Asn Leu Arg Tyr Arg Val
                435                 440                 445

Trp Ala Asp Trp Asp Phe Asn Ile Arg Cys Phe Ser Asn Pro Ala Leu
450                 455                 460

Ile Thr Arg Tyr Met Asp Val Val Ile Ser Glu Tyr Asn Asp Met Thr
465                 470                 475                 480

Gly Phe Ser Met Arg Gln Gly Thr Asp Lys Glu Phe Arg Lys Arg Leu
                485                 490                 495

Pro Met Tyr Phe Trp Val Ala Gly Trp Glu Thr Cys Arg Arg Met Leu
                500                 505                 510

Ala Phe Leu Lys Asp Lys Glu Asn Arg Arg Leu Ala Leu Arg Thr Arg
                515                 520                 525

Leu Ile Arg Val Lys Ala Val Ser Lys Glu Arg Ser Ala Glu Pro Arg
530                 535                 540

Ile Arg Arg His Arg His Ala Glu Ile Ile Leu Ser Met Pro Gly Phe
545                 550                 555                 560

Gly Val Ile Leu Gly Ala Glu Phe Leu Ala Ala Thr Gly Gly Asp Met
                565                 570                 575

Ala Ala Phe Ala Ser Ala Asp Arg Leu Ala Gly Val Ala Gly Leu Ala
                580                 585                 590

Pro Val Pro Arg Asp Ser Gly Arg Ile Ser Gly Asn Leu Lys Arg Pro
                595                 600                 605

Arg Arg Tyr Asp Arg Arg Leu Leu Arg Ala Cys Tyr Leu Ser Ala Leu
610                 615                 620

Val Ser Ile Arg Thr Asp Pro Ser Ser Arg Thr Tyr Tyr Asp Arg Lys
625                 630                 635                 640

Arg Thr Glu Gly Lys Arg His Thr Gln Ala Val Leu Ala Leu Ala Arg
                645                 650                 655

Arg Arg Leu Asn Val Leu Trp Ala Met Leu Arg Asp His Ala Val Tyr
                660                 665                 670

His Pro Ala Thr Thr Thr Ala Ala Arg Leu Lys Leu Arg Arg Gly
                675                 680                 685

Glu Arg Pro Met Ser Leu Gly Gln Val Phe Asp Pro Arg Ala Asn Ala
690                 695                 700

Leu His Ser Phe Pro Leu Thr Gly Arg Met Pro Trp Ala Pro Phe Ile
705                 710                 715                 720

Val Ser Ser Trp Leu Arg Asn Pro His Pro Ala Gln Tyr Phe Thr Ala
                725                 730                 735

Arg Cys Leu Arg Ile Leu Pro Gly Leu Trp Ile Gly Ala Gln Gly Gly
                740                 745                 750

Ser Ala Ala Lys Leu Leu Met Ser Gly Ala Pro Ile Glu Tyr Val Leu
                755                 760                 765

Lys Asp Ser Ala Val Trp Met Phe Lys Phe Asp Ile Gly Gly Thr Pro
770                 775                 780

Arg Asp Ile Pro Val Ala Gly Ile Trp Asn Gly Ser Leu Trp Thr Pro
```

```
                785                 790                 795                 800
Ala Trp Gly Gly Ile His Ala Ile Ala Ser Asn Ala Tyr Gln Phe Arg
                    805                 810                 815

Asn Val Ile Pro Ala Arg Trp Ser Val Ser Ser Ala Val Leu Pro Asn
                820                 825                 830

Tyr Arg Leu Val Ala Ala Leu Pro Met Ala Tyr His Asn Gln Arg Met
                835                 840                 845

Arg Phe Arg Thr Asp Leu Ser Tyr Gly Val Tyr Gly Phe Ala Glu Ile
            850                 855                 860

Asn Pro Ile Ala Leu Val Glu Lys Pro Ala Leu Ser Trp Lys Ser Arg
865                 870                 875                 880

Leu Arg Arg Lys Asn Ser Ser Ile Ala Leu Ala Asn Met Glu Asp Gly
                885                 890                 895

Gly Ser Val Gly Arg Ser Asn Asp Ile Pro Gly Arg Arg Ala Arg Phe
                900                 905                 910

Ile Gly Glu Lys Ala Glu Asp Pro Pro Ala Pro Ser Pro Arg Pro Ala
            915                 920                 925

Leu Arg Ile Pro Asn Pro Leu Leu Gly Leu Asp
    930                 935

<210> SEQ ID NO 69
<211> LENGTH: 934
<212> TYPE: PRT
<213> ORGANISM: Artificial Sequence
<220> FEATURE:
<223> OTHER INFORMATION: Vaccine polypeptide

<400> SEQUENCE: 69

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
                20                  25                  30

Glu Val Thr Trp Ala Ile Asp Leu Asn Ala Gly Ala Ala Leu Leu
            35                  40                  45

Ile Ala Leu Leu Ile Ala Ala Gly Gln Arg Leu Leu Tyr Ile Pro Gly
        50                  55                  60

Arg Thr Val His His Ala Ala Gly Ser Tyr Arg Gly Glu Ala Pro Val
65                  70                  75                  80

Lys Gln Thr Leu Asn Phe Asp Leu Leu Lys Leu Ala Gly Asp Val Glu
                85                  90                  95

Ser Asn Pro Gly Pro Met Gln Ile Phe Val Lys Leu Pro Leu Leu Thr
                100                 105                 110

Ile Gly Asp Gln Phe Pro Ala Tyr Glu Leu Thr Ala Leu Ile Ala Gly
            115                 120                 125

Asp Leu Ser Lys Val Asp Ala Lys Gln Pro Gly Asp Tyr Phe Thr Thr
    130                 135                 140

Val Thr Ser Glu Asp His Ala Gly Lys Trp Arg Val Phe Phe Trp
145                 150                 155                 160

Pro Lys Asp Phe Thr Gly Pro Glu Ile Ala Thr Phe Gly Lys Leu Asn
                165                 170                 175

Asp Glu Phe Glu Asp Arg Asp Ala Gln Val Leu Gly Val Ser Ile Asp
                180                 185                 190

Ser Glu Phe Val His Phe Asn Trp Arg Ala Gln His Glu Asp Leu Lys
            195                 200                 205

Asn Leu Pro Phe Pro Met Leu Ser Asp Ile Lys Arg Glu Leu Ser Leu
```

```
              210                 215                 220
Ala Thr Gly Val Leu Asn Ala Asp Gly Val Ala Asp Arg Ala Thr Phe
225                 230                 235                 240

Ile Val Asp Pro Asn Asn Glu Ile Gln Phe Val Ser Val Thr Ala Gly
                    245                 250                 255

Ser Val Gly Arg Asn Val Glu Glu Val Leu Arg Val Leu Asp Ala Leu
                260                 265                 270

Gln Ser Asp Glu Leu Cys Ala Cys Asn Trp Arg Lys Gly Asp Pro Thr
            275                 280                 285

Leu Asn Ala Thr Glu Leu Leu Lys Ala Ser Ala Leu Gly Ser Ile Val
        290                 295                 300

Gly Gln Thr Tyr Arg Glu Val Glu Val Val Leu Val Asp Gly Gly Ser
305                 310                 315                 320

Thr Asp Arg Thr Leu Asp Ile Ala Asn Ser Phe Arg Pro Glu Leu Gly
                    325                 330                 335

Ser Arg Leu Val Val His Ser Gly Pro Asp Asp Gly Pro Tyr Asp Ala
                340                 345                 350

Met Asn Arg Gly Val Gly Val Ala Thr Gly Glu Trp Val Leu Phe Leu
            355                 360                 365

Gly Ala Asp Asp Thr Leu Tyr Glu Pro Thr Thr Leu Ala Gln Val Ala
        370                 375                 380

Ala Phe Leu Gly Asp His Ala Ala Ser His Leu Val Tyr Gly Asp Val
385                 390                 395                 400

Val Met Arg Ser Thr Lys Ser Arg His Ala Gly Pro Phe Asp Leu Asp
                    405                 410                 415

Arg Leu Leu Phe Glu Thr Asn Leu Cys His Gln Ser Ile Phe Tyr Arg
                420                 425                 430

Arg Glu Leu Phe Asp Gly Ile Gly Pro Tyr Asn Leu Arg Tyr Arg Val
            435                 440                 445

Trp Ala Asp Trp Asp Phe Asn Ile Arg Cys Phe Ser Asn Pro Ala Leu
        450                 455                 460

Ile Thr Arg Tyr Met Asp Val Val Ile Ser Glu Tyr Asn Asp Met Thr
465                 470                 475                 480

Gly Phe Ser Met Arg Gln Gly Thr Asp Lys Glu Phe Arg Lys Arg Leu
                    485                 490                 495

Pro Met Tyr Phe Trp Val Ala Gly Trp Glu Thr Cys Arg Arg Met Leu
                500                 505                 510

Ala Phe Leu Lys Asp Lys Glu Asn Arg Arg Leu Ala Leu Arg Thr Arg
            515                 520                 525

Leu Ile Arg Val Lys Ala Val Ser Lys Glu Arg Ser Ala Glu Pro Arg
        530                 535                 540

Ile Arg Arg His Arg His Ala Glu Ile Ile Leu Ser Met Pro Gly Phe
545                 550                 555                 560

Gly Val Ile Leu Gly Ala Glu Phe Leu Ala Ala Thr Gly Gly Asp Met
                    565                 570                 575

Ala Ala Phe Ala Ser Ala Asp Arg Leu Ala Gly Val Ala Gly Leu Ala
                580                 585                 590

Pro Val Pro Arg Asp Ser Gly Arg Ile Ser Gly Asn Leu Lys Arg Pro
            595                 600                 605

Arg Arg Tyr Asp Arg Arg Leu Leu Arg Ala Cys Val Ser Ile Arg Thr
        610                 615                 620

Asp Pro Ser Ser Arg Thr Tyr Tyr Asp Arg Lys Arg Thr Glu Gly Lys
625                 630                 635                 640
```

-continued

```
Arg His Thr Gln Ala Val Leu Ala Leu Ala Arg Arg Leu Asn Val
                645                 650                 655

Leu Trp Ala Met Leu Arg Asp His Ala Val Tyr His Pro Ala Thr Thr
            660                 665                 670

Thr Ala Ala Ala Arg Leu Lys Leu Arg Arg Gly Glu Arg Pro Met Ser
                675                 680                 685

Leu Gly Gln Val Phe Asp Pro Arg Ala Asn Ala Leu His Ser Phe Pro
            690                 695                 700

Leu Thr Gly Arg Met Pro Trp Ala Pro Phe Ile Val Ser Ser Trp Leu
705                 710                 715                 720

Arg Asn Pro His Pro Ala Gln Tyr Phe Thr Ala Arg Cys Leu Arg Ile
                725                 730                 735

Leu Pro Gly Leu Trp Ile Gly Ala Gln Gly Gly Ser Ala Ala Lys Leu
            740                 745                 750

Leu Met Ser Gly Ala Pro Ile Glu Tyr Val Leu Lys Asp Ser Ala Val
                755                 760                 765

Trp Met Phe Lys Phe Asp Ile Gly Gly Thr Pro Arg Asp Ile Pro Val
            770                 775                 780

Ala Gly Ile Trp Asn Gly Ser Leu Trp Thr Pro Ala Trp Gly Gly Ile
785                 790                 795                 800

His Ala Ile Ala Ser Asn Ala Tyr Gln Phe Arg Asn Val Ile Pro Ala
                805                 810                 815

Arg Trp Ser Val Ser Ser Ala Val Leu Pro Asn Tyr Arg Leu Val Ala
            820                 825                 830

Ala Leu Pro Met Ala Tyr His Asn Gln Arg Met Arg Phe Arg Thr Asp
                835                 840                 845

Leu Ser Tyr Gly Val Tyr Gly Phe Ala Glu Ile Asn Pro Ile Ala Leu
            850                 855                 860

Val Glu Lys Pro Ala Leu Ser Trp Lys Ser Arg Leu Arg Arg Lys Asn
865                 870                 875                 880

Ser Ser Ile Ala Leu Ala Asn Met Glu Asp Gly Gly Ser Val Gly Arg
                885                 890                 895

Ser Asn Asp Ile Pro Gly Arg Arg Ala Arg Phe Ile Gly Glu Lys Ala
            900                 905                 910

Glu Asp Pro Pro Ala Pro Ser Pro Arg Pro Ala Leu Arg Ile Pro Asn
                915                 920                 925

Pro Leu Leu Gly Leu Asp
            930

<210> SEQ ID NO 70
<211> LENGTH: 9
<212> TYPE: PRT
<213> ORGANISM: Artificial Sequence
<220> FEATURE:
<223> OTHER INFORMATION: a 2A peptide fragment
<220> FEATURE:
<221> NAME/KEY: misc_feature
<222> LOCATION: (5)..(5)
<223> OTHER INFORMATION: Xaa can be any naturally occurring amino acid

<400> SEQUENCE: 70

Gly Asp Val Glu Xaa Asn Pro Gly Pro
1               5

<210> SEQ ID NO 71
<211> LENGTH: 24
<212> TYPE: PRT
```

```
<213> ORGANISM: Artificial Sequence
<220> FEATURE:
<223> OTHER INFORMATION: a 2A peptide

<400> SEQUENCE: 71

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 72
<211> LENGTH: 4
<212> TYPE: PRT
<213> ORGANISM: Artificial Sequence
<220> FEATURE:
<223> OTHER INFORMATION: peptide fragment

<400> SEQUENCE: 72

Met Thr Val Thr
1

<210> SEQ ID NO 73
<211> LENGTH: 10
<212> TYPE: PRT
<213> ORGANISM: Artificial Sequence
<220> FEATURE:
<223> OTHER INFORMATION: Synthetic peptide

<400> SEQUENCE: 73

Val Asp Ala Gly Lys Ala Asp His Tyr Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: leader sequence

<400> SEQUENCE: 74

Met Gln Ile Phe Val Lys Leu
1               5

<210> SEQ ID NO 75
<211> LENGTH: 13
<212> TYPE: PRT
<213> ORGANISM: Artificial Sequence
<220> FEATURE:
<223> OTHER INFORMATION: peptide tag

<400> SEQUENCE: 75

Pro Ala Leu Arg Ile Pro Asn Pro Leu Leu Gly Leu Asp
1               5                   10

<210> SEQ ID NO 76
<211> LENGTH: 9
<212> TYPE: PRT
<213> ORGANISM: Artificial Sequence
<220> FEATURE:
<223> OTHER INFORMATION: Mpa T cell epitope

<400> SEQUENCE: 76

Gly Phe Ala Glu Ile Asn Pro Ile Ala
1               5

<210> SEQ ID NO 77
```

```
<211> LENGTH: 4
<212> TYPE: PRT
<213> ORGANISM: Artificial Sequence
<220> FEATURE:
<223> OTHER INFORMATION: peptide linker

<400> SEQUENCE: 77

Ser Gly Ser Gly
1

<210> SEQ ID NO 78
<211> LENGTH: 4
<212> TYPE: PRT
<213> ORGANISM: Artificial Sequence
<220> FEATURE:
<223> OTHER INFORMATION: peptide linker

<400> SEQUENCE: 78

Gly Gly Gly Ser
1

<210> SEQ ID NO 79
<211> LENGTH: 5
<212> TYPE: PRT
<213> ORGANISM: Artificial Sequence
<220> FEATURE:
<223> OTHER INFORMATION: peptide linker

<400> SEQUENCE: 79

Glu Ala Ala Ala Lys
1               5

<210> SEQ ID NO 80
<211> LENGTH: 12
<212> TYPE: PRT
<213> ORGANISM: Artificial Sequence
<220> FEATURE:
<223> OTHER INFORMATION: peptide linker

<400> SEQUENCE: 80

His Glu Tyr Gly Ala Glu Ala Leu Glu Arg Ala Gly
1               5                   10

<210> SEQ ID NO 81
<211> LENGTH: 15
<212> TYPE: PRT
<213> ORGANISM: Artificial Sequence
<220> FEATURE:
<223> OTHER INFORMATION: Synthetic peptide

<400> SEQUENCE: 81

Tyr Leu Ser Ala Leu Val Ser Ile Arg Thr Asp Pro Ser Ser Arg
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (14)..(14)
<223> OTHER INFORMATION: PHOSPHORYLATION

<400> SEQUENCE: 82

Tyr Leu Ser Ala Leu Val Ser Ile Arg Thr Asp Pro Ser Ser Arg
1               5                   10                  15
```

```
<210> SEQ ID NO 83
<211> LENGTH: 106
<212> TYPE: PRT
<213> ORGANISM: Artificial Sequence
<220> FEATURE:
<223> OTHER INFORMATION: vaccine polypeptide

<400> SEQUENCE: 83

Met Thr Val Thr Glu Val Val Ala Gln Pro Val Trp Ala Gly Val
1               5                   10                  15

Asp Ala Gly Lys Ala Asp His Tyr Cys Met Val Ile Asn Asp Ala
                20                  25                  30

Gln Arg Leu Leu Ser Gln Arg Val Ala Asn Asp Glu Ala Ala Leu Leu
            35                  40                  45

Glu Leu Ile Ala Ala Val Thr Thr Leu Ala Asp Gly Gly Glu Val Thr
        50                  55                  60

Trp Ala Ile Asp Leu Asn Ala Gly Gly Ala Ala Leu Leu Ile Ala Leu
65                  70                  75                  80

Leu Ile Ala Ala Gly Gln Arg Leu Leu Tyr Ile Pro Gly Ala Thr Val
                85                  90                  95

His His Ala Ala Gly Ser Tyr Arg Gly Glu
            100                 105

<210> SEQ ID NO 84
<211> LENGTH: 77
<212> TYPE: PRT
<213> ORGANISM: Artificial Sequence
<220> FEATURE:
<223> OTHER INFORMATION: vaccine polypeptide

<400> SEQUENCE: 84

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
                20                  25                  30

Glu Val Thr Trp Ala Ile Asp Leu Asn Ala Gly Gly Ala Ala Leu Leu
            35                  40                  45

Ile Ala Leu Leu Ile Ala Ala Gly Gln Arg Leu Leu Tyr Ile Pro Gly
        50                  55                  60

Ala Thr Val His His Ala Ala Gly Ser Tyr Arg Gly Glu
65                  70                  75

<210> SEQ ID NO 85
<211> LENGTH: 15
<212> TYPE: PRT
<213> ORGANISM: Mycobacterium avium paratuberculosis

<400> SEQUENCE: 85

Glu Leu Ile Ala Ala Val Thr Thr Leu Ala Asp Gly Gly Glu Val
1               5                   10                  15

<210> SEQ ID NO 86
<211> LENGTH: 15
<212> TYPE: PRT
<213> ORGANISM: Mycobacterium avium paratuberculosis

<400> SEQUENCE: 86

Asp Arg Lys Arg Thr Glu Gly Lys Arg His Thr Gln Ala Val Leu
1               5                   10                  15
```

<210> SEQ ID NO 87
<211> LENGTH: 15
<212> TYPE: PRT
<213> ORGANISM: Mycobacterium avium paratuberculosis

<400> SEQUENCE: 87

```
Asn Lys Ser Arg Ala Ala Leu Ile Leu Leu Thr Gly Tyr Gln Thr
1               5                   10                  15
```

<210> SEQ ID NO 88
<211> LENGTH: 15
<212> TYPE: PRT
<213> ORGANISM: Mycobacterium avium paratuberculosis

<400> SEQUENCE: 88

```
Ala Lys Glu Val Met Ala Leu Asp Thr Glu Ile Gly Asp Thr Asp
1               5                   10                  15
```

<210> SEQ ID NO 89
<211> LENGTH: 15
<212> TYPE: PRT
<213> ORGANISM: Mycobacterium avium paratuberculosis

<400> SEQUENCE: 89

```
Ala Leu Asp Thr Glu Ile Gly Asp Thr Asp Ala Met Ile Glu Glu
1               5                   10                  15
```

<210> SEQ ID NO 90
<211> LENGTH: 40
<212> TYPE: PRT
<213> ORGANISM: Mycobacterium avium paratuberculosis

<400> SEQUENCE: 90

```
Gly Arg Ile Ser Gly Asn Leu Lys Arg Pro Arg Arg Tyr Asp Arg Arg
1               5                   10                  15

Leu Leu Arg Ala Cys Tyr Leu Ser Ala Leu Val Ser Ile Arg Thr Asp
            20                  25                  30

Pro Ser Ser Arg Thr Tyr Tyr Asp
        35                  40
```

<210> SEQ ID NO 91
<211> LENGTH: 18
<212> TYPE: PRT
<213> ORGANISM: Mycobacterium avium paratuberculosis

<400> SEQUENCE: 91

```
Asn Lys Ser Arg Ala Ala Leu Ile Leu Leu Thr Gly Tyr Gln Thr Pro
1               5                   10                  15

Asp Ala
```

<210> SEQ ID NO 92
<211> LENGTH: 18
<212> TYPE: PRT
<213> ORGANISM: Mycobacterium avium paratuberculosis

<400> SEQUENCE: 92

```
Asn Leu Lys Arg Pro Arg Arg Tyr Asp Arg Arg Leu Leu Arg Ala Gly
1               5                   10                  15

Tyr Leu
```

<210> SEQ ID NO 93
<211> LENGTH: 10

<212> TYPE: PRT
<213> ORGANISM: Mycobacterium avium paratuberculosis

<400> SEQUENCE: 93

Met Val Ile Asn Asp Asp Ala Gln Arg Leu
1               5                   10

<210> SEQ ID NO 94
<211> LENGTH: 11
<212> TYPE: PRT
<213> ORGANISM: Mycobacterium avium paratuberculosis

<400> SEQUENCE: 94

Met Val Ile Asn Asp Asp Ala Gln Arg Leu Cys
1               5                   10

<210> SEQ ID NO 95
<211> LENGTH: 11
<212> TYPE: PRT
<213> ORGANISM: Mycobacterium avium paratuberculosis

<400> SEQUENCE: 95

Cys Asn Leu Lys Arg Pro Arg Arg Tyr Asp Arg
1               5                   10

<210> SEQ ID NO 96
<211> LENGTH: 11
<212> TYPE: PRT
<213> ORGANISM: Mycobacterium avium paratuberculosis

<400> SEQUENCE: 96

Cys Val Ser Ile Arg Thr Asp Pro Ser Ser Arg
1               5                   10

<210> SEQ ID NO 97
<211> LENGTH: 15
<212> TYPE: PRT
<213> ORGANISM: Mycobacterium avium paratuberculosis

<400> SEQUENCE: 97

Met Val Ile Asn Asp Asp Ala Gln Arg Leu Leu Ser Gln Arg Cys
1               5                   10                  15

<210> SEQ ID NO 98
<211> LENGTH: 16
<212> TYPE: PRT
<213> ORGANISM: Mycobacterium avium paratuberculosis

<400> SEQUENCE: 98

Val Thr Thr Leu Ala Asp Gly Gly Glu Val Thr Trp Ala Ile Asp Cys
1               5                   10                  15

<210> SEQ ID NO 99
<211> LENGTH: 16
<212> TYPE: PRT
<213> ORGANISM: Mycobacterium avium paratuberculosis

<400> SEQUENCE: 99

Tyr Leu Ser Ala Leu Val Ser Ile Arg Thr Asp Pro Ser Ser Arg Cys
1               5                   10                  15

<210> SEQ ID NO 100
<211> LENGTH: 10
<212> TYPE: PRT
<213> ORGANISM: Mycobacterium avium paratuberculosis

```
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: 8branchedPolylysineOctamer

<400> SEQUENCE: 100

Met Val Ile Asn Asp Asp Ala Gln Arg Leu
1               5                   10

<210> SEQ ID NO 101
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 101

Met Val Ile Asn Asp Asp Ala Gln Arg Leu
1               5                   10

<210> SEQ ID NO 102
<211> LENGTH: 9
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (9)..(9)
<223> OTHER INFORMATION: AMIDATION

<400> SEQUENCE: 102

Met Val Ile Asn Asp Asp Leu Gln Arg
1               5

<210> SEQ ID NO 103
<211> LENGTH: 8
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (8)..(8)
<223> OTHER INFORMATION: AMIDATION

<400> SEQUENCE: 103

Met Val Ile Asn Asn Asp Ala Glu
1               5

<210> SEQ ID NO 104
<211> LENGTH: 11
<212> TYPE: PRT
<213> ORGANISM: Mycobacterium avium paratuberculosis
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (11)..(11)
<223> OTHER INFORMATION: 8branchedPolylysineOctamer

<400> SEQUENCE: 104

Val Thr Thr Leu Ala Asp Gly Gly Glu Val Thr
1               5                   10

<210> SEQ ID NO 105
<211> LENGTH: 11
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (11)..(11)
<223> OTHER INFORMATION: AMIDATION

<400> SEQUENCE: 105

Val Thr Thr Leu Ala Asp Gly Gly Glu Val Thr
1               5                   10

<210> SEQ ID NO 106
<211> LENGTH: 11
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (11)..(11)
<223> OTHER INFORMATION: AMIDATION

<400> SEQUENCE: 106

Val Ala Thr Met Ala Asp Gly Gly Glu Val Thr
1               5                   10

<210> SEQ ID NO 107
<211> LENGTH: 11
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (11)..(11)
<223> OTHER INFORMATION: AMIDATION

<400> SEQUENCE: 107

Val Thr Arg Leu Ala Asp Gly Gly Glu Val Thr
1               5                   10

<210> SEQ ID NO 108
<211> LENGTH: 10
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
```

```
<222> LOCATION: (10)..(10)
<223> OTHER INFORMATION: 8branchedPolylysineOctamer

<400> SEQUENCE: 108

Asn Leu Lys Arg Pro Arg Arg Tyr Asp Arg
1               5                   10

<210> SEQ ID NO 109
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 109

Asn Leu Lys Arg Pro Arg Arg Tyr Asp Arg
1               5                   10

<210> SEQ ID NO 110
<211> LENGTH: 7
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (7)..(7)
<223> OTHER INFORMATION: AMIDATION

<400> SEQUENCE: 110

Asn Leu Lys Arg Pro Arg Arg
1               5

<210> SEQ ID NO 111
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: ACETYLATION

<400> SEQUENCE: 111

Asn Leu Arg Arg Pro Arg Arg Tyr His Arg
1               5                   10

<210> SEQ ID NO 112
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION
```

<400> SEQUENCE: 112

Asn Leu His Arg Pro Arg Arg Tyr His Arg
1               5                   10

<210> SEQ ID NO 113
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 113

Asn Met Arg Arg Pro Arg Arg Tyr Asn Arg
1               5                   10

<210> SEQ ID NO 114
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 114

Asn Leu Arg Arg Pro Lys Arg Tyr Asn Arg
1               5                   10

<210> SEQ ID NO 115
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 115

Asn Leu Gln Arg Pro Arg Arg Tyr Asn Arg
1               5                   10

<210> SEQ ID NO 116
<211> LENGTH: 10
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (10)..(10)
<223> OTHER INFORMATION: 8branchedPolylysineOctamer

<400> SEQUENCE: 116

Val Ser Ile Arg Thr Asp Pro Ser Ser Arg

```
1               5                    10

<210> SEQ ID NO 117
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 117

Val Ser Ile Arg Thr Asp Pro Ser Ser Arg
1               5                    10

<210> SEQ ID NO 118
<211> LENGTH: 7
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: biotinyl
<220> FEATURE:
<221> NAME/KEY: MOD_RES
<222> LOCATION: (7)..(7)
<223> OTHER INFORMATION: AMIDATION

<400> SEQUENCE: 118

Val Ser Ile Arg Thr Asp Pro
1               5

<210> SEQ ID NO 119
<211> LENGTH: 9
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (9)..(9)
<223> OTHER INFORMATION: AMIDATION

<400> SEQUENCE: 119

Ser Ile Arg Ser Asp Pro Ser Ser Arg
1               5

<210> SEQ ID NO 120
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 120

Tyr Ser Ile Arg Ser Asp Pro Ala Ser Arg
1               5                    10
```

```
<210> SEQ ID NO 121
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 121

Val Ser Val Arg Tyr Asp Pro Ser Ser Arg
1               5                   10

<210> SEQ ID NO 122
<211> LENGTH: 10
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (10)..(10)
<223> OTHER INFORMATION: AMIDATION

<400> SEQUENCE: 122

Ile Ala Ile Arg Thr Asp Pro Ala Ser Arg
1               5                   10

<210> SEQ ID NO 123
<211> LENGTH: 11
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION

<400> SEQUENCE: 123

Met Val Ile Asn Asp Asp Ala Gln Arg Leu Cys
1               5                   10

<210> SEQ ID NO 124
<211> LENGTH: 12
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION

<400> SEQUENCE: 124

Val Thr Thr Leu Ala Asp Gly Gly Glu Val Thr Cys
1               5                   10

<210> SEQ ID NO 125
<211> LENGTH: 11
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION

<400> SEQUENCE: 125
```

```
Asn Leu Lys Arg Pro Arg Arg Tyr Asp Arg Cys
1               5                   10
```

<210> SEQ ID NO 126
<211> LENGTH: 11
<212> TYPE: PRT
<213> ORGANISM: Mycobacterium avium paratuberculosis
<220> FEATURE:
<221> NAME/KEY: MOD_RES
<222> LOCATION: (1)..(1)
<223> OTHER INFORMATION: ACETYLATION

<400> SEQUENCE: 126

```
Val Ser Ile Arg Thr Asp Pro Ser Ser Arg Cys
1               5                   10
```

<210> SEQ ID NO 127
<211> LENGTH: 15
<212> TYPE: PRT
<213> ORGANISM: Mycobacterium avium paratuberculosis
<220> FEATURE:
<221> NAME/KEY: MOD_RES
<222> LOCATION: (15)..(15)
<223> OTHER INFORMATION: AMIDATION

<400> SEQUENCE: 127

```
Cys Met Val Ile Asn Asp Asp Ala Gln Arg Leu Leu Ser Gln Arg
1               5                   10                  15
```

<210> SEQ ID NO 128
<211> LENGTH: 14
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: AMIDATION

<400> SEQUENCE: 128

```
Met Val Ile Asn Asp Asp Ala Gln Arg Leu Leu Ser Gln Arg
1               5                   10
```

<210> SEQ ID NO 129
<211> LENGTH: 14
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: AMIDATION

<400> SEQUENCE: 129

```
Met Val Ile Asn Asp Asp Leu Gln Arg Ile Ile Leu Phe Leu
1               5                   10
```

<210> SEQ ID NO 130
<211> LENGTH: 14
<212> TYPE: PRT
<213> ORGANISM: Mycobacterium avium paratuberculosis
<220> FEATURE:
<221> NAME/KEY: MISC_FEATURE
<222> LOCATION: (1)..(1)

```
<223> OTHER INFORMATION: Biotinyl
<220> FEATURE:
<221> NAME/KEY: MOD_RES
<222> LOCATION: (14)..(14)
<223> OTHER INFORMATION: AMIDATION

<400> SEQUENCE: 130

Met Ser Ile Asn Asp Asp Ala Gln Lys Leu Lys Asp Arg Leu
1               5                   10

<210> SEQ ID NO 131
<211> LENGTH: 15
<212> TYPE: PRT
<213> ORGANISM: Mycobacterium avium paratuberculosis
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MISC_FEATURE
<222> LOCATION: (15)..(15)
<223> OTHER INFORMATION: Amide BSA conjugated

<400> SEQUENCE: 131

Cys Met Val Ile Asn Asp Asp Ala Gln Arg Leu Leu Ser Gln Arg
1               5                   10                  15

<210> SEQ ID NO 132
<211> LENGTH: 14
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (14)..(14)
<223> OTHER INFORMATION: AMIDATION

<400> SEQUENCE: 132

Met Val Ile Asn Asp Asp Ala Gln Arg Leu Leu Ser Gln Arg
1               5                   10

<210> SEQ ID NO 133
<211> LENGTH: 14
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: AMIDATION

<400> SEQUENCE: 133

Met Val Ile Asn Asp Asp Ala Gln Arg Leu Leu Ser Gln Arg
1               5                   10

<210> SEQ ID NO 134
<211> LENGTH: 21
<212> TYPE: PRT
<213> ORGANISM: Mycobacterium avium paratuberculosis
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MISC_FEATURE
<222> LOCATION: (21)..(21)
<223> OTHER INFORMATION: BSA conjugated

<400> SEQUENCE: 134

Ala Ala Val Thr Thr Leu Ala Asp Gly Gly Glu Val Thr Trp Ala Ile
1               5                   10                  15

Asp Gly Lys Lys Cys
            20

<210> SEQ ID NO 135
<211> LENGTH: 20
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (20)..(20)
<223> OTHER INFORMATION: AMIDATION

<400> SEQUENCE: 135

Lys Lys Gly Ala Ala Val Thr Thr Leu Ala Asp Gly Gly Glu Val Thr
1               5                   10                  15

Trp Ala Ile Asp
            20

<210> SEQ ID NO 136
<211> LENGTH: 20
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (20)..(20)
<223> OTHER INFORMATION: AMIDATION

<400> SEQUENCE: 136

Lys Lys Gly Ala Ala Gly Thr Thr Leu Ala Asp Gly Gly Glu Val Thr
1               5                   10                  15

Trp Ala Ile Asp
            20

<210> SEQ ID NO 137
<211> LENGTH: 20
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (20)..(20)
<223> OTHER INFORMATION: AMIDATION

<400> SEQUENCE: 137

Lys Lys Gly Ser Thr Val Ala Thr Met Ala Asp Gly Gly Glu Val Thr
1               5                   10                  15

Trp Ala Ile Asp
```

```
<210> SEQ ID NO 138
<211> LENGTH: 20
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (20)..(20)
<223> OTHER INFORMATION: AMIDATION

<400> SEQUENCE: 138

Lys Lys Gly Gln Ala Val Thr Arg Leu Ala Asp Gly Gly Glu Val Thr
1               5                   10                  15

Trp Ala Val Asp
            20

<210> SEQ ID NO 139
<211> LENGTH: 20
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (20)..(20)
<223> OTHER INFORMATION: AMIDATION

<400> SEQUENCE: 139

Lys Lys Gly Phe Glu Val Thr Thr Leu Ala Asp Gly Thr Glu Val Ala
1               5                   10                  15

Thr Ser Pro Leu
            20

<210> SEQ ID NO 140
<211> LENGTH: 16
<212> TYPE: PRT
<213> ORGANISM: Mycobacterium avium paratuberculosis
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MISC_FEATURE
<222> LOCATION: (16)..(16)
<223> OTHER INFORMATION: Amide BSA conjugated

<400> SEQUENCE: 140

Cys Tyr Leu Ser Ala Leu Val Ser Ile Arg Thr Asp Pro Ser Ser Arg
1               5                   10                  15

<210> SEQ ID NO 141
<211> LENGTH: 15
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: PHOSPHORYLATION
<220> FEATURE:
```

```
<221> NAME/KEY: MOD_RES
<222> LOCATION: (15)..(15)
<223> OTHER INFORMATION: AMIDATION

<400> SEQUENCE: 141

Tyr Leu Ser Ala Leu Val Ser Ile Arg Thr Asp Pro Ser Ser Arg
1               5                   10                  15

<210> SEQ ID NO 142
<211> LENGTH: 15
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (15)..(15)
<223> OTHER INFORMATION: AMIDATION

<400> SEQUENCE: 142

Tyr Leu Ser Ala Leu Val Ser Ile Arg Thr Asp Pro Ser Ser Arg
1               5                   10                  15

<210> SEQ ID NO 143
<211> LENGTH: 15
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (15)..(15)
<223> OTHER INFORMATION: AMIDATION

<400> SEQUENCE: 143

Tyr Leu Ser Ala Leu Tyr Ser Ile Arg Ser Asp Pro Ala Ser Arg
1               5                   10                  15

<210> SEQ ID NO 144
<211> LENGTH: 15
<212> TYPE: PRT
<213> ORGANISM: Mycobacterium avium paratuberculosis
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (15)..(15)
<223> OTHER INFORMATION: AMIDATION

<400> SEQUENCE: 144

Tyr Leu Ser Ala Leu Val Ser Val Arg Tyr Asp Pro Ser Ser Arg
1               5                   10                  15

<210> SEQ ID NO 145
<211> LENGTH: 15
<212> TYPE: PRT
<213> ORGANISM: Mycobacterium avium paratuberculosis
```

```
<220> FEATURE:
<221> NAME/KEY: MISC_FEATURE
<222> LOCATION: (1)..(1)
<223> OTHER INFORMATION: Biotinyl
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (15)..(15)
<223> OTHER INFORMATION: AMIDATION

<400> SEQUENCE: 145

Tyr Leu Ser Ala Gln Ile Ala Ile Arg Thr Asp Pro Ala Ser Arg
1               5                   10                  15

<210> SEQ ID NO 146
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 146

Met Val Ile Asn Asp Asp Ala Gln Arg Leu Leu Ser Gln Arg Val Asp
1               5                   10                  15

Ala Gly Lys Ala Asp His Tyr Ala Val Thr Thr Leu Ala Asp Gly Gly
            20                  25                  30

Glu Val Thr Trp Ala Ile Asp Leu Asn Ala
            35                  40
```

IMMUNOGENIC COMPOSITION FOR PARATUBERCULOSIS

CROSS REFERENCE TO RELATED APPLICATIONS

This application is a national stage application under 35 U.S.C. 371 and claims the benefit of PCT Application No. PCT/GB2019/051933 having an international filing date of 10 Jul. 2019, which designated the United States, which PCT application claimed the benefit of Great Britain Patent Application No. 1811382.9 filed 11 Jul. 2018, the disclosures of each of which are incorporated herein by reference in their entireties.

REFERENCE TO SEQUENCE LISTING

This application contains a Sequence Listing submitted as an electronic text file named "Sequence_Listing_N413293US.txt", having a size in bytes of 154000 bytes, and created on 15 Jun. 2021. The information contained in this electronic file is hereby incorporated by reference in its entirety pursuant to 37 CFR § 1.52 (e)(5).

FIELD OF THE INVENTION

The present invention relates to the treatment or prevention of infection with *Mycobacterium avium* subspecies paratuberculosis (MAP), and to the treatment or prevention of disorders associated with MAP infection.

BACKGROUND TO THE INVENTION

MAP is a very slow growing intracellular mycobacterial pathogen which can cause systemic infection and chronic inflammation of the intestine (Johne's disease (JD)) in many animal species including primates. MAP was first identified in a sick dairy cow in Germany in 1894. In subsequent years MAP infection and disease appeared to be limited to Europe and North America. Since then it has spread worldwide due to international trade in subclinically infected domestic livestock and the absence of a reliable sensitive diagnostic technology able to identify MAP infection in its earliest stage. The MAP genome is GC rich (69.3%) and shares 96.4% homology in sequence and genetic organisation with closely related *Mycobacterium avium* and other bacteria abundant in the environment and microbiomes of animals and humans (Li et al. PNAS 2005; 102:12344-9).

MAP infected animals shed these organisms onto pastures. In pluribacillary disease the MAP pathogens in their faeces are in their common bacillary form with established red-staining Ziehl-Neelsen coats visible microscopically. Humans appear to be less susceptible to this bacillary form of MAP which is also the one commonly used in conventional partially effective whole-killed MAP vaccines. Studies have shown that exposure of children in early life to MAP-infected farm animals particularly cattle can result in a significant reduction in the subsequent incidence of Crohn's disease (Cucino C, Sonnenberg A. (2001) Am J Gastroenterol. 96:1101-5. Radon K. et al (2007) Paediatrics; 120:354-61).

Within the body of the infected animal itself MAP is present intracellularly. This form appears more aggressive to humans so that infected animal cells in milk and dairy products and meat are a source of repeated MAP infection and long term colonisation. Furthermore, MAP is a tough environmental organism and its destruction by pasteurization is incomplete. Humans are therefore at risk in dairy products from cattle, sheep and goats.

MAP survives on pastures and is taken up by protists in which intracellular environment they can survive for months or years. These organisms infect wildlife such as rabbits whose MAP-laden faeces are taken up again by grazing cattle. MAP from dead infected animals is also spread by carrion feeders. Culling of infected animals and restocking after an interval with healthy livestock merely results in the return of chronic MAP infection. Rainfall washes MAP into rivers from which MAP can spread by aerosols and directly by domestic water supplies (Richardson et al. 2019 Microorganisms 7, 136).

Once MAP becomes established in farm animals and their environment it remains and is consistently followed after an interval by the emergence and rise of Crohn's disease in the human population. The main reservoir of MAP infection is the continual replenishment of environmental sources of MAP from infected livestock. The control and subsequent reversal of the global MAP problem therefore relies on the recognition of its existence and the availability of effective vaccines which can block faecal shedding and reduce or eliminate chronic MAP infection in animals and humans. Data obtained by the U.S. department of agriculture predicts that 91.1% of U.S. dairy herds are infected with MAP (Lombard J E et al. (2013) Preventive Veterinary Medicine 108: 234-238).

The IS900 element was identified and characterised in the late 1980s (Green et al. (1989) Nucleic Acids Res; 17:9063-73). It was the first of a group of related but different DNA insertion elements found in MAP and closely related *Mycobacterium avium*. MAP is the only known organism with 14 to 18 identical copies of IS900. MAP is also the only pathogen known to cause chronic inflammatory diseases in so many species including primates.

A virally vectored anti-MAP vaccine has been developed by HAV Vaccines Ltd with Oxford University Jenner Institute providing the hAd5 and ChAdOx2 adenoviral priming and MVA boosting vectors containing the HAV vaccine insert (Bull et al. 2007 PLoS ONE 2(11): e1229; Bull et al. 2014 Veterinary Research 45:112). HAV Vaccines Ltd designed and made the 'HAV' vaccine insert, which is described in WO 2007/017635. and comprises a 95 kDa fusion construct from 4 MAP genes 1589c (AhpC), 1234 (Gsd), 2444c (p12) and 1235 (mpa) present in all MAP strains. AhpC is a secreted virulence factor in MAP shared by other pathogenic mycobacteria. Gsd is directly involved in the synthesis and transport of fucose contributing to MAP's relatively inert and highly chemical and enzymic resistance characteristics. P12 consists mostly of the extracellular carboxyterminal portion of the IS900 protein released from the mycobacterial cell and involved in pathogenicity. Mpa is a cell surface acyltransferase and may have a pore function which contributes to MAP's intrinsic resistance pattern.

Similar sequences are present within all 4 of these MAP genes in the HAV insert, to those in secondary co-pathogens in Crohn's disease, including some *E. coli* and other *M. avium* sp. Overlap of the brisk immunological responses to the HAV insert induced by vaccination are predicted to maximise the efficacy of therapeutic vaccination. The DNA of the selected HAV genes was codon optimised for mammalian cell expression and strung together to express the single HAV vaccine antigen. For patient safety this was further edited to remove any genetic sequences with homology to a mammalian sequence.

Recognition of the reality of MAP infection in humans has been delayed for years by the absence of a practical clinical MAP diagnostic (Nacy C and Buckley M. Report from the American Academy of Microbiology 2008. *Mycobacterium avium* paratuberculosis: Infrequent Human Pathogen or Public Health Threat?).

SUMMARY OF THE INVENTION

The present inventor has surprisingly found that peptide fragments from the N-terminal region of the MAP P900 protein are immunogenic. Using antibodies to such peptide fragments, the inventor has shown that MAP P900 is expressed in MAP-infected human and animal subjects. The inventor has also shown that the MAP 900 protein is cleaved such that the N-terminal extracellular domain and C-terminal extracellular domain do not always co-localise in cells of infected subjects. Furthermore, the inventor has shown that it is possible to produce antibodies that are specific either for a phosphorylated N-terminal peptide or for the non-phosphorylated form of the peptide, with the antibodies being mutually exclusive. Using such phosphorylation-sensitive antibodies, the inventors have shown that the phosphorylation pattern of the N-terminus of P900 differs in infected human gut compared to infected animal gut. In the infected animals, the N-terminus is phosphorylated in the infected gut, whereas in humans, the phosphorylated N-terminus is visible only in blood cells of infected MAP subjects.

The present inventor has developed a new MAP vaccine based on the importance of P900 to MAP, the recognition of its effects on individual infected cells and populations of infected cells including the observed cleavage of the N-terminal extracellular domain and its subsequently separation and differential location to the C-terminal domain of P900. The inventor has shown that peptides within the N-terminal domain are immunogenic. These peptides and longer polypeptides comprising them, as well as polynucleotides encoding these peptides and polypeptides, may be used as vaccines. For example, the inventor has found that these peptides and polypeptides may provide additional expression stimuli in the HAV vaccine described in the art.

Accordingly, the present invention provides a vaccine comprising a polypeptide comprising an amino acid sequence of at least 9 contiguous amino acids from the region of MAP P900 shown in SEQ ID NO: 2, or a polynucleotide encoding said polypeptide, for use in a method of treating or preventing MAP infection or a condition or symptom associated with MAP infection in a subject.

In particular embodiments, the vaccine comprises a polypeptide comprising the amino acid sequence MVINDDAQRLLSQR or a polynucleotide encoding such a polypeptide. The polypeptide comprising the amino acid sequence MVINDDAQRLLSQR may be phosphorylated at the serine residue either in the vaccine composition or after administration of the vaccine to the subject. The vaccine is particularly useful for treating a subject having: Crohn's disease, Johne's disease, Ulcerative Colitis, Psoriasis, Thyroiditis, Sarcoidosis, Parkinson's disease, Multiple Sclerosis, Type 1 Diabetes, arthritis, ankylosing spondylitis, rheumatoid arthritis, irritable bowel syndrome, inflammatory bowel disease, chronic enteritis, Alzheimer's disease, multiple sclerosis, idiopathic pulmonary fibrosis, leprosy and/or chronic fatigue syndrome.

The invention further provides:
a peptide of up to 100 amino acids, which comprises the amino acid sequence:

MVINDDAQRLLSQRVANDEAALLELI.

a polypeptide which comprises the amino acid sequence MVINDDAQRLLSQR and an ahpC polypeptide, a gsd polypeptide, a p12 polypeptide and/or a mpa polypeptide.

a vaccine vector comprising a comprising a polynucleotide encoding a polypeptide comprising an amino acid sequence of at least 9 contiguous amino acids from the region of MAP P900 shown in SEQ ID NO: 2.

a peptide consisting of the amino acid sequence MVINDDAQRLLSQR, or a peptide, polypeptide, polynucleotide or vaccine vector of the invention for use in a method of treating or preventing MAP infection or a condition or symptom associated with MAP infection in a subject.

a method of treating or preventing MAP infection or a condition or symptom associated with MAP infection comprising administering to a subject in need thereof an effective amount of a polypeptide comprising an amino acid sequence of at least 9 contiguous amino acids from the region of MAP P900 shown in SEQ ID NO: 2, a polynucleotide encoding said polypeptide, a peptide consisting of the amino acid sequence MVINDDAQRLLSQR, or a peptide, polypeptide, polynucleotide or vaccine vector of the invention.

a kit for use in treating or preventing MAP infection or a condition or symptom associated with MAP infection, said kit comprising (i) at least one of a polypeptide comprising an amino acid sequence of at least 9 contiguous amino acids from the region of MAP P900 shown in SEQ ID NO: 2, a polynucleotide encoding said polypeptide, a peptide consisting of the amino acid sequence MVINDDAQRLLSQR, or a peptide, polypeptide, polynucleotide or vaccine vector of the invention and (ii) at least one other therapeutic agent, for simultaneous, sequential or separate use.

BRIEF DESCRIPTION OF THE SEQUENCES

Figure 1:
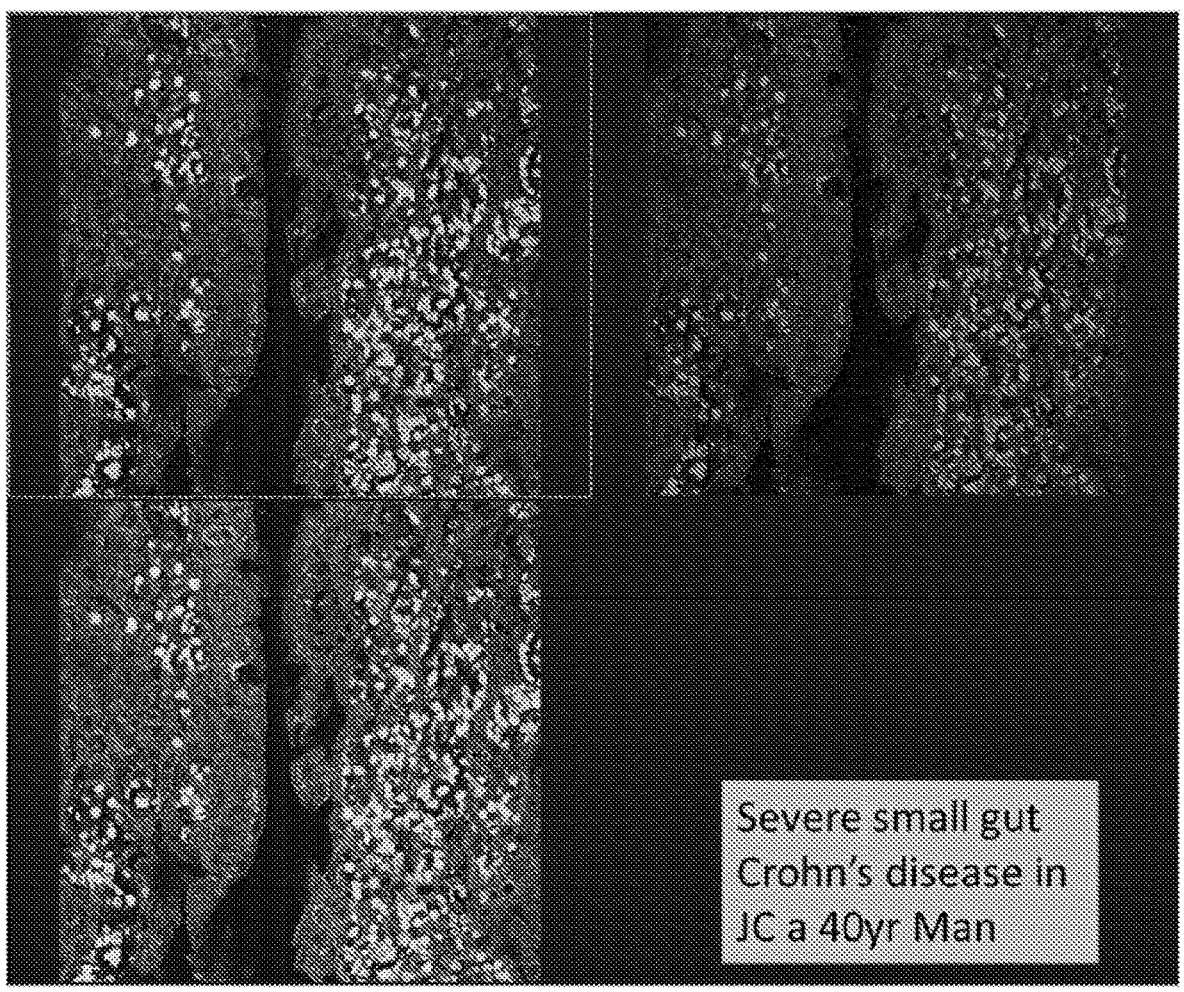
FIG. 1 shows the staining of MAP ISP900 in the ileum in a 40 year old man with Crohn's disease using two specific monoclonal antibodies against *Mycobacterium avium* subspecies paratuberculosis (MAP). These are A1 in red (top right) and A4 in green (top left). The bottom panel shows the two together.
Figure 2:
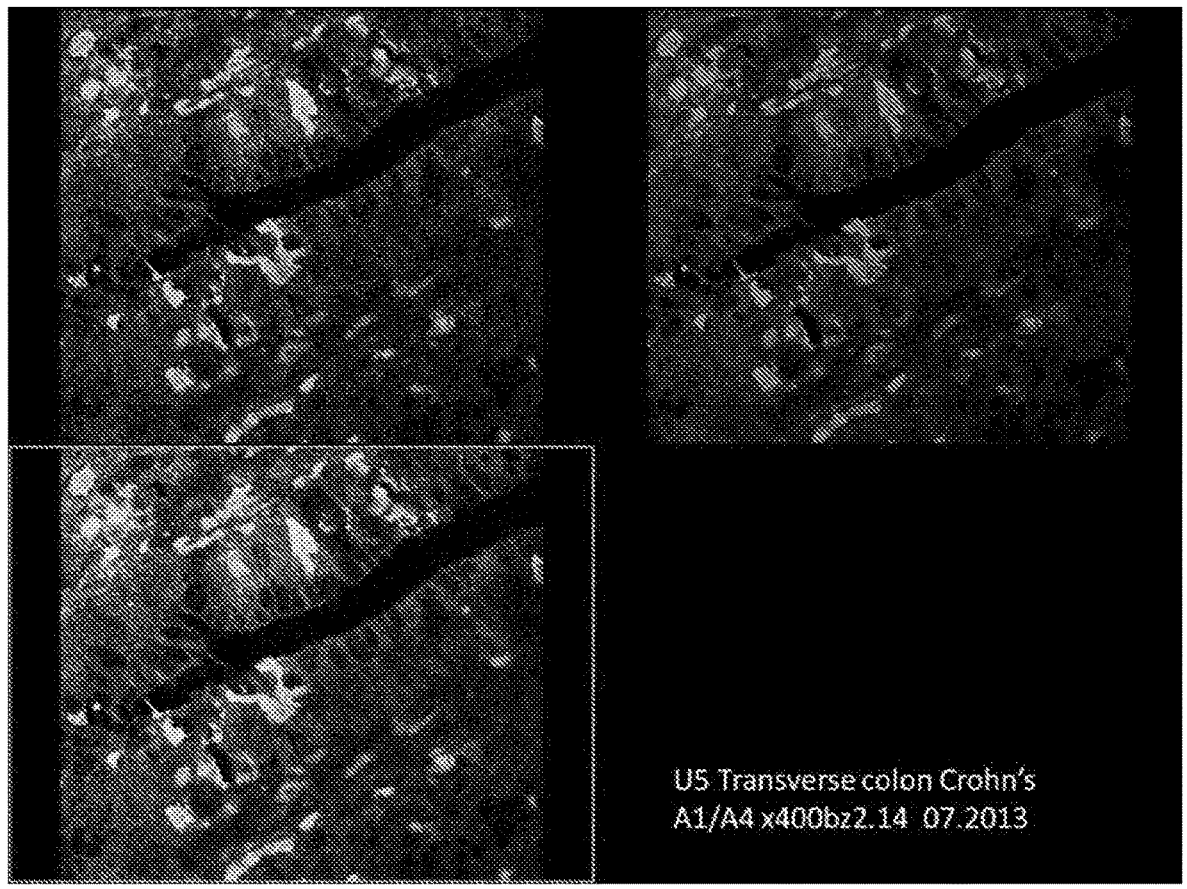
FIG. 2 shows the transverse colon of an individual with Crohn's disease stained using the A1 (red/top right) and A4 antibodies (green/top left). The bottom panel shows the two together.

SEQ ID NOs: 1 and 2 are the nucleic acid and amino acid sequences respectively for the N terminal region of the MAP P900 protein.

SEQ ID NOs: 3 and 4 are the amino acid sequences of the short and long A0X peptides respectively.

SEQ ID NOs: 5 and 6 are the amino acid sequences of the short and long A0X peptides respectively, displaying the phosphorylation sites.

SEQ ID NOs: 7 and 8 are the amino acid sequences of the short and long A1 peptides respectively.

SEQ ID NOs: 9 and 10 are the amino acid sequences of the short and long AN terminal peptides respectively.

SEQ ID NOs: 11 and 12 are the amino acid sequences of the A0X short peptide linked to the A1 short peptide and the A0X short peptide linked to the A1 long peptide respectively.

SEQ ID NOs: 13 and 14 are the amino acid sequences of the A0X long peptide linked to the A1 short peptide and the A0X long peptide linked to the A1 long peptide respectively.

SEQ ID NOs: 15 and 16 are the amino acid sequences of the AN short peptide linked to the A0X short peptide and the AN short peptide linked to the A0X long peptide respectively.

SEQ ID NOs: 17 and 18 are the amino acid sequences of the AN long peptide linked to the A0X short peptide and the AN long peptide linked to the A0X long peptide respectively.

SEQ ID NOs: 19 and 20 are the amino acid sequences of the AN short peptide linked to the A0X long peptide linked to the A1 long peptide and the AN long peptide linked to the A0X long peptide respectively.

SEQ ID NOs: 21 and 22 are the nucleic acid and amino acid sequences respectively for the MAP ahpC gene.

SEQ ID NOs: 23 and 24 are the nucleic acid and amino acid sequences respectively for the MAP gsd gene.

SEQ ID NOs: 25 and 26 are the nucleic acid and amino acid sequences respectively for the MAP p12 gene.

SEQ ID NOs: 27 and 28 are the nucleic acid and amino acid sequences respectively for truncated MAP p12 gene.

SEQ ID NOs: 29 and 30 are the nucleic acid and amino acid sequences respectively for the MAP mpa gene.

SEQ ID NOs: 31 and 32 are the nucleic acid and amino acid sequences respectively of a modified version of the MAP ahpC gene, in which the nucleic acid sequence has been codon optimised for human use.

SEQ ID NOs: 33 and 34 are the nucleic acid and amino acid sequences respectively of a modified version of the MAP gsd gene, in which the nucleic acid sequence has been codon optimised for human use and which is truncated at the N-terminus in order to remove the cysteine residue at position 22.

SEQ ID NOs: 35 and 36 are the nucleic acid and amino acid sequences respectively of a modified version of the MAP p12 gene, in which the nucleic acid sequence has been codon optimised for human use.

SEQ ID NOs: 37 and 38 are the nucleic acid and amino acid sequences respectively of a modified version of the truncated MAP p12 gene, in which the nucleic acid sequence has been codon optimised for human use.

SEQ ID NOs: 39 and 40 are the nucleic acid and amino acid sequences respectively of a modified version of the MAP mpa gene, in which the nucleic acid sequence has been codon optimised for human use and a number of transmembrane regions have been removed.

SEQ ID NO: 41 is the amino acid sequence of an internally truncated HAV vaccine polypeptide.

SEQ ID NO: 42 is the amino acid sequence of the HAV vaccine polypeptide.

SEQ ID NO: 43 is the amino acid sequence of the full length MAP P900 protein.

SEQ ID NO: 44 is the amino acid sequence of the A4 peptide.

SEQ ID NO: 45 is the amino acid sequence of the phosphorylated A4 peptide.

SEQ ID NO: 46 is the amino acid sequence of an alternatively phosphorylated A4 peptide.

SEQ ID NO: 47 is the amino acid sequence of the doubly phosphorylated A4 peptide.

SEQ ID NO: 48 is the amino acid sequence of the A3 peptide.

SEQ ID NO: 49 is the nucleic acid sequence of the HAV vaccine.

SEQ ID NO: 50 is the amino acid sequence of a peptide from the N-terminal region of P900.

SEQ ID NO: 51 is the amino acid sequence of a portion of the extracellular region of P900.

SEQ ID NO: 52 is the amino acid sequence of a polypeptide comprising three peptides from the extracellular region of P900.

SEQ ID NO: 53 is the amino acid sequence of a transmembrane region of P900.

SEQ ID NO: 54 is the amino acid sequence of an intramycobacterial region of P900.

SEQ ID NO: 55 is the amino acid sequence of a variant intramycobacterial region of P900.

SEQ ID NO: 56 is the amino acid sequence of a transmembrane region and an intramycobacterial region of P900.

SEQ ID NO: 57 is the amino acid sequence of a transmembrane region and a variant intramycobacterial region of P900.

SEQ ID NO: 58 is the amino acid sequence of a polypeptide comprising a portion of the extracellular region, a transmembrane region and an intramycobacterial region of P900.

SEQ ID NO: 59 is the amino acid sequence of a polypeptide comprising a portion of the extracellular region, a transmembrane region and a variant intramycobacterial region of P900.

SEQ ID NO: 60 is the amino acid sequence of a polypeptide comprising three peptides from the extracellular region, a transmembrane region and an intramycobacterial region of P900.

SEQ ID NO: 61 is the amino acid sequence of a polypeptide comprising three peptides from the extracellular region, a transmembrane region and a variant intramycobacterial region of P900.

SEQ ID NO: 62 is the amino acid sequence of the HAV vaccine polypeptide with the addition of SEQ ID NO: 59 at the N-terminus.

SEQ ID NO: 63 is the amino acid sequence of the HAVX1 vaccine polypeptide.

SEQ ID NO: 64 is the amino acid sequence of the HAV vaccine polypeptide with the addition of SEQ ID NO: 58 at the N-terminus.

SEQ ID NO: 65 is the amino acid sequence of an internally truncated HAV vaccine polypeptide with the addition of SEQ ID NO: 58 at the N-terminus.

SEQ ID NO: 61 is the amino acid sequence of the HAV vaccine polypeptide with the addition of SEQ ID NO: 59 at the N-terminus.

SEQ ID NO: 63 is the amino acid sequence of the HAVX2 vaccine polypeptide.

SEQ ID NO: 64 is the amino acid sequence of the HAV vaccine polypeptide with the addition of SEQ ID NO: 60 at the N-terminus.

SEQ ID NO: 65 is the amino acid sequence of an internally truncated HAV vaccine polypeptide with the addition of SEQ ID NO: 60 at the N-terminus.

SEQ ID NO: 70 is a consensus amino acid sequence for 2A peptides.

SEQ ID NO: 71 is the amino acid sequence of a 2A peptide.

SEQ ID NOs: 72 to 146 are amino acid sequences of peptides and polypeptides described in the Examples.

DETAILED DESCRIPTION OF THE INVENTION

Vaccine

The invention provides a vaccine comprising a polypeptide comprising an amino acid sequence of at least 9 contiguous amino acids from the region of MAP P900 shown in SEQ ID NO: 2, or a polynucleotide encoding said polypeptide, for use in a method of treating or preventing MAP infection or a condition or symptom associated with MAP infection in a subject.

The polypeptide in the vaccine may comprise, consist of, or consist essentially of from 9 to 71, 10 to 70, 12 to 65, 15 to 60, 18 to 55, 20 to 50, 25 to 45, or 30 to 40 contiguous amino acids of SEQ ID NO: 2.

The polypeptide may comprise two or more stretches of at least 9 contiguous amino acids from SEQ ID NO: 2. For example, the polypeptide may comprise one, two, three or more stretches of 9 or more contiguous amino acids from the amino acid sequence of SEQ ID NO: 2. Each contiguous stretch of amino acids may be a stretch of from 9 to 30 amino acids, such as from 12 to 25, 13 to 24, 14 to 22 or 15 to 20 amino acids in length. The contiguous amino acids from SEQ ID NO: 2 may be joined directly to each other or may comprise a linker between the stretches of contiguous amino acids. Preferably, a peptide linker (e.g. another amino acid sequence) is used to join the contiguous stretches of amino acids.

The vaccine may comprise a polypeptide comprising, consisting of, or consisting essentially of the amino acid sequence of SEQ ID NO: 3 (MVINDDAQRLLSQR) and/or any one or more of the peptides or polypeptides as described below alone or in combination. Specifically the vaccine may comprise a polypeptide comprising, consisting of or consisting essentially of at least one of the following amino acid sequences:

```
                                           (SEQ ID NO: 3)
          MVINDDAQRLLSQR, (SEQ ID NO: 4)
          MVINDDAQRLLSQRVANDEAALLELI, (SEQ ID NO: 5)
          MVINDDAQRLL[pS]QR, (SEQ ID NO: 7)
          VTTLADGGEVTWAID, (SEQ ID NO: 8)
          VTTLADGGEVTWAIDLNA, (SEQ ID NO: 9)
          EVVVAQPVWAGVDAGKADHY, (SEQ ID NO: 10)
          MTVTEVVVAQPVWAGVDAGKADHY
          and (SEQ ID NO: 50)
          VDAGKADHY.
```

Where two or more of these amino acid sequences are present in the polypeptide, they may be joined directly to one another, or the polypeptide may comprise one or more additional linking amino acids, such as from 1 to 20, 2 to 15, 3 to 10 or 4 to 8 amino acids. For example, A or AA may be used to join the amino terminus of

```
                                           (SEQ ID NO: 7)
          VTTLADGGEVTWAID, (SEQ ID NO: 8)
          VTTLADGGEVTWAIDLNA
``` to another amino acid sequence. The amino acids may be joined in any order. In some embodiments they are joined in the order that they occur in P900.

In some embodiments, the polypeptide in the vaccine, or encoded by the vaccine, comprises the amino acid sequence of any two or all of SEQ ID NO: 10, SEQ ID NO: 4 and SEQ ID NO: 7 in any order. These sequences may be immediately adjacent to one another, or may include one or more additional amino acids joining them. In some embodiments SEQ ID NO: 10, SEQ ID NO: 4 and SEQ ID NO: 7 may be joined in this order. In these cases the polypeptide may comprise the amino acid sequence of the whole of the normal extra-mycobacterial region:

```
                                           (SEQ ID NO: 51)
     MTVTEVVVAQPVWAGVDAGKADHYCMVINDDAQRLLSQRVANDEAALLEL

IAAVTTLADGGEVTWAID.
```

In some embodiments, the polypeptide in the vaccine, or encoded by the vaccine, comprises the amino acid sequence of SEQ ID NO: 3, SEQ ID NO:50 and SEQ ID NO: 7 in any order. For example, SEQ ID NO: 3, SEQ ID NO:50 and SEQ ID NO: 7 may be joined in this order. These sequences may be immediately adjacent to one another, or may include one or more additional amino acids joining them. For example, the polypeptide may comprise the amino acid sequence:

(SEQ ID NO: 52)
MVINDDAQRLLSQRVDAGKADHYAVTTLADGGEVTWAID.

In some embodiments, the vaccine may additionally comprise an amino acid sequence that forms all or part of a transmembrane stretch of P900. For example, the vaccine may comprise a polypeptide comprising the amino acid sequence LNAGGAALLIALLIAAGQRLLY (SEQ ID NO: 53) in addition to one or more of the amino acid sequences mentioned above. The polypeptide may further comprise one or more amino acids that are adjacent to the transmembrane stretch on the cytoplasmic side of the membrane. For example, the vaccine may comprise the amino acid sequence IPGRTVHHAAGSYRGE (SEQ ID NO: 54), the variant thereof, IPGATVHHAAGSYRGE (SEQ ID NO: 55), or any N-terminal fragment of either thereof. In the polypeptide, the amino acid sequence SEQ ID NO: 54 or SEQ ID NO: 55, or the N-terminal fragment thereof, is preferably adjacent to the C-terminal end of the amino acid sequence of SEQ ID NO: 53. For example, the polypeptide may comprise the amino acid sequence (SEQ ID NO: 56)
LNAGGAALLIALLIAAGQRLLYIPGRTVHHAAGSYRGE (SEQ ID NO: 57)
LNAGGAALLIALLIAAGQRLLYIPGATVHHAAGSYRGE.

The N-terminal fragment of SEQ ID NO: 54 or SEQ ID NO: 55, may be from 1 to 15 amino acids in length, such as from 2 to 14, 3 to 10, 4 to 9, 5 to 8, 6 or 7 amino acids in length.

The vaccine may, for example, include or encode a polypeptide comprising the amino acid sequence:

(SEQ ID NO: 58)
MTVTEVVVAQPVWAGVDAGKADHYCMVINDDAQRLLSQRVANDEAALLEL

IAAVTTLADGGEVTWAIDLNAGGAALLIALLIAAGQRLLYIPGRTVHHAA

GSYRGE;

(SEQ ID NO: 59)
MTVTEVVVAQPVWAGVDAGKADHYCMVINDDAQRLLSQRVANDEAALLEL

IAAVTTLADGGEVTWAIDLNAGGAALLIALLIAAGQRLLYIPGATVHHAA

GSYRGE (SEQ ID NO: 60)
MVINDDAQRLLSQRVDAGKADHYAVTTLADGGEVTWAIDLNAGGAALLIA

LLIAAGQRLLYIPGRTVHHAAGSYRGE;
or (SEQ ID NO: 61)
MVINDDAQRLLSQRVDAGKADHYAVTTLADGGEVTWAIDLNAGGAALLIA

LLIAAGQRLLYIPGATVHHAAGSYRGE.

SEQ ID NO: 58 and SEQ ID NO: 59 represent the normal extra-mycobacterial region, the transmembrane region (SEQ ID NO: 53) and the first intra-mycobacterial portion of the P900 sequence (SEQ ID NO: 54 or SEQ ID NO: 55) stopping short of the active site mechanism of the putative transposase. It has no known toxicity and is abundantly expressed in vivo during MAP infection. SEQ ID NO: 60 and SEQ ID NO: 61 disrupt the normal sequence of P900, place emphasis on the N-terminal epitope (SEQ ID NO: 3) and expose a further epitope (SEQ ID NO: 7/SEQ ID NO: 8) just before it dips into the transmembrane sequence (SEQ ID NO: 53). The present inventor has shown for the first time that the extracellular amino terminal end of P900 comprises at least three immunogenic regions. These immunogenic regions are SEQ ID NOs: 3 and 4 (referred to herein as A0X), which can be phosphorylated to form SEQ ID NOs: 5 and 6 (herein referred to as A0XP); the SEQ ID NOs: 7 and 8 (herein referred to as A1); and SEQ ID NOs: 9 and 10 (referred to herein as AN).

In a preferred embodiment, the vaccine comprises the A0X peptide, or the A0X peptide is coded in the vaccine sequence and expressed in the native amino acid form. After vaccination and expression the serine may be phosphorylated as shown. Both phosphorylated and non-phosphorylated forms of the peptide can be present within the same MAP infected cells and on the same cell surfaces. Similarly, vaccinated subjects may present both the phosphorylated and un-phosphorylated form to the immune system. Staining of such cells with fluorescent monoclonal antibodies specific for either the native peptide or its phosphorylated derivative shows that the antibodies are mutually exclusive and reveal separate labelled peptide clusters packing the cytoplasm and surface of MAP-infected cells. Despite being widely exposed to antibody and cell mediated immunity these mycobacterial peptides are not recognised by the unvaccinated MAP infected host. Vaccination releases the block on immune recognition of the amino terminal peptides as it does after vaccination at the carboxyterminal portion of P900.

There are important species differences in A0X serine phosphorylation. Monoclonal antibodies to A0XP were made by immunising mice to synthetic MVINDDAQRLLp-SQR and clonal selection. These antibodies demonstrated that phosphorylated A0XP could not be seen in sections of normal or inflamed human intestinal tissue except faintly in immune cells within intestinal blood vessels. A0XP is however, strongly positive against circulating human WBCs. On the other hand in cattle, sheep, goats and deer A0XP was strongly positive in intestinal cells as well in circulating WBCs. These new observations may be taken into account when considering the use of additional immunisation against MAP infection in animals using synthetic polymers of A0XP and appropriate adjuvants.

In a preferred embodiment, the vaccine comprises the A0X peptide, or the A0X peptide is coded in the vaccine sequence and expressed in the native amino acid form and the A0X peptide is not adjacent to a cysteine residue at its N-terminal end. For example, the A0X peptide is at the N-terminus of the peptide or polypeptide in the vaccine. The cysteine residue present next to the A0X peptide amino acid sequence in P900 is thought to tether P900 to the membrane. Expressing the A0X peptide without this N-terminal cysteine residue improves the visibility of the peptide to the immune system.

The vaccine may comprise A1 peptide, optionally in addition to the A0X peptide. The A1 peptide is closely attached to the external surface of MAP and its carboxy terminus dives into the outer layer of its first transmembrane portion (highlighted above). It is a robust antigen and a useful marker for MAP and closely related *M. avium*. For greatest immunogenicity, the two alanine residues present in the P900 amino acid sequence adjacent to the amino terminus of A1 are not included in A1 such that the peptide immunogen begins with VTT. However, the A1 peptide may additionally include two N-terminal alanine residues. The present inventor discovered that A1 is an immunogen in mice and rabbits immunised with truncated recombinant P900 followed by screening against a cascade of synthetic 15mer peptide antigens.

The vaccine may comprise the AN peptide, optionally in addition to the A0X and/or A1 peptide. Unlike the other amino terminal peptides of P900 spontaneous antibody recognition of the AN peptide sequence although low is generally seen in MAP infected hosts. If using the synthetic AN peptide as a vaccine immunogen omit the initial MTVT to improve immunogenicity. If using the peptide as an immunogen the c-terminal Cys can be removed to prevent cross linking or used with a maleimido linkage to a carrier molecule such as Keyhole Limpet Haemocyanin (KLH) or bovine serum albumin.

Particular examples of polypeptides that may be used include polypeptides comprising one of the following amino acid sequences:

(i)
(SEQ ID NO: 11)
MVINDDAQRLLSQRX$_2$VTTLADGGEVTWAID;

(ii)
(SEQ ID NO: 12)
MVINDDAQRLLSQRX$_2$VTTLADGGEVTWAIDLNA;

(iii)
(SEQ ID NO: 13)
MVINDDAQRLLSQRVANDEAALLELIX$_2$VTTLADGGEVTWAID;

(iv)
(SEQ ID NO: 14)
MVINDDAQRLLSQRVANDEAALLELIX$_2$VTTLADGGEVTWAIDLNA;

(v)
(SEQ ID NO: 15)
EVVVAQPVWAGVDAGKADHYX$_1$MVINTDDAQRLLSQR;

(vi)
(SEQ ID NO: 16)
EVVVAQPVWAGVDAGKADHYX$_1$MVINTDDAQRLLSQRVANDEAALLELI;

(vii)
(SEQ ID NO: 17)
MTVTEVVVAQPVWAGVDAGKADHYX$_1$MVINDDAQRLLSQR;
or (viii)
(SEQ ID NO: 18)
MTVTEVVVAQPVWAGVDAGKADHYX$_1$MVINDDAQRLLSQRVANDEAALLELI, (ix)
(SEQ ID NO: 19)
EVVVAQPVWAGVDAGKADHYX$_1$MVINDDAQRLLSQRVANDEAALLELIX$_2$VTTLADGGEVTWAIDLNA;
and (x)
(SEQ ID NO: 20)
MTVTEVVVAQPVWAGVDAGKADHYX$_1$MVINDDAQRLLSQRVANDEAALLELIX$_2$VTTLADGGEVTWAIDLNA.

wherein $X_1$ is a peptide linker or C and $X_2$ is a peptide linker, A or AA. The peptide linker may be any of the peptide linkers as described below.

The polypeptide may be a variant of SEQ ID NO: 2 that comprises one or more of SEQ ID NOs: 3 to 10 and has at least one amino acid substitution, deletion or addition in SEQ ID NO: 2 outside the region of the amino acid sequence of SEQ ID NOs: 3, 4, 5, 6, 7, 8, 9 or 10.

The polypeptide in the vaccine may further comprise the amino acid sequence of at least one additional MAP polypeptide, or a fragment thereof. The vaccine may further comprise the amino acid sequence of at least one additional MAP polypeptide, or a fragment thereof or at least one further polynucleotide encoding an additional MAP polypeptide, or a fragment thereof.

The polypeptide described above, may, in one embodiment, be joined to the additional polypeptide by a "self-cleaving" peptide. A "self-cleaving" peptide is a peptide that mediates cleavage of the polypeptide it is contained in during translation. One example of a self cleaving peptide is a 2A polypeptide. 2A peptides are 18-22 amino acid-long viral peptides that mediate cleavage of polypeptides during translation in eukaryotic cells (Liu et al. 2017 Scientific Reports 7:2193). The 2A peptide may be derived from any virus that includes a 2A peptide in its viral genome. The 2A peptide typically comprises the conserved sequence GDVEXNPGP (SEQ ID NO: 70). One example of a 2A peptide has the sequence APVKQTLNFDLLKLAGDVESNPGP (SEQ ID NO: 71).

The least one additional polypeptide may be, for example, an ahpC polypeptide, a gsd polypeptide, a p12 polypeptide and/or a mpa polypeptide. In particular, expression of a nucleic acid sequence encoding the extracellular amino terminal P900 peptides of P900 will facilitate the disabling of the P900 system when used in combination with a p12 polypeptide, for example when introduced into the HAV vaccine described in WO2007/017635, which is incorporated herein by reference in its entirety.

ahpC is a secreted component shared by many pathogenic mycobacteria. It is involved in the ability of MAP to survive within macrophages and is upregulated on entry into a state of microbial dormancy. The nucleic acid and amino acid sequences of the MAP ahpC gene and protein are given in SEQ ID NOs: 21 and 22 respectively. For use in the present invention, this sequence, or a variant thereof as discussed below may be used. For example, the MAP ahpC gene sequence may be codon optimised as discussed further below to make it more suitable for mammalian, in particular human, use. A suitable modified ahpC sequence and encoded protein are given in SEQ ID NOs: 31 and 32 respectively.

gsd is a glycosyl transferase encoded by the GS pathogenicity element with a predicted signal sequence and lipid acylation site. Microarray analysis shows that it is up-regulated in the intracellular environment. It is expressed on the microbial cell surface and is predicted to transfer GDP-fucose to sub-terminal rhamnose to cap surface glycopeptidolipid on MAP with derivatised fucose giving the pathogen in its ZN-negative state an inert, hydrophobic, and highly resistant cell surface. The nucleic acid and amino acid sequences of the MAP gsd gene and protein are given in SEQ ID NOs: 23 and 24 respectively. For use in the present invention, this sequence, or a variant thereof as discussed below, may be used. For example, the MAP gsd gene sequence may be codon optimised as discussed further below to make it more suitable for mammalian, in particular human, use. Other modifications may be made, for example potential acylation sites may be removed. One suitable modified gsd sequence and encoded protein are given in SEQ ID NOs: 33 and 34 respectively.

p12 is the carboxyterminal 17 kDa fragment of p43 encoded by IS900 which is also up-regulated intracellularly. It is strongly predicted on the cell surface and both in MAP and in p43.rec.E. coli it is the substrate for specific proteolytic cleavage and exodomain release. The nucleic acid and amino acid sequences of the MAP p12 gene and protein are given in SEQ ID NOs: 25 and 26 respectively. For use in the present invention, this sequence, or a variant thereof as discussed below may be used. For example, the MAP p12 gene sequence may be codon optimised as discussed further below to make it more suitable for mammalian, in particular human, use. One suitable modified p12 sequence and encoded protein are given in SEQ ID NOs: 35 and 36 respectively.

mpa is also expressed on the surface of MAP and is believed to be unique to the pathogen. It is both an acetylase and a predicted pore molecule with 10 transmembrane regions and a large extracellular peptide loop. The nucleic acid and amino acid sequences of the MAP mpa gene and protein are given in SEQ ID NOs: 29 and 30 respectively. For use in the present invention, this sequence, or a variant thereof as discussed below may be used. For example, the MAP mpa gene sequence may be codon optimised as discussed further below to make it more suitable for mammalian, in particular human, use. Other modifications may be made, for example transmembrane regions may be removed to reduce the hydrophobicity of the protein. One suitable modified mpa sequence and encoded protein are given in SEQ ID NOs: 39 and 40 respectively.

A suitable ahpC polypeptide may have the amino acid sequence of SEQ ID NO: 22 or SEQ ID NO: 32. A suitable gsd polypeptide may have the amino acid sequence of SEQ ID NO: 24 or SEQ ID NO: 34. A suitable p12 polypeptide may have the amino acid sequence of SEQ ID NO: 26 or SEQ ID NO: 36. A suitable mpa polypeptide may have the amino acid sequence of SEQ ID NO: 30 or SEQ ID NO: 40. A suitable ahpC, gsd, p12 or mpa sequence may alternatively be a variant of one of these specific sequences. For example, a variant may be a substitution, deletion or addition variant of any of the above amino acid sequences, or may be a fragment of any thereof as described herein.

In particular embodiments, the ahpC polypeptide may comprise the sequence of SEQ ID NO: 22, a variant thereof having more than 70% amino acid sequence identity to SEQ ID NO: 22 across the full length of SEQ ID NO: 22, or a fragment of at least 8 amino acids of SEQ ID NO: 22 which comprises an epitope. Preferably the ahpC polypeptide has the amino acid sequence given in SEQ ID NO: 32. The gsd polypeptide may comprise the sequence of SEQ ID NO: 24, a variant thereof having more than 70% amino acid sequence identity to SEQ ID NO: 24 across the full length of SEQ ID NO: 24, or a fragment of at least 8 amino acids of SEQ ID NO: 24 which comprises an epitope. Preferably the gsd polypeptide has the amino acid sequence given in SEQ ID NO: 34. The p12 polypeptide may comprise the sequence of SEQ ID NO: 26, a variant thereof having more than 70% amino acid sequence identity to SEQ ID NO: 26 across the full length of SEQ ID NO: 26, or a fragment of at least 8 amino acids of SEQ ID NO: 26 which comprises an epitope. The fragment of SEQ ID NO: 10 preferably comprises SEQ ID NOs: 44, 45, 46 or 47 and/or SEQ ID NO: 48. Preferably the p12 polypeptide has the amino acid sequence given in SEQ ID NO: 36 or SEQ ID NO: 37 or SEQ ID NOs: 44, 45, 46 or 47 and/or SEQ ID NO: 48. The mpa polypeptide may comprise the sequence of SEQ ID NO: 30, a variant thereof having more than 70% amino acid sequence identity to SEQ ID NO: 30 across the full length of SEQ ID NO: 30, or a fragment of at least 8 amino acids of SEQ ID NO: 30 which comprises an epitope. Preferably the mpa polypeptide has the amino acid sequence given in SEQ ID NO: 40.

The introduction of an extracellular amino terminal peptides of the P900 protein into a MAP vaccine comprising a p12 polypeptide acts to complete the disabling of both ends of the P900 protein system. Therefore, in a preferred embodiment, the vaccine comprises a polypeptide comprising at least 9 contiguous amino acids of SEQ ID NO: 2 and a polypeptide comprising at least 9 contiguous amino acids of SEQ ID NO: 10, or a polypeptide comprising at least 9 contiguous amino acids of SEQ ID NO: 2 and at least 9 contiguous amino acids of SEQ ID NO: 10, or a polynucleotide, or polynucleotides, encoding said polypeptide(s). For example, the vaccine may comprise a polypeptide comprising, consisting of, or consisting essentially of any one of SEQ ID NOs: 3 to 10 and a polypeptide comprising, consisting of, or consisting essentially of any one of SEQ ID NOs: 44 to 48, or a polypeptide comprising at least one of SEQ ID NOs: 3 to 10 and at least one of SEQ ID NOs: 44 to 48, or a polynucleotide, or polynucleotides, encoding said polypeptide(s). In a preferred embodiment the vaccine comprises a polypeptide comprising, consisting of, or consisting essentially SEQ ID NO: 3 or 4 and a polypeptide comprising, consisting of, or consisting essentially of any one of SEQ ID NOs: 44 to 47, or a polypeptide comprising SEQ ID NO: 3 or 4 and one of SEQ ID NOs: 44 to 48, or a polynucleotide, or polynucleotides, encoding said polypeptide(s).

In particular embodiments, the vaccine may comprise a polypeptide comprising, consisting of or consisting essentially of the amino acid sequence:

(SEQ ID NO: 41)
MQIFVKLPLLTIGDQFPAYELTALIAGDLSKVDAKQPGDYFTTV

TSEDHAGKWRVVFFWPKDFTGPEIATFGKLNDEFEDRDAQVLGV

SIDSEFVHFNWRAQHEDLKNLPFPMLSDIKRELSLATGVLNADG

VADRATFIVDPNNEIQFVSVTAGSVGRNVEEVLRVLDALQSDEL

CACNWRKGDPTLNATELLKASALGSIVGQTYREVEVVLVDGGST

DRTLDIANSFRPELGSRLVVHSGPDDGPYDAMNRGVGVATGEWV

LFLGADDTLYEPTTLAQVAAFLGDHAASHLVYGDVVMRSTKSRH

AGPFDLDRLLFETNLCHQSIFYRRELFDGIGPYNLRYRVWADWD

FNIRCFSNPALITRYMDVVISEYNDMTGFSMRQGTDKEFRKRLP

MYFWVAGWETCRRMLAFLKDKENRRLALRTRLIRVKAVSKERSA

EPRIRRHRHAEIILSMPGFGVILGAEFLAATGGDMAAFASADRL

AGVAGLAPVPRDSGRISGNLKRPRRYDRRLLRACVSIRTDPSSR

TYYDRKRTEGKRHTQAVLALARRRLNVLWAMLRDHAVYHPATTT

AAARLKLRRGERPMSLGQVFDPRANALHSFPLTGRMPWAPFIVS

SWLRNPHPAQYFTARCLRILPGLWIGAQGGSAAKLLMSGAPIEY

VLKDSAVWMFKFDIGGTPRDIPVAGIWNGSLWTPAWGGIHAIAS

NAYQFRNVIPARWSVSSAVLPNYRLVAALPMAYHNQRMRFRTDL

SYGVYGFAEINPIALVEKPALSWKSRLRRKNSSIALANMEDGGS

VGRSNDIPGRRARFIGEKAEDPPAPSPRPALRIPNPLLGLD.

The vaccine may comprise a polypeptide comprising, consisting of or consisting essentially of the amino acid sequence shown above (SEQ ID NO: 41), wherein a peptide comprising an amino acid sequence of at least 9 contiguous amino acids from the region of MAP P900 shown in SEQ ID NO: 2, preferably a peptide comprising, consisting of or consisting essentially of the amino acid sequence MVINDDAQRLLSQR, is added at the N-terminus or inserted between: positions 7 and 8, positions 199 and 200, positions 442 and 443, positions 577 and 578, and/or positions 820 and 821; or (SEQ ID NO: 42)
MQIFVKLPLLTIGDQFPAYELTALIAGDLSKVDAKQPGDYFTTV
TSEDHAGKWRVVFFWPKDFTGPEIATFGKLNDEFEDRDAQVLGV
SIDSEFVHFNWRAQHEDLKNLPFPMLSDIKRELSLATGVLNADG
VADRATFIVDPNNEIQFVSVTAGSVGRNVEEVLRVLDALQSDEL
CACNWRKGDPTLNATELLKASALGSIVGQTYREVEVVLVDGGST
DRTLDIANSFRPELGSRLVVHSGPDDGPYDAMNRGVGVATGEWV
LFLGADDTLYEPTTLAQVAAFLGDHAASHLVYGDVVMRSTKSRH
AGPFDLDRLLFETNLCHQSIFYRRELFDGIGPYNLRYRVWADWD
FNIRCFSNPALITRYMDVVISEYNDMTGFSMRQGTDKEFRKRLP
MYFWVAGWETCRRMLAFLKDKENRRLALRTRLIRVKAVSKERSA
EPRIRRHRHAEIILSMPGFGVILGAEFLAATGGDMAAFASADRL
AGVAGLAPVPRDSGRISGNLKRPRRYDRRLLRACYLSALVSIRT
DPSSRTYYDRKRTEGKRHTQAVLALARRRLNVLWAMLRDHAVYH
PATTTAAARLKLRRGERPMSLGQVFDPRANALHSFPLTGRMPWA
PFIVSSWLRNPHPAQYFTARCLRILPGLWIGAQGGSAAKLLMSG
APIEYVLKDSAVWMFKFDIGGTPRDIPVAGIWNGSLWTPAWGGI
HAIASNAYQFRNVIPARWSVSSAVLPNYRLVAALPMAYHNQRMR
FRTDLSYGVYGFAEINPIALVEKPALSWKSRLRRKNSSIALANM
EDGGSVGRSNDIPGRRARFIGEKAEDPPAPSPR**PALRIPNPLLG
LD** wherein a peptide comprising an amino acid sequence of at least 9 contiguous amino acids from the region of MAP P900 shown in SEQ ID NO: 2, preferably a peptide comprising, consisting of or consisting essentially of amino acid sequence MVINDDAQRLLSQR, is added at the N-terminus or inserted between: positions 7 and 8, positions 199 and 200, positions 442 and 443, positions 582 and 583, and/or positions 825 and 826.

In particular embodiments, the vaccine may comprise a polypeptide comprising, consisting of or consisting essentially of the amino acid sequence:

(SEQ ID NO: 62)
MTVTEVVVAQPVWAGVDAGKADHYCMVINDDAQRLLSQRVANDEAALL
ELIAAVTTLADGGEVTWAIDLNAGGAALLIALLIAAGQRLLYIPGATV
HHAAGSYRGEAPVKQTLNFDLLKLAGDVESNPGPMQIFVKLPLLTIGD
QFPAYELTALIAGDLSKVDAKQPGDYFTTVTSEDHAGKWRVVFFWPKD
FTGPEIATFGKLNDEFEDRDAQVLGVSIDSEFVHFNWRAQHEDLKNLP
FPMLSDIKRELSLATGVLNADGVADRATFIVDPNNEIQFVSVTAGSVG
RNVEEVLRVLDALQSDELCACNWRKGDPTLNATELLKASALGSIVGQT
YREVEVVLVDGGSTDRTLDIANSFRPELGSRLVVHSGPDDGPYDAMNR
GVGVATGEWVLFLGADDTLYEPTTLAQVAAFLGDHAASHLVYGDVVMR
STKSRHAGPFDLDRLLFETNLCHQSIFYRRELFDGIGPYNLRYRVWAD
WDFNIRCFSNPALITRYMDVVISEYNDMTGFSMRQGTDKEFRKRLPMY
FWVAGWETCRRMLAFLKDKENRRLALRTRLIRVKAVSKERSAEPRIRR
HRHAEIILSMPGFGVILGAEFLAATGGDMAAFASADRLAGVAGLAPVP
RDSGRISGNLKRPRRYDRRLLRACYLSALVSIRTDPSSRTYYDRKRTE
GKRHTQAVLALARRRLNVLWAMLRDHAVYHPATTTAAARLKLRRGERP
MSLGQVFDPRANALHSFPLTGRMPWAPFIVSSWLRNPHPAQYFTARCL
RILPGLWIGAQGGSAAKLLMSGAPIEYVLKDSAVWMFKFDIGGTPRDI
PVAGIWNGSLWTPAWGGIHAIASNAYQFRNVIPARWSVSSAVLPNYRL
VAALPMAYHNQRMRFRTDLSYGVYGFAEINPIALVEKPALSWKSRLRR
KNSSIALANMEDGGSVGRSNDIPGRRARFIGEKAEDPPAPSPR**PALRI
PNPLLGLD**;

(SEQ ID NO: 63)
MTVTEVVVAQPVWAGVDAGKADHYCMVINDDAQRLLSQRVANDEAALL
ELIAAVTTLADGGEVTWAI<u>DLNAGGAALLIALLIAAGQRLLY</u>IPGATV
HHAAGSYRGEAPVKQTLNFDLLKLAGDVESNPGPMQIFVKLPLLTIGD
QFPAYELTALIAGDLSKVDAKQPGDYFTTVTSEDHAGKWRVVFFWPKD
FTGPEIATFGKLNDEFEDRDAQVLGVSIDSEFVHFNWRAQHEDLKNLP
FPMLSDIKRELSLATGVLNADGVADRATFIVDPNNEIQFVSVTAGSVG
RNVEEVLRVLDALQSDELCACNWRKGDPTLNATELLKASALGSIVGQT
YREVEVVLVDGGSTDRTLDIANSFRPELGSRLVVHSGPDDGPYDAMNR
GVGVATGEWVLFLGADDTLYEPTTLAQVAAFLGDHAASHLVYGDVVMR
STKSRHAGPFDLDRLLFETNLCHQSIFYRRELFDGIGPYNLRYRVWAD
WDFNIRCFSNPALITRYMDVVISEYNDMTGFSMRQGTDKEFRKRLPMY
FWVAGWETCRRMLAFLKDKENRRLALRTRLIRVKAVSKERSAEPRIRR
HRHAEIILSMPGFGVILGAEFLAATGGDMAAFASADRLAGVAGLAPVP
RDSGRISGNLKRPRRYDRRLLRACVSIRTDPSSRTYYDRKRTEGKRHT
QAVLALARRRLNVLWAMLRDHAVYHPATTTAAARLKLRRGERPMSLGQ
VFDPRANALHSFPLTGRMPWAPFIVSSWLRNPHPAQYFTARCLRILPG
LWIGAQGGSAAKLLMSGAPIEYVLKDSAVWMFKFDIGGTPRDIPVAGI
WNGSLWTPAWGGIHAIASNAYQFRNVIPARWSVSSAVLPNYRLVAALP
MAYHNQRMRFRTDLSYGVYGFAEINPIALVEKPALSWKSRLRRKNSSI
ALANMEDGGSVGRSNDIPGRRARFIGEKAEDPPAPSPR**PALRIPNPLL
GLD**;

(SEQ ID NO: 64)
MTVTEVVVAQPVWAGVDAGKADHYCMVINDDAQRLLSQRVANDEAALL
ELIAAVTTLADGGEVTWAI<u>DLNAGGAALLIALLIAAGQRLLY</u>IPGRTV
HHAAGSYRGEAPVKQTLNFDLLKLAGDVESNPGPMQIFVKLPLLTIGD
QFPAYELTALIAGDLSKVDAKQPGDYFTTVTSEDHAGKWRVVFFWPKD
FTGPEIATFGKLNDEFEDRDAQVLGVSIDSEFVHFNWRAQHEDLKNLP
FPMLSDIKRELSLATGVLNADGVADRATFIVDPNNEIQFVSVTAGSVG
RNVEEVLRVLDALQSDELCACNWRKGDPTLNATELLKASALGSIVGQT
YREVEVVLVDGGSTDRTLDIANSFRPELGSRLVVHSGPDDGPYDAMNR
GVGVATGEWVLFLGADDTLYEPTTLAQVAAFLGDHAASHLVYGDVVMR

-continued

STKSRHAGPFDLDRLLFETNLCHQSIFYRRELFDGIGPYNLRYRVWAD
WDFNIRCFSNPALITRYMDVVISEYNDMTGFSMRQGTDKEFRKRLPMY
FWVAGWETCRRMLAFLKDKENRRLALRTRLIRVKAVSKERSAEPRIRR
HRHAEIILSMPGFGVILGAEFLAATGGDMAAFASADRLAGVAGLAPVP
RDSGRISGNLKRPRRYDRRLLRACYLSALVSIRTDPSSRTYYDRKRTE
GKRHTQAVLALARRRLNVLWAMLRDHAVYHPATTTAAARLKLRRGERP
MSLGQVFDPRANALHSFPLTGRMPWAPFIVSSWLRNPHPAQYFTARCL
RILPGLWIGAQGGSAAKLLMSGAPIEYVLKDSAVWMFKFDIGGTPRDI
PVAGIWNGSLWTPAWGGIHAIASNAYQFRNVIPARWSVSSAVLPNYRL
VAALPMAYHNQRMRFRTDLSYGVYGFAEINPIALVEKPALSWKSRLRR
KNSSIALANMEDGGSVGRSNDIPGRRARFIGEKAEDPPAPSPR**PALRI
PNPLLGLD**;

(SEQ ID NO: 65)
MTVTEVVVAQPVWAGVDAGKADHYCMVINDDAQRLLSQRVANDEAALL
ELIAAVTTLADGGEVTWAID<u>LNAGGAALLIALLIAAGQRLLYI</u>PGRTV
HHAAGSYRGEAPVKQTLNFDLLKLAGDVESNPGPMQIFVKLPLLTIGD
QFPAYELTALIAGDLSKVDAKQPGDYFTTVTSEDHAGKWRVVFFWPKD
FTGPEIATFGKLNDEFEDRDAQVLGVSIDSEFVHFNWRAQHEDLKNLP
FPMLSDIKRELSLATGVLNADGVADRATFIVDPNNEIQFVSVTAGSVG
RNVEEVLRVLDALQSDELCACNWRKGDPTLNATELLKASALGSIVGQT
YREVEVVLVDGGSTDRTLDIANSFRPELGSRLVVHSGPDDGPYDAMNR
GVGVATGEWVLFLGADDTLYEPTTLAQVAAFLGDHAASHLVYGDVVMR
STKSRHAGPFDLDRLLFETNLCHQSIFYRRELFDGIGPYNLRYRVWAD
WDFNIRCFSNPALITRYMDVVISEYNDMTGFSMRQGTDKEFRKRLPMY
FWVAGWETCRRMLAFLKDKENRRLALRTRLIRVKAVSKERSAEPRIRR
HRHAEIILSMPGFGVILGAEFLAATGGDMAAFASADRLAGVAGLAPVP
RDSGRISGNLKRPRRYDRRLLRACVSIRTDPSSRTYYDRKRTEGKRHT
QAVLALARRRLNVLWAMLRDHAVYHPATTTAAARLKLRRGERPMSLGQ
VFDPRANALHSFPLTGRMPWAPFIVSSWLRNPHPAQYFTARCLRILPG
LWIGAQGGSAAKLLMSGAPIEYVLKDSAVWMFKFDIGGTPRDIPVAGI
WNGSLWTPAWGGIHAIASNAYQFRNVIPARWSVSSAVLPNYRLVAALP
MAYHNQRMRFRTDLSYGVYGFAEINPIALVEKPALSWKSRLRRKNSSI
ALANMEDGGSVGRSNDIPGRRARFIGEKAEDPPAPSPR**PALRIPNPLL
GLD**;

(SEQ ID NO: 66)
MVINDDAQRLLSQRVDAGKADHYAVTTLADGGEVTWAID<u>LNAGGAALL
IALLIAAGQRLLYI</u>PGATVHHAAGSYRGEAPVKQTLNFDLLKLAGDVE
SNPGPMQIFVKLPLLTIGDQFPAYELTALIAGDLSKVDAKQPGDYFTT
VTSEDHAGKWRVVFFWPKDFTGPEIATFGKLNDEFEDRDAQVLGVSID
SEFVHFNWRAQHEDLKNLPFPMLSDIKRELSLATGVLNADGVADRATF
IVDPNNEIQFVSVTAGSVGRNVEEVLRVLDALQSDELCACNWRKGDPT
LNATELLKASALGSIVGQTYREVEVVLVDGGSTDRTLDIANSFRPELG
SRLVVHSGPDDGPYDAMNRGVGVATGEWVLFLGADDTLYEPTTLAQVA
AFLGDHAASHLVYGDVVMRSTKSRHAGPFDLDRLLFETNLCHQSIFYR
RELFDGIGPYNLRYRVWADWDFNIRCFSNPALITRYMDVVISEYNDMT
GFSMRQGTDKEFRKRLPMYFWVAGWETCRRMLAFLKDKENRRLALRTR
LIRVKAVSKERSAEPRIRRHRHAEIILSMPGFGVILGAEFLAATGGDM
AAFASADRLAGVAGLAPVPRDSGRISGNLKRPRRYDRRLLRACYLSAL
VSIRTDPSSRTYYDRKRTEGKRHTQAVLALARRRLNVLWAMLRDHAVY
HPATTTAAARLKLRRGERPMSLGQVFDPRANALHSFPLTGRMPWAPFI
VSSWLRNPHPAQYFTARCLRILPGLWIGAQGGSAAKLLMSGAPIEYVL
KDSAVWMFKFDIGGTPRDIPVAGIWNGSLWTPAWGGIHAIASNAYQFR
NVIPARWSVSSAVLPNYRLVAALPMAYHNQRMRFRTDLSYGVYGFAEI
NPIALVEKPALSWKSRLRRKNSSIALANMEDGGSVGRSNDIPGRRARF
IGEKAEDPPAPSPRPALRIPNPLLGLD;
or (SEQ ID NO: 67)
MVINDDAQRLLSQRVDAGKADHYAVTTLADGGEVTWAID<u>LNAGGAALL
IALLIAAGQRLLYI</u>PGATVHHAAGSYRGEAPVKQTLNFDLLKLAGDVE
SNPGPMQIFVKLPLLTIGDQFPAYELTALIAGDLSKVDAKQPGDYFTT
VTSEDHAGKWRVVFFWPKDFTGPEIATFGKLNDEFEDRDAQVLGVSID
SEFVHFNWRAQHEDLKNLPFPMLSDIKRELSLATGVLNADGVADRATF
IVDPNNEIQFVSVTAGSVGRNVEEVLRVLDALQSDELCACNWRKGDPT
LNATELLKASALGSIVGQTYREVEVVLVDGGSTDRTLDIANSFRPELG
SRLVVHSGPDDGPYDAMNRGVGVATGEWVLFLGADDTLYEPTTLAQVA
AFLGDHAASHLVYGDVVMRSTKSRHAGPFDLDRLLFETNLCHQSIFYR
RELFDGIGPYNLRYRVWADWDFNIRCFSNPALITRYMDVVISEYNDMT
GFSMRQGTDKEFRKRLPMYFWVAGWETCRRMLAFLKDKENRRLALRTR
LIRVKAVSKERSAEPRIRRHRHAEIILSMPGFGVILGAEFLAATGGDM
AAFASADRLAGVAGLAPVPRDSGRISGNLKRPRRYDRRLLRACVSIRT
DPSSRTYYDRKRTEGKRHTQAVLALARRRLNVLWAMLRDHAVYHPATT
TAAARLKLRRGERPMSLGQVFDPRANALHSFPLTGRMPWAPFIVSSWL
RNPHPAQYFTARCLRILPGLWIGAQGGSAAKLLMSGAPIEYVLKDSAV
WMFKFDIGGTPRDIPVAGIWNGSLWTPAWGGIHAIASNAYQFRNVIPA
RWSVSSAVLPNYRLVAALPMAYHNQRMRFRTDLSYGVYGFAEINPIAL
VEKPALSWKSRLRRKNSSIALANMEDGGSVGRSNDIPGRRARFIGEKA
EDPPAPSPRPALRIPNPLLGLD

(SEQ ID NO: 68)
MVINDDAQRLLSQRVDAGKADHYAVTTLADGGEVTWAID<u>LNAGGAALL
IALLIAAGQRLLYI</u>PGRTVHHAAGSYRGEAPVKQTLNFDLLKLAGDVE
SNPGPMQIFVKLPLLTIGDQFPAYELTALIAGDLSKVDAKQPGDYFTT
VTSEDHAGKWRVVFFWPKDFTGPEIATFGKLNDEFEDRDAQVLGVSID
SEFVHFNWRAQHEDLKNLPFPMLSDIKRELSLATGVLNADGVADRATF
IVDPNNEIQFVSVTAGSVGRNVEEVLRVLDALQSDELCACNWRKGDPT

-continued

LNATELLKASALGSIVGQTYREVEVVLVDGGSTDRTLDIANSFRPELG

SRLVVHSGPDDGPYDAMNRGVGVATGEWVLFLGADDTLYEPTTLAQVA

AFLGDHAASHLVYGDVVMRSTKSRHAGPFDLDRLLFETNLCHQSIFYR

RELFDGIGPYNLRYRVWADWDFNIRCFSNPALITRYMDVVISEYNDMT

GFSMRQGTDKEFRKRLPMYFWVAGWETCRRMLAFLKDKENRRLALRTR

LIRVKAVSKERSAEPRIRRHRHAEIILSMPGFGVILGAEFLAATGGDM

AAFASADRLAGVAGLAPVPRDSGRISGNLKRPRRYDRRLLRACYLSAL

VSIRTDPSSRTYYDRKRTEGKRHTQAVLALARRRLNVLWAMLRDHAVY

HPATTTAAARLKLRRGERPMSLGQVFDPRANALHSFPLTGRMPWAPFI

VSSWLRNPHPAQYFTARCLRILPGLWIGAQGGSAAKLLMSGAPIEYVL

KDSAVWMFKFDIGGTPRDIPVAGIWNGSLWTPAWGGIHAIASNAYQFR

NVIPARWSVSSAVLPNYRLVAALPMAYHNQRMRFRTDLSYGVYGFAEI

NPIALVEKPALSWKSRLRRKNSSIALANMEDGGSVGRSNDIPGRRARF

IGEKAEDPPAPSPRPALRIPNPLLGLD;

or (SEQ ID NO: 69)
MVINDDAQRLLSQRVDAGKADHYAVTTLADGGEVTWAID<u>LNAGGAALL</u>

<u>IALLIAAGQRLLYI</u>PGRTVHHAAGSYRGEAPVKQTLNFDLLKLAGDVE

SNPGPMQIFVKLPLLTIGDQFPAYELTALIAGDLSKVDAKQPGDYFTT

VTSEDHAGKWRVVFFWPKDFTGPEIATFGKLNDEFEDRDAQVLGVSID

SEFVHFNWRAQHEDLKNLPFPMLSDIKRELSLATGVLNADGVADRATF

IVDPNNEIQFVSVTAGSVGRNVEEVLRVLDALQSDELCACNWRKGDPT

LNATELLKASALGSIVGQTYREVEVVLVDGGSTDRTLDIANSFRPELG

SRLVVHSGPDDGPYDAMNRGVGVATGEWVLFLGADDTLYEPTTLAQVA

AFLGDHAASHLVYGDVVMRSTKSRHAGPFDLDRLLFETNLCHQSIFYR

RELFDGIGPYNLRYRVWADWDFNIRCFSNPALITRYMDVVISEYNDMT

GFSMRQGTDKEFRKRLPMYFWVAGWETCRRMLAFLKDKENRRLALRTR

LIRVKAVSKERSAEPRIRRHRHAEIILSMPGFGVILGAEFLAATGGDM

AAFASADRLAGVAGLAPVPRDSGRISGNLKRPRRYDRRLLRACVSIRT

DPSSRTYYDRKRTEGKRHTQAVLALARRRLNVLWAMLRDHAVYHPATT

TAAARLKLRRGERPMSLGQVFDPRANALHSFPLTGRMPWAPFIVSSWL

RNPHPAQYFTARCLRILPGLWIGAQGGSAAKLLMSGAPIEYVLKDSAV

WMFKFDIGGTPRDIPVAGIWNGSLWTPAWGGIHAIASNAYQFRNVIPA

RWSVSSAVLPNYRLVAALPMAYHNQRMRFRTDLSYGVYGFAEINPIAL

VEKPALSWKSRLRRKNSSIALANMEDGGSVGRSNDIPGRRARFIGEKA

EDPPAPSPRPALRIPNPLLGLD.

The vaccine may be a nucleic acid vaccine comprising a polynucleotide encoding any one or more of the polypeptides described herein. The vaccine may comprise a polynucleotide comprising two or more copies, such as 3, 4, 5 or more copies of a nucleotide sequence encoding any one or more of the peptides or polypeptides described herein.

Peptides

The invention provides immunogenic MAP peptides. The invention provides a peptide of up to 100 amino acids comprising the sequence (SEQ ID NO: 4) or (SEQ ID NO: 6)
MVINDDAQRLLSQRVANDEAALLELI.

The peptide of the invention may have a length of from 26 to 100, 30 to 95, 35 to 80, 40 to 75, 45 to 70, 50 to 65, 55 to 60 amino acids. The peptide may be a fragment of P900.

The peptide of the invention may further comprise the amino acid sequence: VTTLADGGEVTWAID or VTTLADGGEVTWAIDLNA; and/or VDAGKADHY, EVVVAQPVWAGVDAGKADHY or MTVTE-VVVAQPVWAGVDAGKADHY. The peptide of the invention may comprise the amino acid sequence of any one of SEQ ID NOs: 11 to 20. The peptide linker in any one of SEQ ID NOs: 1 to 20 may be any of the peptide linkers as described below.

The peptide may comprise, consist of or consist essentially of the amino acid sequence of SEQ ID NO: 4 or SEQ ID NO: 6.

Polypeptides

In one aspect, the invention provides a polypeptide that comprises an amino acid sequence of at least 9 contiguous amino acids from a region of MAP P900 fused to one or more additional MAP polypeptides, or a fragment thereof. The additional MAP polypeptide may, in one embodiment, be a fragment comprising the all or part of the C-terminal extracellular region of P900. Alternatively, or additionally, the at least one additional MAP polypeptide may be comprised of all or part of a different MAP protein.

The polypeptide comprising an amino acid sequence of at least 9 contiguous amino acids from the region of MAP P900 shown in SEQ ID NO: 2 may be any of the polypeptides described above. In preferred embodiments, this polypeptide comprises the amino acid sequence shown in SEQ ID NO: 3, the amino acid sequence shown in SEQ ID NO: 7 and/or the amino acid sequence shown in SEQ ID NO: 9. In a particularly preferred embodiment, this polypeptide comprises the amino acid sequence shown in SEQ ID NO: 3.

The p12 polypeptide disclosed herein comprises the C-terminal extracellular region of MAP P900. Therefore, in one embodiment, the additional MAP polypeptide is the p12 polypeptide or a fragment or variant thereof. Any one of the p12 polypeptides disclosed herein may be used. For example, the fragment of the p12 polypeptide may comprise, consist essentially of, or consist of the amino acid sequence shown in SEQ ID NO: 48 and/or or any one of SEQ ID NOs: 44 to 47.

The additional MAP polypeptide may be an ahpC polypeptide, a gsd polypeptide, a p12 polypeptide and/or a mpa polypeptide. In one embodiment, the polypeptide comprises the amino acid sequence MVINDDAQRLLSQR and any one of or any combination of an ahpC polypeptide, a gsd polypeptide, a p12 polypeptide and a mpa polypeptide. In some embodiments, the polypeptide may be phosphorylated at the serine residue in the MVINDDAQRLLSQR amino acid sequence.

The ahpC polypeptide can be any of the ahpC polypeptides described herein. The gsd polypeptide may be any of the gsd polypeptides described herein. The mpa polypeptide may be any of the MPA polypeptides described herein.

In a preferred embodiment, the N-terminal P900 polypeptide is provided with any one or more of the four polypeptides ahpC, gsd, p12 and mpa in a single fusion protein. The four polypeptide sequences in such a fusion protein may be any of the polypeptides or variants described herein. The four polypeptides may be provided in any order in the fusion protein. In one embodiment they are provided in the order N-terminal P900-ahpC-gsd-p12-mpa.

In one embodiment, the ahpC, gsd, p12 and mpa polypeptides present in a fusion protein are those given in SEQ ID NOs: 32, 34, 36 and 40.

In an alternative embodiment, the polypeptides may be present in two or more separate polypeptide molecules, which may or may not be linked by non-covalent linkages. For example, the polypeptides may be provided separately, or may be provided in two, three or more separate fusion protein polypeptide molecules. For example, the N-terminal P900 polypeptide may be provided as one molecule and the ahpC, gsd, p12 and mpa may be provided as a fusion protein.

In the fusion protein, linker sequences may separate the required polypeptide sequences and/or there may or may not be additional sequences present at the N terminal or C terminal of the peptide. Typically the fusion protein comprises 1, 2, 3, or more such linkers. The linkers are typically 1, 2, 3, 4 or more amino acids in length. Thus in the peptide 1, 2, 3 or all of the polypeptide sequences may be contiguous with each other or may be separated from each other, for example by such linkers.

The peptides and polypeptides may be used as induce immune responses against MAP in subjects.

In one embodiment the polypeptide comprises the amino acid sequence of SEQ ID NO: 41 wherein a peptide comprising an amino acid sequence of at least 9 contiguous amino acids from the region of MAP P900 shown in SEQ ID NO: 2, preferably the amino acid sequence MVINDDAQRLLSQR, is inserted between: positions 7 and 8, positions 199 and 200, positions 442 and 443, positions 577 and 578, and/or positions 820 and 821.

In another embodiment, the polypeptide comprises the amino acid sequence of SEQ ID NO: 42 wherein a peptide comprising an amino acid sequence of at least 9 contiguous amino acids from the region of MAP P900 shown in SEQ ID NO: 2, preferably the amino acid sequence MVINDDAQRLLSQR, is inserted between: positions 7 and 8, positions 199 and 200, positions 442 and 443, positions 582 and 583, and/or positions 825 and 826.

In either SEQ ID NO: 41 or 42, the MQIFVKL leader sequence may be replaced by any other suitable leader sequence. Similarly, the PALRIPNPLLGLD tag may be replaced by any other tag. The insertions of the at least 9 contiguous amino acids from SEQ ID NO: 2 may be made directly into the one or more of the indicated positions of SEQ ID NO: 41 or 42, or a peptide linker may be included at one or both ends of the inserted sequence.

Variants

A "polypeptide" is used herein in its broadest sense to refer to a compound of two or more subunit amino acids, amino acid analogs, or other peptidomimetics. The term "polypeptide" is used synonymously with the term "peptide". The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

A variant of a polypeptide may comprise 1, 2, 3, 4, 5, up to 10, up to 20, up to 30 or more amino acid substitutions and/or deletions from the sequences given in the sequence listing. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

Preferred "variants" include those in which instead of the naturally occurring amino acid the amino acid which appears in the sequence is a structural analog thereof. Amino acids used in the sequences may also be derivatized or modified, e.g. labelled, providing the function of the peptide is not significantly adversely affected.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Suitable variants may comprise sequences of naturally occurring polypeptides from mycobacteria other than MAP. For example, a variant ahpC polypeptide sequence may derive from a different mycobacterial strain to MAP. Such naturally occurring variants preferably maintain the ability to stimulate an immune response which is capable of acting against MAP. That is, the immune response to the variant polypeptide will react against MAP polypeptides as well as the variant polypeptide used.

Preferably variants according to the invention have an amino acid sequence which has more than 60%, or more than 70%, e.g. 75 or 80%, preferably more than 85%, e.g. more than 90 or 95% amino acid identity to, for example, SEQ ID NO: 2, 22, 32, 24, 34, 26, 36, 30 or 40, (according to the test described hereinafter). This level of amino acid identity may be seen across the full length of the sequence or over a part of the sequence, such as 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: G, P, S, N, D, Q, E, K, R. Sequence identity at a particular residue is intended to include identical residues which have simply been derivatized.

Particular modifications can be made to any of the wild type MAP proteins sequences given in SEQ ID Nos: 2, 22, 32, 24, 34, 26, 36, 30 or 40. For example, modification can be made to try to improve the overall properties of the variant protein as an immunogen.

In one embodiment, a wild-type protein may be modified by deletion or substitution to remove an acylation site. Such an acylation site might affect the overall conformation of the protein. By omitting acylation sites, for example by excluding or substituting a cysteine residue, the presentation of effective epitopes within the protein may be optimised. For example, the wild type MAP gsd sequence given in SEQ ID NO: 24 includes a cysteine residue at position 22. In the variant of SEQ ID NO: 34, the amino acid sequence has been modified by truncation at the N-terminal such that this cysteine residue is no longer present. Similarly, the N-terminal fragment of P900 shown in SEQ ID NO: 22 comprises a cysteine residue at position 25. This cysteine is preferably deleted, or substituted by one or more amino acid, such as by a peptide linker. Such a modification may be made to a wild type protein or to any of the variant or fragment sequences, such as the codon optimised sequences, described herein.

In another embodiment, a wild type MAP protein may be modified to disable or remove potential cross-reacting epitopes. For example, where a polypeptide of the invention is intended for use in a human, the polypeptide sequence may be modified to disable or remove potential cross-reacting human epitopes, such as sequences which generate antibodies in human patients which may cross-react with similar sequences in human proteins. Modifications may thus be made to the MAP sequences to avoid such cross-reactivity but to maintain the ability to generate an anti-MAP immune response.

For example within the wild type MAP gsd sequence the lysine residues at positions 239 and 241 (see SEQ ID NO: 24) may each be substituted with asparagine. An equivalent substitution may be made in any of the variant or fragment gsd sequences described herein. For example in the variant sequence of SEQ ID NO: 34, the lysine residues at positions 216 and 218 may be replaced with asparagines. This may be achieved by modifying the nucleic acid sequence which encodes the gsd polypeptide. For example, in the gsd polynucleotide sequence of SEQ ID NO: 33, the AAG codons at positions 646 to 648 and 651 to 654 may be replaced by AAT. This maintains the optimised human codon usage of SEQ ID NO: 33 and further removes potentially cross-reacting human epitopes.

Similarly, modifications mat be made to the MAP ahpC sequence. In the wild-type ahpC sequence of SEQ ID NO: 22, the lysine at position 29 may be replaced with threonine and the proline at position 31 may be replaced with leucine. An equivalent substitution may be made in any of the variant or fragment ahpC sequences described herein. For example, in the modified variant sequence of SEQ ID NO: 32, the same substitutions may be made at the position 28 lysine and the position 30 proline. This may be achieved by modifying the nucleic acid sequence which encodes the ahpC polypeptide. For example, in the ahpC polynucleotide sequence of SEQ ID NO: 31, the AAA codon at positions 82 to 84 may be replaced by ACA and the CCC codon at positions 88 to 90 may be replaced by CTC. This maintains the optimised human codon usage of SEQ ID NO: 31 and further removes potentially cross-reacting human epitopes.

Similarly, modifications may be made to reduce the hydrophobicity of the protein and thus to help optimise the surface presentation of epitopes. For example, the wild-type mpa sequence of SEQ ID NO: 30 includes ten transmembrane regions. In order to reduce the hydrophobicity of the protein, one or more of these regions, or parts of these regions, may be omitted or substituted. For example, one, more or all of the transmembrane regions may be deleted. Such regions may be deleted totally or partially, optionally leaving none, one, two or more amino acid residues from the ends of the transmembrane sequence in the protein. Thus one modification may be the deletion or substitution of one or more hydrophobic amino acids. An example of this is seen in SEQ ID NO: 40 which is a variant of MAP mpa in which most of the transmembrane sequences have been deleted, leaving only one or two amino acids from the transmembrane regions in the variant polypeptide. Another example is deletion of the four N-terminal amino acid residues, MTVT, of SEQ ID NO: 22.

Polypeptide "fragments" may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions. For example, a variant of the invention may consist of or comprise two or more epitope regions from a full length polypeptide of the region in the absence of non-epitope amino acids. Preferably a fragment of an N-terminal P900, ahpC, gsd, p12 or mpa polypeptide comprises at least one epitope capable of inducing an immune response against the unmodified MAP polypeptide. Such fragments may be derived from a sequence of SEQ ID NO: 2, 22, 32, 24, 34, 26, 36, 30 or 40, or may be derived from a variant peptide as described herein. Preferably such fragments are between 8 and 150 residues in length, e.g. 8 to 50 or 8 to 30 residues. Alternatively, fragments of the invention may be longer sequences, for example comprising at least 50%, at least 60%, at least 70%, at least 80% or at least 90% of the full length polypeptide.

Preferably, a variant is a functional variant thereof. In particular, a variant polypeptide should retain the ability to stimulate an immune response against the unmodified MAP polypeptide. In one embodiment, a functional variant polypeptide should be capable of acting as an antigen and should include at least one functional epitope from the original polypeptide.

An "antigen" refers to any agent, generally a macromolecule, which can elicit an immunological response in an individual. As used herein, "antigen" is generally used to refer to a polypeptide molecule or portion thereof which contains one or more epitopes. Furthermore, for the purposes of the present invention, an "antigen" includes a polypeptide having modifications, such as deletions, additions and substitutions (generally conservative in nature) to the native sequence, so long as the polypeptide maintains sufficient immunogenicity. These modifications may be deliberate, for example through site-directed mutagenesis, or may be accidental, such as through mutations of hosts which produce the antigens.

An "immune response" against an antigen of interest is the development in an individual of a humoral and/or a cellular immune response to that antigen. A "humoral immune response" refers to an immune response mediated by antibody molecules, while a "cellular immune response" is one mediated by T-lymphocytes and/or other white blood cells.

As used herein, the term "epitope" generally refers to the site on a target antigen which is recognised by an immune receptor such as a T-cell receptor and/or an antibody. Preferably it is a short peptide derived from or as part of a protein. However the term is also intended to include peptides with glycopeptides and carbohydrate epitopes. A single antigenic molecule may comprise several different epitopes. The term "epitope" also includes modified sequences of amino acids or carbohydrates which stimulate responses which recognise the whole organism.

It is advantageous if the selected epitope is specific to MAP, or involved in the pathogenicity of MAP. For example, it is advantageous if the immune receptor and/or antibody which recognises the epitope will only recognise this epitope from MAP, and not epitopes in other unrelated proteins, in particular proteins from unrelated organisms or host proteins. If the epitope is involved in pathogenicity of MAP, then an immune response against such an epitope may be used to target pathogenic MAP infections.

An epitope may also be related to equivalent epitopes on other mycobacteria. For example, many individuals suffering from MAP infection are also infected by *M. avium* as a secondary co-pathogen. Other *M. avium* complexes may be present or involved in Crohn's disease, Johne's disease, Ulcerative Colitis, Psoriasis, Thyroiditis, Sarcoidosis, Parkinson's disease, Multiple Sclerosis, Type 1 Diabetes, arthritis, ankylosing spondylitis, rheumatoid arthritis, irritable bowel syndrome, inflammatory bowel disease, chronic enteritis, Alzheimer's disease, multiple sclerosis, idiopathic pulmonary fibrosis, leprosy and/or chronic fatigue syndrome. Many of the proteins expressed in MAP such as AhpC are very similar to those expressed in *M. avium*. If the polypeptide of the invention includes one or more epitopes which are capable of stimulating an immune response which acts against *M. avium* in addition to MAP, a further, secondary, therapeutic effect may be achieved.

Epitopes can be identified from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81. Some guidelines in determining whether a protein or an epitope of interest will stimulate a response, include: peptide length—the peptide should be at least 8 or 9 amino acids long to fit into the MHC class I complex and at least 8-25, such at least as 13-25 amino acids long to fit into a class II MHC complex. These lengths are the minimum for the peptide to bind to the respective MHC complex. It is preferred for the peptides to be longer than these lengths because cells may cut peptides. The peptide should contain an appropriate anchor motif which will enable it to bind to the various class I or class II molecules with high enough specificity to generate an immune response. This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein database.

Figure 3:
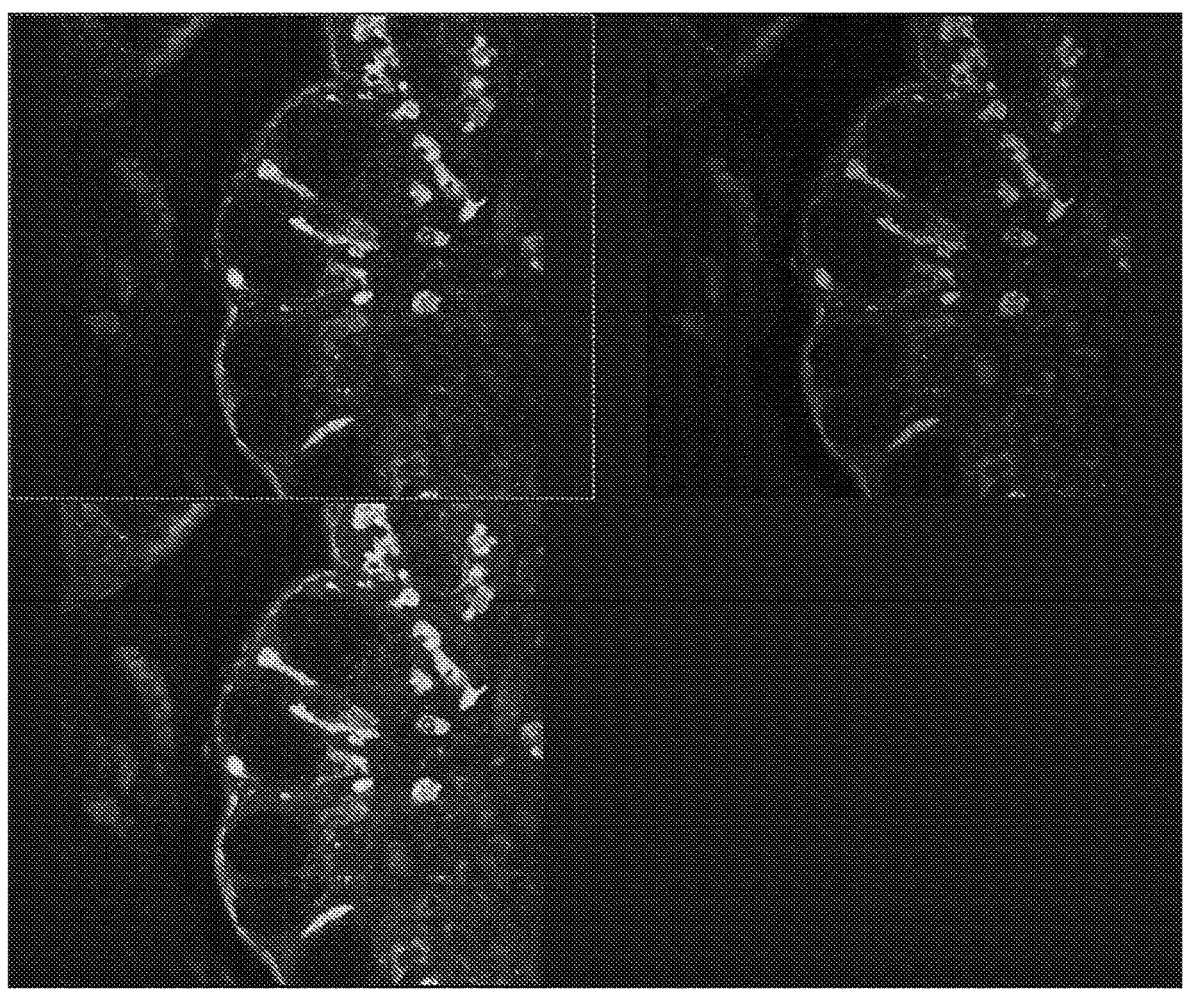
FIG. 3 shows the ileum of an individual with Crohn's disease stained using the A1 (red/top right) and A4 antibodies (green/top left). The bottom panel shows the two together.
Figure 4:
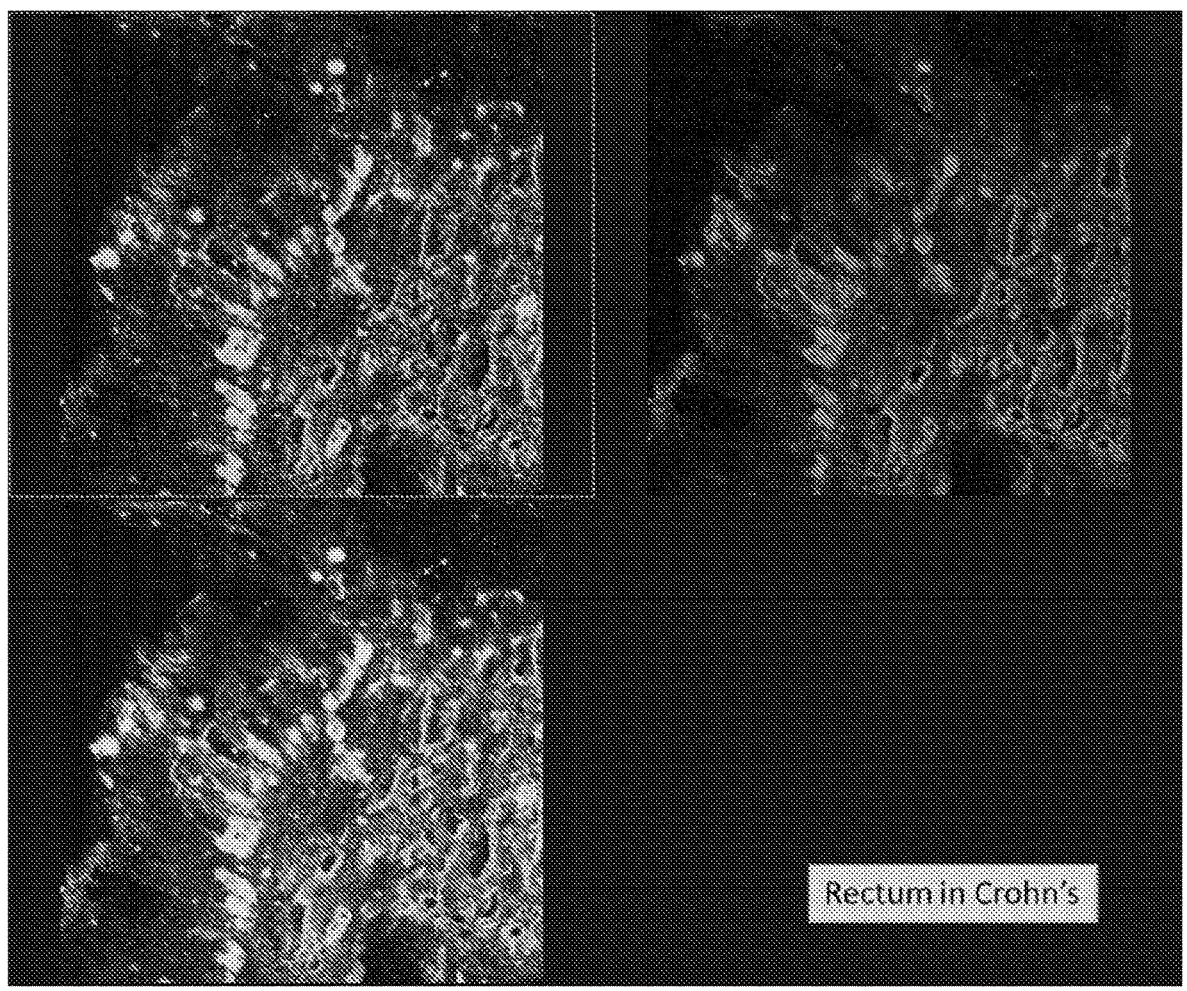
FIG. 4 shows the rectum of a 3 month old male child with Crohn's disease stained using the A1 (red/top right) and A4 antibodies (green/top left). The bottom panel shows the two together.

Suitable epitopes may thus be identified by routinely used methods such as those demonstrated in FIGS. 3 and 4 for identifying the strong T cell epitope GFAEINPIA (peptide 9.1) in the $5^{th}$ extracellular loop of mpa. In such a method, a library of short peptides which are fragments of the polypeptide sequence of interested may be generated and each of these peptides assessed separately for their ability to identify an immune response against the full length polypeptide. Members of the library may be screened in groups or pools or individual members of the library, such as individual members of a single pool, may be assessed separately.

In a further example, epitope scanning of the individual proteins of SEQ ID NOs: 32, 34, 36 and 40 revealed a number of predicted class I and class II epitopes.

In the ahpC variant sequence of SEQ ID NO: 32, predicted strong class II epitopes were identified at amino acids 48 to 56, 90 to 101 and 161 to 169. An ahpC polypeptide of the invention, such as an ahpC variant or fragment polypeptide, preferably comprises at least one, for example one, two or all three of these epitopes.

In the gsd variant sequence of SEQ ID NO: 34, predicted class I epitopes were identified at amino acids 1 to 32, 58 to 68, 99 to 119, 123 to 147, 159 to 169, 180 to 194 and 200 to 231, and predicted strong class II epitopes were identified at amino acids 64 to 76, 95 to 110, 192 to 206 and 223 to 240. A gsd polypeptide of the invention, such as a gsd variant or fragment polypeptide, preferably comprises at least one, for example one, two, three, four, five, six, seven, eight, nine, ten or all of these epitopes.

In the p12 variant sequence of SEQ ID NO: 36, predicted class I epitopes were identified at amino acids 33 to 56 and 98 to 117 and a predicted strong class II epitope was identified at amino acids 3 to 10. A p12 polypeptide of the invention, such as a p12 variant or fragment polypeptide, preferably comprises at least one, for example one, two or all three of these epitopes.

In the mpa variant sequence of SEQ ID NO: 40, a predicted class I epitope was identified at amino acids 130 to 160, and predicted strong class II epitopes were identified at amino acids 56 to 64 and 150 to 160. An mpa polypeptide of the invention, such as an mpa variant or fragment polypeptide, preferably comprises at least one, for example one, two or all three of these epitopes.

As shown in the Examples, a particular strong T cell epitope has been identified in the mpa polypeptide sequence. This epitope has the amino acid sequence GFAEINPIA and is located at amino acids 357 to 365 of SEQ ID NO: 30 and amino acids 177 to 185 of SEQ ID NO: 40. This sequence is found in the construct of SEQ ID NO: 42 at amino acids 761 to 769. A preferred mpa polypeptide sequence is a sequence which comprises GFAEINPIA. Such a sequence may also comprise one, two or all three of the predicted class I and class II epitopes mentioned above.

Figure 5:
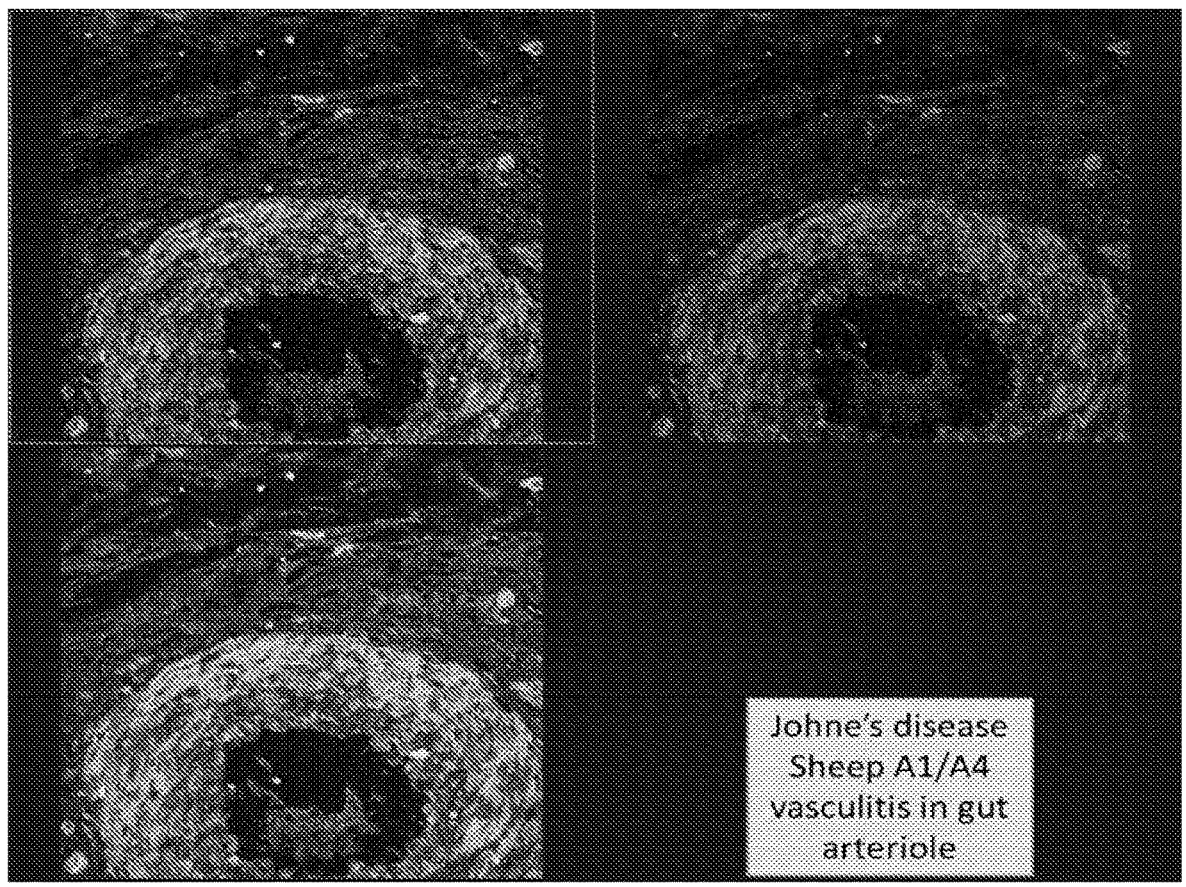
FIG. 5 shows a gut arteriole in a sheep with Johne's disease stained using the A1 (red/top right) and A4 antibodies (green/top left). The bottom panel shows the two together.
Figure 6:
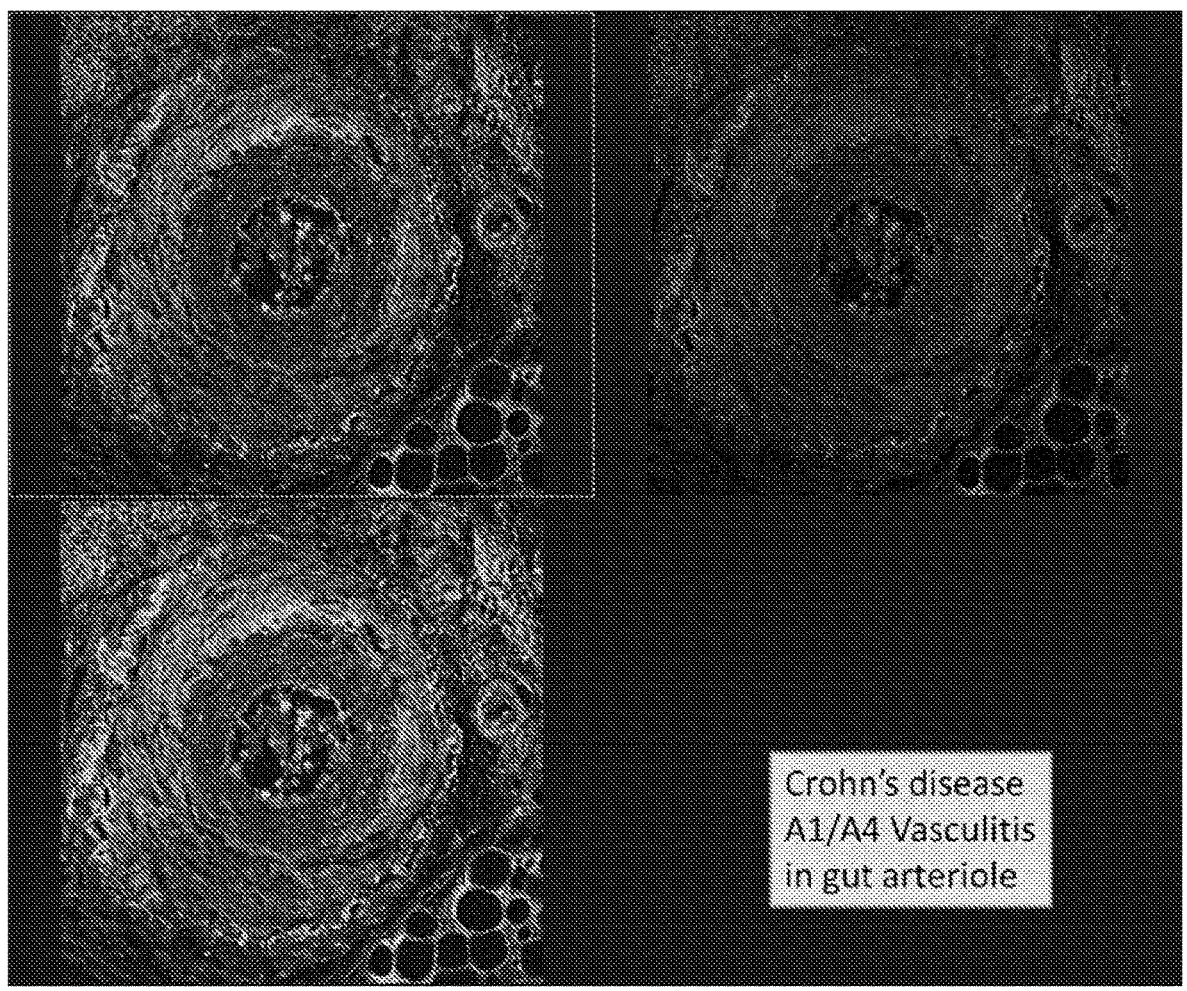
FIG. 6 shows a gut arteriole in an individual with Crohn's disease stained using the A1 (red/top right) and A4 antibodies (green/top left). The bottom panel shows the two together.
Figure 7:
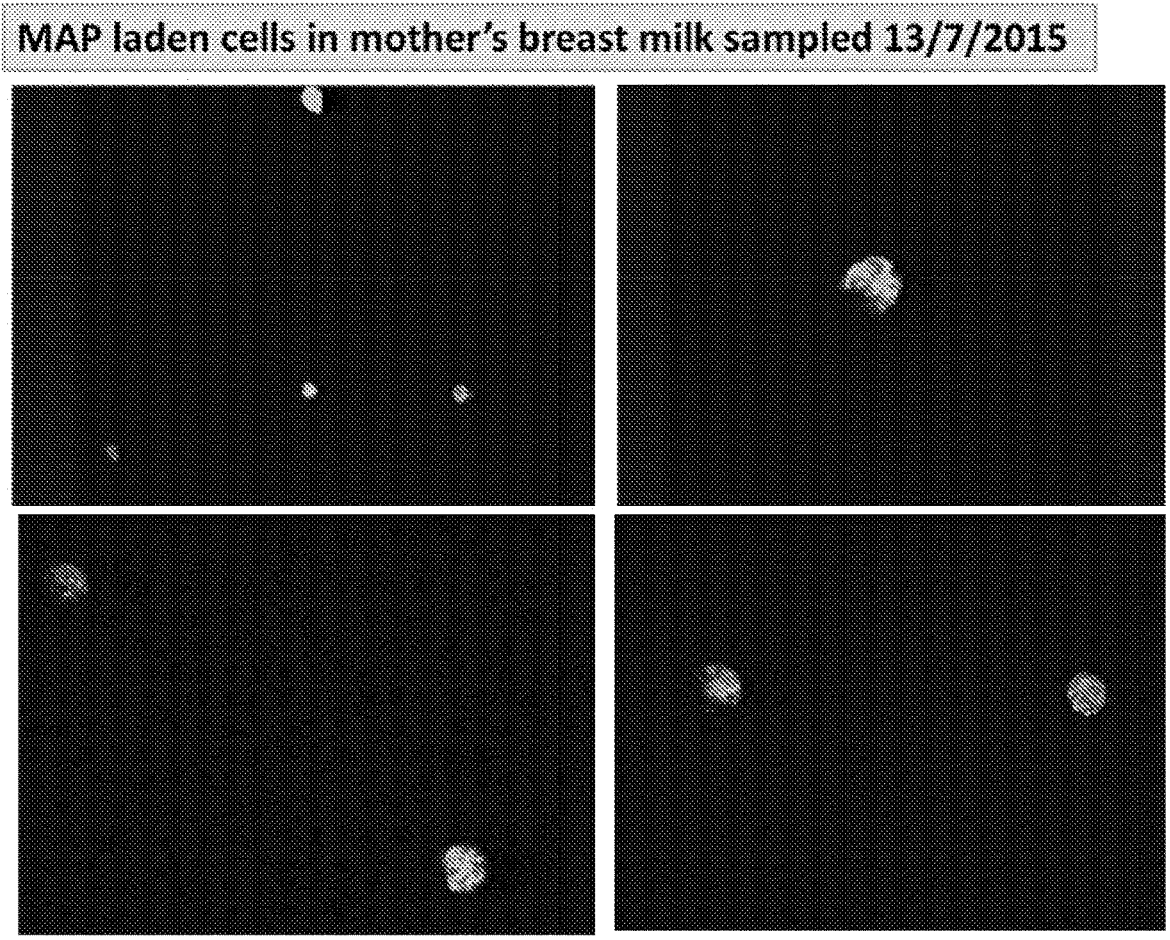
FIG. 7 shows MAP-laden white blood cells in breast milk stained using the A0X antibody.
Figure 8:
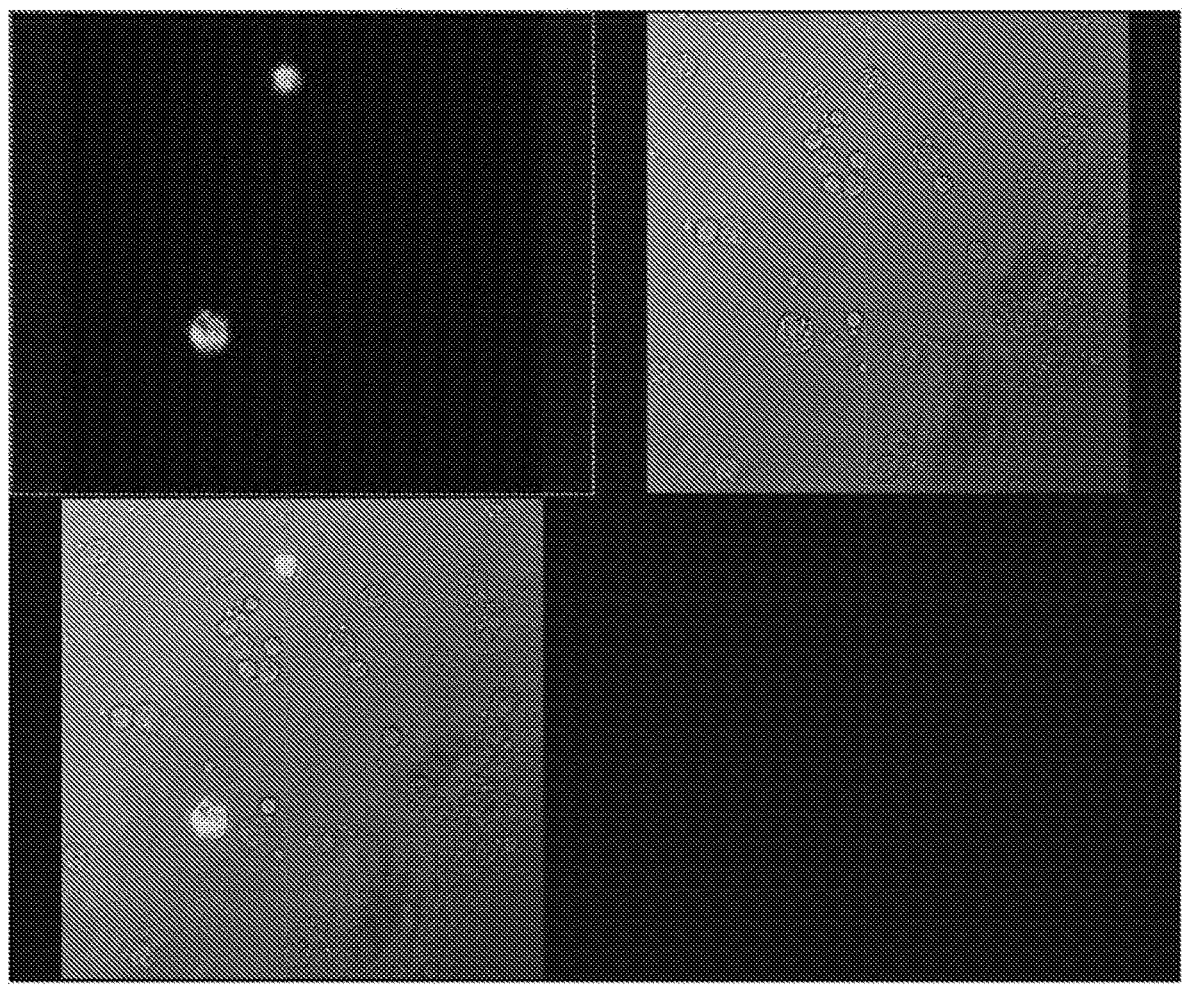
FIG. 8 shows MAP-Laden white blood cells in blood. A phase contrast image of the cells is shown (top right) and staining with the A0X antibody (top left). The bottom panel is an overlay of the two images.
Figure 9:
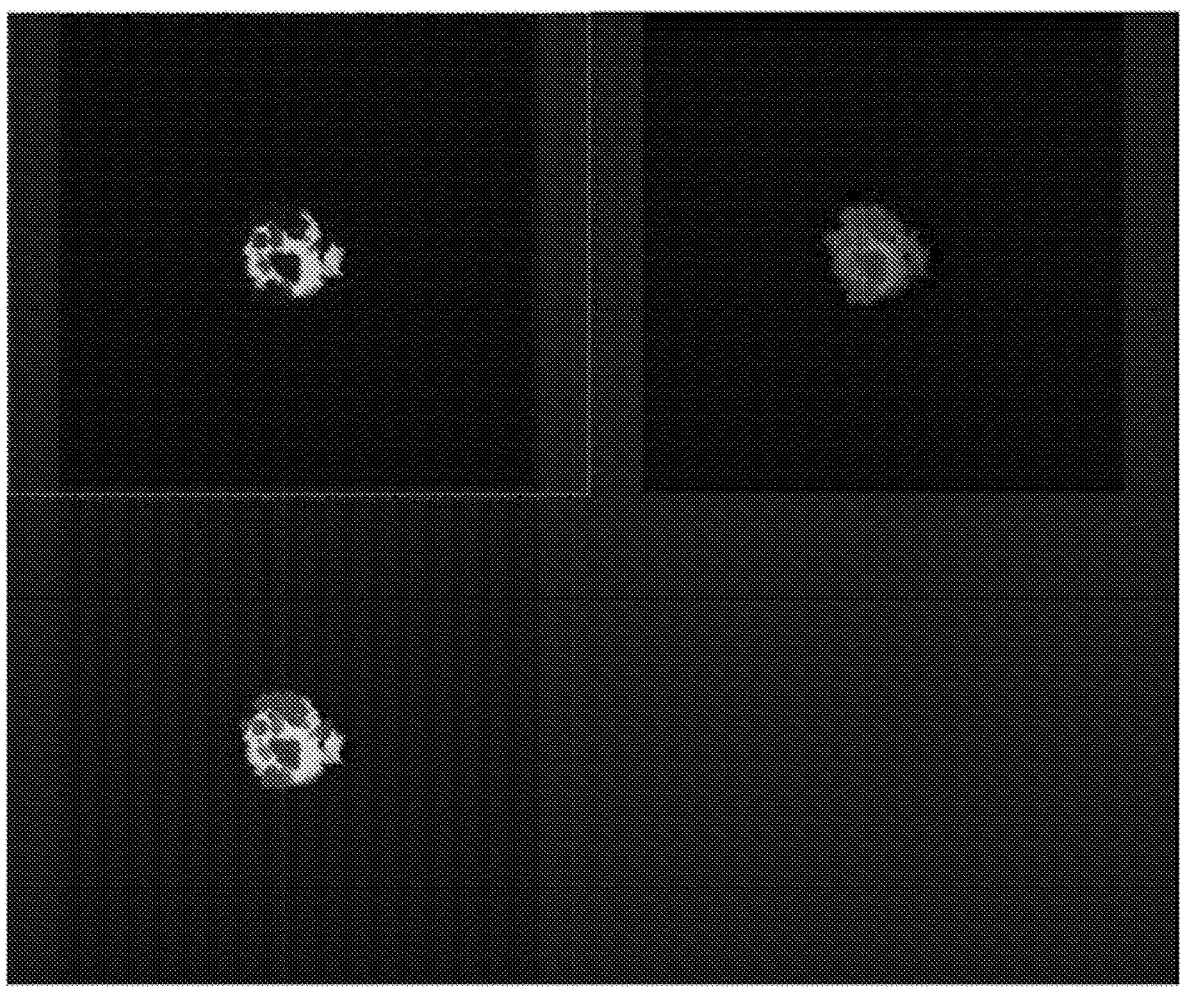
FIG. 9 shows a monocyte cell from the blood of a 25 year old man with severe Crohn's disease stained A4 in red (top right) and XA4P in green (top left). The cell is not perforated so staining is directed to the surface of the cell and almost certainly perturbs its function. The targets of the monoclonal antibodies contain the same amino acid sequence which includes 1 serine residue. This serine is not phosphorylated in the A4 target and is phosphorylated in the XA4P target. The phosphorylation event causes the targets to change their immunogenicity so that although they both crowd the cell surface in close apposition with one another they do not ad-mix. The use of A4 and XA4P monoclonal antibodies therefore allows the actions of the 2 MAP products to be used to trace the molecules and study their locations.

This epitope is believed to be located in the fifth extracellular loop of mpa (FIG. 5A). A preferred mpa polypeptide may therefore maintain the sequence of the fifth extracellular loop. An mpa polypeptide may therefore comprise the amino acid sequence GFAEINPIA and also adjacent amino acids from the fifth extracellular loop of mpa. Preferably, this fifth extracellular loop will be present in a polypeptide of the invention in a suitable form and conformation for it to be recognised by the immune system.

A peptide or polypeptide of the invention or for use in the invention may comprise further additional sequences, for example those encoded by the polynucleotides and vectors described below. For example, it may comprise additional epitopes, therapeutic polypeptides, adjuvants or immunomodulatory molecules.

The polypeptide may comprise a leader sequence, i.e. a sequence at or near the amino terminus of the polypeptide that functions in targeting or regulation of the polypeptide. For example a sequence may be included in the polypeptide that targets it to particular tissues in the body, or which helps the processing or folding of the polypeptide upon expression. Various such sequences are well known in the art and could be selected by the skilled reader depending upon, for example, the desired properties and production method of the polypeptide.

A polypeptide may further comprise a tag or label to identify or screen for the polypeptide, or for expression of the polypeptide. Suitable labels include radioisotopes such as $^{125}$I, $^{32}$P or $^{35}$S, fluorescent labels, enzyme labels, or other protein labels such as biotin. Suitable tags may be short amino acid sequences that can be identified by routine screening methods. For example, a short amino acid sequence may be included that is recognised by a particular monoclonal antibody.

The sequence given in SEQ ID NO: 40 or 41 comprises the four modified polypeptides of SEQ ID NOs: 32, 34, 36 or 37, and 40, and additional sequences such as a ubiquitin leader sequence and a pK tag.

Peptides of the invention, as defined herein, may be chemically modified, for example, post-translationally modified. For example they may be glycosylated or comprise modified amino acid residues. They can be in a variety of forms of polypeptide derivatives, including amides and conjugates with polypeptides.

Chemically modified peptides also include those having one or more residues chemically derivatized by reaction of a functional side group. Such derivatized side groups include those which have been derivatized to form amine hydrochlorides, p-toluene sulfonyl groups, carbobenzoxy groups, t-butyloxycarbonyl groups, chloroacetyl groups and formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Peptides may also be modified by phosphorylation, for example 3 amino phosphorylation and by glycosylation for example mannosylation.

Also included as chemically modified peptides are those which contain one or more naturally occurring amino acid derivatives of the twenty standard amino acids. For example, 4-hydroxyproline may be substituted for proline or homoserine may be substituted for serine.

The peptide of the invention or polypeptide or the polypeptides in the vaccine of the invention may be modified at the N-terminus and/or at the C-terminus and/or may be conjugated or coupled to a carrier molecule. Peptides/polypeptides may, for example, be conjugated to a bacterial saccharide or a carrier protein, such as keyhole limpet hemocyanin (KLH), bovine serum albumin (BSA), human serum albumin (HSA) or ovalbumin (OVA). The peptides may be biotinylated at the N-terminus or C-terminus, may be amidated at the N-terminus or C-terminus and/or may have a peptide tag added at the N-terminus or the C-terminus. The peptide tag may be, for example, a polylysine, such as a branched polylysine octamer, or a cell penetrating peptide such as an oligo-arginine (e.g. a polyarginine octamer or nonomer). Preferably, the peptide is biotinylated at the N-terminus and has an amide group or a branched polylysine octamer at the C-terminus. One or more additional amino acid residues may be added at the N-terminus and/or the C-terminus, optionally in addition to other terminal modifications. For example, one or more, such as two, alanine residues may be added at the N-terminus to increase immunogenicity and specificity and/or charged residues, for example GKK may be added at the N-terminus or preferably the C-terminus to reduce hydrophobicity. Where residues, such as GKK, are added at one terminus, the mirror image residues, such as KKG, may be added at the other terminus.

Peptide Linkers

The peptides and polypeptides of the invention may comprise two or more, such as 3, 4, 5, 6 or more fragments of MAP polypeptides joined together by one or more peptide linkers. The peptide linker may, for example, be any suitable multi-epitope vaccine linker. The linker may be, for example, from 1 to 15 amino acids in length, such as from 2 to 10, 3 to 6, or 4 to 5 amino acids in length. Specific examples of suitable linkers include: GGG, GG, SGSG, AG, GGGS, AAY, a dilysine linker (KK) EAAAK, AAY and HEYGAEALERAG.

Polynucleotides

The invention also relates to polynucleotide constructs comprising nucleic acid sequences which encode a peptide or polypeptide of the invention. For example, a single nucleic acid molecule may be provided which encodes any of the peptides or polypeptides, such as the fusion proteins, described above. The vaccine of the invention may comprise any one or more of the polynucleotides described herein.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, therefore, a polynucleotide of the invention comprises a nucleic acid sequence comprising all or part of any one of the sequences shown in SEQ ID NOs: 21, 31, 23, 33, 25, 35, 29, 39, 41, 62, 63, 64, 65, 67, 68 and 69. The nucleic acid sequence in the polynucleotide may alternatively be a variant of one of these specific sequences. For example, a variant may be a substitution, deletion or addition variant of any of the above nucleic acid sequences. A variant of one of the four genes may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to one of the MAP polynucleotides shown in SEQ ID NOs:1, 21, 23, 25, 27, 29, 31, 33, 35, 37, 39, 41, 62, 63, 64, 65, 67, 68 and 69 preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified MAP polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologues typically hybridize with the relevant polynucleotide at a level significantly above background. The signal level generated by the interaction between the homologue and the polynucleotide is typically at least 10 fold, preferably at least 100 fold, as intense as "background hybridisation". The intensity of interaction may be measured, for example, by radiolabelling the probe, e.g. with $^{32}$P. Selective hybridisation is typically achieved using conditions of medium to high stringency, (for example, 0.03M sodium chloride and 0.003M sodium citrate at from about 50° C. to about 60° C.

Stringent hybridization conditions can include 50% formamide, 5×Denhardt's Solution, 5×SSC, 0.1% SDS and 100 µg/ml denatured salmon sperm DNA and the washing conditions can include 2×SSC, 0.1% SDS at 37° C. followed by 1×SSC, 0.1% SDS at 68° C. Defining appropriate hybridization conditions is within the skill of the art. See, e.g., Sambrook et al., supra.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

In one embodiment the coding sequence of the polynucleotide construct may be optimised to more closely resemble the codon usage of highly expressed genes in mammalian cells. Where more than one codon is available to code for a given amino acid, it has been observed that the codon usage patterns of organisms are highly non-random. Different species show a different bias in their codon selection and, furthermore, utilization of codons may be markedly different in a single species between genes which are expressed at high and low levels. This bias is different in viruses, plants, bacteria and mammalian cells, and some species show a stronger bias away from a random codon selection than others.

For example, humans and other mammals are less strongly biased than certain bacteria or viruses. For these reasons, it is possible that, for example a mycobacterial gene expressed in mammalian cells will have an inappropriate distribution of codons for efficient expression. It is believed that the presence in a heterologous DNA sequence of clusters of codons which are rarely observed in the host in which expression is to occur, is predictive of low heterologous expression levels in that host.

In the polynucleotide of the invention, the codon usage pattern may therefore be altered from that found naturally in MAP to more closely represent the codon bias of the target organism, e.g. a mammal, especially a human. The "codon usage coefficient" is a measure of how closely the codon pattern of a given polynucleotide sequence resembles that of a target species. Codon frequencies can be derived from literature sources for the highly expressed genes of many species (see e.g. Nakamura et. al. Nucleic Acids Research 1996, 24:214-215). The codon frequencies for each of the 61 codons (expressed as the number of occurrences occurrence per 1000 codons of the selected class of genes) are normalised for each of the twenty natural amino acids, so that the value for the most frequently used codon for each amino acid is set to 1 and the frequencies for the less common codons are scaled to lie between zero and 1. Thus each of the 61 codons is assigned a value of 1 or lower for the highly expressed genes of the target species. In order to calculate a codon usage coefficient for a specific polynucleotide, relative to the highly expressed genes of that species, the scaled value for each codon of the specific polynucleotide are noted and the geometric mean of all these values is taken (by dividing the sum of the natural logs of these values by the total number of codons and take the anti-log). The coefficient will have a value between zero and 1 and the higher the coefficient the more codons in the polynucleotide are "frequently used codons". If a polynucleotide sequence has a codon usage coefficient of 1, all of the codons are "most frequent" codons for highly expressed genes of the target species.

According to the present invention, the codon usage pattern of the polynucleotide of the invention will preferably exclude codons with a relative synonymous codon usage (RSCU) value of less than 0.2 in highly expressed genes of the target organism. A RSCU value is the observed number of codons divided by the number expected if all codons for that amino acid were used equally frequently. The polynucleotide of the invention will generally have a codon usage coefficient for highly expressed human genes of greater than 0.3, preferably greater than 0.4, most preferably greater than 0.5. Codon usage tables for human can also be found in GenBank.

It can thus be seen that the particular polynucleotide sequence which encodes a polypeptide of the invention may be altered to optimise the codons based on the species to be treated. As an example of this, the MAP sequences given in SEQ ID Nos: 21, 23, 25 and 29 have been codon optimised for human use in the polynucleotides of SEQ ID Nos: 31, 33, and 35. Such modifications may improve the ability of such polynucleotides to express their encoded proteins in a human cell.

As explained above in relation to polypeptides, the polynucleotides of the invention may also be modified to disable or remove potential cross-reacting epitopes in the encoded polypeptide.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. For example, a variant of the invention may encode a polypeptide that consists of or comprises two or more epitope regions from a full length polypeptide of the invention in the absence of non-epitope amino acids. Preferably a fragment of an ahpC, gsd, p12 or mpa polynucleotide sequence comprises at least one region encoding an epitope capable of inducing an immune response against the unmodified MAP polypeptide. Such fragments may be derived from a sequence of SEQ ID NO: 21, 31, 23, 33, 25, 35, 29 or 39 or may be derived from a variant polynucleotide as described herein. Preferably such fragments are between 24 and 500 residues in length, e.g. 24 to 400, 24 to 300, 24 to 100, 100 to 200 or 200 to 400 residues. Alternatively, fragments of the invention may be longer sequences, for example comprising at least 50%, at least 60%, at least 70%, at least 80% or at least 90% of a full length polynucleotide of the invention.

A peptide of the invention may thus be produced from or delivered in the form of a polynucleotide which encodes, and is capable of expressing, it. Polynucleotides of the invention can be synthesised according to methods well known in the art, as described by way of example in Sambrook et al (1989, Molecular Cloning—a laboratory manual; Cold Spring Harbor Press). Substantially pure antigen preparations can be obtained using standard molecular biological tools. That is, polynucleotide sequences coding for the above-described moieties can be obtained using recombinant methods, such as by screening cDNA and genomic libraries from cells expressing an antigen, or by deriving the coding sequence for a polypeptide from a vector known to include the same. Furthermore, the desired sequences can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al. (1987) Methods Enzymol. 155:335-350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once the sequences have been obtained, they may be linked together to provide a nucleic acid molecule using standard cloning or molecular biology techniques. Alternatively, the sequences can be produced synthetically, rather than cloned. The nucleotide sequence can be designed with the appropriate codons for the particular amino acid sequence desired. As explained herein, one will generally select preferred codons for the intended host in which the sequence will be expressed. The complete sequence can then be assembled from overlapping oligonucleotides prepared by standard methods and assembled into a complete coding sequence.

Vectors

The nucleic acid molecules of the present invention may be provided in the form of an expression cassette which includes control sequences operably linked to the inserted sequence, thus allowing for expression of the polypeptide of the invention in vivo in a targeted subject species. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

Promoters and other expression regulation signals may be selected to be compatible with the host cell for which expression is designed. For example, yeast promoters include S. cerevisiae GAL4 and ADH promoters, S. pombe nmt1 and adh promoter. Mammalian promoters, such as β-actin promoters, may be used. Tissue-specific promoters are especially preferred. Mammalian promoters include the metallothionein promoter which can be induced in response to heavy metals such as cadmium.

In one embodiment a viral promoter is used to drive expression from the polynucleotide. Typical viral promoters for mammalian cell expression include the SV40 large T antigen promoter, adenovirus promoters, the Moloney murine leukaemia virus long terminal repeat (MMLV LTR), the mouse mammary tumor virus LTR promoter, the rous sarcoma virus (RSV) LTR promoter, the SV40 early promoter, the human cytomegalovirus (CMV) IE promoter, adenovirus, including the adenovirus major late promoter (Ad MLP), HSV promoters (such as the HSV IE promoters), or HPV promoters, particularly the HPV upstream regulatory region (URR). All these promoters are readily available in the art.

In one embodiment, the promoter is a Cytomegalovirus (CMV) promoter. A preferred promoter element is the CMV immediate early (IE) promoter devoid of intron A, but including exon 1. Thus the expression from the polynucleotide may be under the control of hCMV IE early promoter. Expression vectors using the hCMV immediate early promoter include for example, pWRG7128, and pBC12/CMV and pJW4303. A hCMV immediate early promoter sequence can be obtained using known methods. A native hCMV immediate early promoter can be isolated directly from a sample of the virus, using standard techniques. U.S. Pat. No. 5,385,839, for example, describes the cloning of a hCMV promoter region. The sequence of a hCMV immediate early promoter is available at Genbank #M60321 (hCMV Towne strain) and X17403 (hCMV Ad169 strain). A native sequence could therefore be isolated by PCR using PCR primers based on the known sequence. See e.g. Sambrook et al, supra, for a description of techniques used to obtain and isolate DNA. A suitable hCMV promoter sequence could also be isolated from an existing plasmid vector. Promoter sequences can also be produced synthetically.

A polynucleotide, expression cassette or vector of the invention may comprise an untranslated leader sequence. In general the untranslated leader sequence has a length of from about 10 to about 200 nucleotides, for example from about 15 to 150 nucleotides, preferably 15 to about 130 nucleotides. Leader sequences comprising, for example, 15, 50, 75 or 100 nucleotides may be used. Generally a functional untranslated leader sequence is one which is able to provide a translational start site for expression of a coding sequence in operable linkage with the leader sequence.

Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the expression cassette or vector.

Expression systems often include transcriptional modulator elements, referred to as "enhancers". Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters), and may operate when positioned in either orientation relative to the sequence of interest. Enhancers have been identified from a number of viral sources, including polyoma virus, BK virus, cytomegalovirus (CMV), adenovirus, simian virus 40 (SV40), Moloney sarcoma virus, bovine papilloma virus and Rous sarcoma virus. Examples of suitable enhancers include the SV40 early gene enhancer, the enhancer/promoter derived from the long terminal repeat (LTR) of the Rous Sarcoma Virus, and elements derived from human or murine CMV, for example, elements included in the CMV intron A sequence.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus.

Nucleic acids encoding for polypeptides known to display antiviral or antibacterial activity, immunomodulatory molecules such as cytokines (e.g. TNF-alpha, interferons such as IL-6, and IL-2, interferons, colony stimulating factors such as GM-CSF), adjuvants and co-stimulatory and accessory molecules (B7-1, B7-2) may be included in a polynucleotide, expression cassette or vector of the invention. Alternatively, such polypeptides may be provided separately, for example in a formulation comprising a molecule of the invention, or may be administered simultaneously, sequentially or separately with a composition of the invention. Concurrent provision of an immunomodulatory molecule and a polypeptide of the invention at a site in vivo may enhance the generation of specific effectors which may help to enhance the immune response. The degree of enhancement of the immune response may be dependent upon the specific immunostimulatory molecules and/or adjuvants used because different immunostimulatory molecules may elicit different mechanisms for enhancing and/or modulating the immune response. By way of example, the different effector mechanisms/immunomodulatory molecules include but are not limited to augmentation of help signal (IL-2), recruitment of professional APC (GM-CSF), increase in T cell frequency (IL-2), effect on antigen processing pathway and MHC expression (IFN-gamma and TNF-alpha) and diversion of immune response away from the Th1 response and towards a Th2 response. Unmethylated CpG containing oligonucleotides are also preferential inducers of a Th1 response and are suitable for use in the present invention.

In some embodiments, the polynucleotide, expression cassette or vector will encode an adjuvant, or an adjuvant will otherwise be provided. As used herein, the term "adjuvant" refers to any material or composition capable of specifically or non-specifically altering, enhancing, directing, redirecting, potentiating or initiating an antigen-specific immune response.

A suitable adjuvant may be an ADP-ribosylating bacterial toxin. These include diphtheria toxin (DT), pertussis toxin (PT), cholera toxin (CT), the E. coli heat labile toxins (LT1 and LT2), Pseudomonas endotoxin A, Pseudomonas exotoxin S, B. cereus exoenzyme, B. sphaericus toxin, C. botulinum C2 and C3 toxins, C. limosum exoenzyme, as well as toxins from C. perfringens, C. spiriforma and C. difficile and Staphylococcus aureus EDIN. Most ADP-ribosylating bacterial toxins contain A and B subunits.

Polynucleotides of interest may be used in vitro or in vivo in the production of a peptide of the invention. Such polynucleotides may be administered or used in the manufacture of a medicament for the treatment of Crohn's disease or another disease or condition characterised by the expression of MAP.

Gene therapy and nucleic acid immunization are approaches which provide for the introduction of a nucleic acid molecule encoding one or more selected antigens into a host cell for the in vivo expression of the antigen or antigens. Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells which have been removed from a subject. In this latter case, cells containing the nucleic acid molecule of interest are re-introduced into the subject such that an immune response can be mounted against the antigen encoded by the nucleic acid molecule. The nucleic acid molecules used in such immunization are generally referred to herein as "nucleic acid vaccines."

Each of these delivery techniques requires efficient expression of the nucleic acid in the transfected cell, to provide a sufficient amount of the therapeutic or antigenic gene product. Several factors are known to affect the levels of expression obtained, including transfection efficiency, and the efficiency with which the gene or sequence of interest is transcribed and the mRNA translated.

The agent produced by a host cell may be secreted or may be contained intracellularly depending on the polynucleotide and/or the vector used. As will be understood by those of skill in the art, expression vectors containing the polynucleotides of the invention can be designed with signal sequences which direct secretion of the polypeptide expressed from the vector through a particular prokaryotic or eukaryotic cell membrane.

The vectors and expression cassettes of the present invention may be administered directly as "a naked nucleic acid construct", preferably further comprising flanking sequences homologous to the host cell genome. As used herein, the term "naked DNA" refers to a vector such as a plasmid comprising a polynucleotide of the present invention together with a short promoter region to control its production. It is called "naked" DNA because the vectors are not carried in any delivery vehicle. When such a vector enters a host cell, such as a eukaryotic cell, the proteins it encodes are transcribed and translated within the cell.

The vector of the invention may thus be a plasmid vector, that is, an autonomously replicating, extrachromosomal circular or linear DNA molecule. The plasmid may include additional elements, such as an origin of replication, or selector genes. Such elements are known in the art and can be included using standard techniques. Numerous suitable expression plasmids are known in the art. For example, one suitable plasmid is pSG2. This plasmid was originally isolated from *Streptomyces ghanaensis*. The length of 13.8 kb, single restriction sites for HindIII, EcoRV and PvuII and the possibility of deleting non-essential regions of the plasmid make pSG2 a suitable basic replicon for vector development.

Alternatively, the vectors of the present invention may be introduced into suitable host cells using a variety of viral techniques which are known in the art, such as for example infection with recombinant viral vectors such as retroviruses, herpes simplex viruses and adenoviruses.

In one embodiment, the vector itself may be a recombinant viral vector. Suitable recombinant viral vectors include but are not limited to adenovirus vectors, adeno-associated viral (AAV) vectors, herpes-virus vectors, a retroviral vector, lentiviral vectors, baculoviral vectors, pox viral vectors or parvovirus vectors. In the case of viral vectors, administration of the polynucleotide is mediated by viral infection of a target cell.

A number of viral based systems have been developed for transfecting mammalian cells.

For example, a selected recombinant nucleic acid molecule can be inserted into a vector and packaged as retroviral particles using techniques known in the art. The recombinant virus can then be isolated and delivered to cells of the subject either in vivo or ex vivo. Retroviral vectors may be based upon the Moloney murine leukaemia virus (Mo-MLV). In a retroviral vector, one or more of the viral genes (gag, pol & env) are generally replaced with the gene of interest.

A number of adenovirus vectors are known. Adenovirus subgroup C serotypes 2 and 5 are commonly used as vectors. The wild type adenovirus genome is approximately 35 kb of which up to 30 kb can be replaced with foreign DNA. There are four early transcriptional units (E1, E2, E3 & E4), which have regulatory functions, & a late transcript, which codes for structural proteins. Adenovirus vectors may have the E1 and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include Ad5 vectors and simian adenovirus vectors. For example, ChAdOx2, which is a is a simian-derived non-replicative vaccine vector developed by Oxford University for use in humans minimising cross reactivity to any pre-existing adenoviral immunity (Morris et al. *Future Virol.* 2016; 11(9):649-659) may be used. In some embodiments, a polynucleotide encoding any one of the above-described polypeptides, such as for example a polypeptide having the sequence shown in any one of SEQ ID NOs: 41 and 62 to 69, may by inserted into a ChAdOx2 vector in the same manner as the HAV ChAdOx2 vaccine construct containing HAV and expressing the MAP genes AhpC, Gsd, p12 and mpa described in (Morris et al. *Future Virol.* 2016; 11(9): 649-659).

Viral vectors may also be derived from the pox family of viruses, including vaccinia viruses and avian poxvirus such as fowlpox vaccines. For example, modified vaccinia virus Ankara (MVA) is a strain of vaccinia virus which does not replicate in most cell types, including normal human tissues. A recombinant MVA vector may therefore be used to deliver the polypeptide of the invention.

Addition types of virus such as adeno-associated virus (AAV) or herpes simplex virus (HSV) may also be used to develop suitable vector systems.

As an alternative to viral vectors, liposomal preparations can alternatively be used to deliver the nucleic acid molecules of the invention. Useful liposomal preparations include cationic (positively charged), anionic (negatively charged) and neutral preparations, with cationic liposomes particularly preferred. Cationic liposomes may mediate intracellular delivery of plasmid DNA and mRNA.

As another alternative to viral vector systems, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). Other particulate systems and polymers can also be used, for example, polymers such as polylysine, polyarginine, polyornithine, spermine, spermidine, as well as conjugates of these molecules.

In one embodiment, the vector may be a targeted vector, that is a vector whose ability to infect or transfect or transduce a cell or to be expressed in a host and/or target cell is restricted to certain cell types within the host subject, usually cells having a common or similar phenotype.

In one embodiment, the vector of the invention may comprise a single expression cassette, from which a single polypeptide sequence can be expressed. Alternatively, a vector of the invention may comprise two or more expression cassettes each capable of expressing a different polypeptide, such that the vector as a whole is capable of expressing all required polypeptides. Where the polypeptides are expressed from more than one locus in the vector, or are expressed as multiple separate molecules, the expression of the multiple sequences is preferably coordinated such that all polypeptides are expressed together. For example, the same or similar promoters may be used to control expression of the various components. Inducible promoters may be used so that expression of the various polypeptide components can be coordinated.

Cell Lines

The invention also includes cells that have been modified to express a peptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a peptide of the invention include mammalian HEK293T, CHO, HeLa and COS cells. Preferably the cell line selected will be one which is not only stable, but also allows for mature glycosylation and cell surface expression of a polypeptide. Expression may be achieved in transformed oocytes. A suitable peptide may be expressed in cells of a transgenic non-human animal, preferably a mouse. A transgenic non-human animal expressing a peptide of the invention is included within the scope of the invention. A peptide of the invention may also be expressed in *Xenopus laevis* oocytes or melanophores.

Such cell lines of the invention may be cultured using routine methods to produce a polypeptide of the invention, or may be used therapeutically or prophylactically to deliver polypeptides of the invention to a subject. For example, cell lines capable of secreting a polypeptide of the invention may be administered to a subject. Alternatively, polynucleotides, expression cassettes or vectors of the invention may be administered to a cell from a subject ex vivo and the cell then returned to the body of the subject.

For example, methods for the ex vivo delivery and reimplantation of transformed cells into a subject are known (e.g., dextran-mediated transfection, calcium phosphate precipitation, electroporation, and direct microinjection into nuclei).

Pharmaceutical Compositions

Formulation of a composition comprising a peptide, polypeptide, polynucleotide or vector as described above, can be carried out using standard pharmaceutical formulation chemistries and methodologies all of which are readily available to the reasonably skilled artisan. For example, compositions containing one or more molecules of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Certain facilitators of nucleic acid uptake and/or expression ("transfection facilitating agents") can also be included in the compositions, for example, facilitators such as bupivacaine, cardiotoxin and sucrose, and transfection facilitating vehicles such as liposomal or lipid preparations that are routinely used to deliver nucleic acid molecules. Anionic and neutral liposomes are widely available and well known for delivering nucleic acid molecules (see, e.g., Liposomes: A Practical Approach, (1990) RPC New Ed., IRL Press). Cationic lipid preparations are also well known vehicles for use in delivery of nucleic acid molecules. Suitable lipid preparations include DOTMA (N-[1-(2,3-dioleyloxy)propyl]-N,N,N-trimethylammonium chloride), available under the tradename Lipofectin™, and DOTAP (1,2-bis(oleyloxy)-3-(trimethylammonio)propane), see, e.g., Felgner et al. (1987) Proc. Natl. Acad. Sci. USA 84:7413-7416; Malone et al. (1989) Proc. Natl. Acad. Sci. USA 86:6077-6081; U.S. Pat. Nos. 5,283,185 and 5,527,928, and International Publication Nos WO 90/11092, WO 91/15501 and WO 95/26356. These cationic lipids may preferably be used in association with a neutral lipid, for example DOPE (dioleyl phosphatidylethanolamine). Still further transfection-facilitating compositions that can be added to the above lipid or liposome preparations include spermine derivatives (see, e.g., International Publication No. WO 93/18759) and membrane-permeabilizing compounds such as GALA, Gramicidine S and cationic bile salts (see, e.g., International Publication No. WO 93/19768).

Alternatively, the nucleic acid molecules of the present invention may be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulated compositions will include an amount of the molecule (e.g. vector) of interest which is sufficient to mount an immunological response. An appropriate effective amount can be readily determined by one of skill in the art. Such an amount will fall in a relatively broad range that can be determined through routine trials. The compositions may contain from about 0.1% to about 99.9% of the vector and can be administered directly to the subject or, alternatively, delivered ex vivo, to cells derived from the subject, using methods known to those skilled in the art.

The vaccine may in one aspect be peptide vaccine. In one embodiment the peptide(s) in the vaccine may be delivered using any suitable delivery system, for example an emulsion based delivery system, a liposome based delivery system, a virosome based delivery system, a transfersome based delivery system, an archeosome based delivery system, a niosome based delivery system, a cochleate based delivery system and/or a particulate delivery system.

The peptide may be administered with an adjuvant, or the vaccine may include an adjuvant. The adjuvant may, for example, be selected from Freund's complete adjuvant (CFA or FCA), Freund's incomplete adjuvant (IFA or FIA), Montanide™ ISA 720, ISCOMs, ISCOMATRIX™. Particulate delivery systems can also serve as adjuvants. The particulate delivery system may comprise nanoparticles. The nanoparticles may, for example be made of a natural polymer such as albumin, collagen, starch, chitosan or dextran, or of synthetic polymer such as polylactides (PLA), polyglycolides or polyglocolic acid (PGA) and their copolymers poly(lactide-co-glycolide) PLGA, poly(e-caprolactone) (PCL), poly(hydroxybutyrate) (PHB) and their copolymers. The nanoparticles may, alternatively, be carbon nanotubes, silicon dioxide nanoparticles, dendrimers, ferritin nanoparticles, peptide nanocarriers, gold nanoparticles, liposome-polycation-DNA (LPD) complex, oligosaccharide ester derivatives (OEDs) microparticles and combination systems.

Therapeutic Methods

The vaccine, peptides, polypeptides, polynucleotides and vectors disclosed herein can be used in the treatment or prevention of infection by MAP, or in the treatment or prevention of any disease, condition or symptom which is associated with MAP infection, that is any disease condition or symptom which is a direct or indirect result of MAP infection, or which results from a disease or condition to which the presence of MAP contributes. MAP is known to be linked to numerous specific medical conditions, such as chronic inflammation of the intestine, including inflammatory bowel disease and as well as Irritable Bowel Syndrome. For example, MAP infection can cause chronic enteritis, such as Johne's disease (paratuberculosis) in livestock and Crohn's disease and Irritable Bowel Syndrome in humans. Other diseases or conditions associated with MAP include, but are not limited to, Parkinson's disease, Alzheimer's disease, Multiple Sclerosis, Irritable Bowel Syndrome, Ulcerative colitis, type 1 Diabetes Mellitus, Thyroiditis, Rheumatoid arthritis, Psoriasis, Ankylosing Spondylitis, Sarcoidosis, Idiopathic Pulmonary Fibrosis, Chronic Fatigue Syndrome and other complex disorders with a chronic autoimmune inflammatory component. The vaccine, peptides, polypeptides, polynucleotides and vectors disclosed herein may therefore be used in the prevention or treatment of any of these specific conditions.

The subject being treated may in some instances be identified by a clinical diagnostic for MAP infection. In one embodiment, the MAP infection is detected by a clinically-applicable simple diagnostic for human and animal MAP infection using monoclonal antibodies as described in International Patent Application No. PCT/GB2018/050075, which is incorporated herein by reference in its entirety. For example, one or two pairs of mutually-exclusive monoclonal antibodies that target specific peptide sequences in the accessible amino- and carboxy-terminal extracellular domains of the multi-copy IS900-encoded protein may be used to detect MAP in a sample from a subject. In this diagnostic test, one antibody of a pair recognises the native peptide sequence and the other its phosphorylated derivative. Simultaneous use of two or more differentially fluorophore-labelled monoclonals results for the first time in bright clear images of MAP packing the cytoplasm of MAP infected host cells and displayed on infected cell surfaces. The diagnostic method may, for example, use a pair of monoclonal antibodies directed to MVINDDAQRLLSQR and MVINDDAQRLL[pS]QR and/or a pair of monoclonal antibodies directed to YLSALVSIRTDPSSR and YLSALVSIRTDPS[pS]R. The antibodies may for example be labelled with the same or different fluorophores.

Flow Cytometry of blood samples using of these pairs of specific co-localising monoclonal antibodies provides a simple accurate detection method that allows quantification of MAP-infected circulating white blood cells and their subtypes. Use of these fluorophore labelled antibodies on tissue samples such as endoscopic biopsies and surgically resected tissues reveals strong images of brightly lit MAP infected cells and their distribution and host cell subtypes.

These specific reagents and resulting new clinical MAP tests on blood and tissues have shown that everyone with Crohn's disease is infected with MAP. The methods and reagents provide for the first time simple accurate tests for the diagnosis and quantification of MAP infection in humans and animals. They can also be applied to clinical screening blood and tissue samples from people with other diseases where MAP is a candidate pathogen like Parkinson's disease, Alzheimer's disease, Multiple Sclerosis, Irritable Bowel Syndrome, Ulcerative colitis, type 1 Diabetes Mellitus, Thyroiditis, Rheumatoid arthritis, Psoriasis, Ankylosing Spondylitis, Sarcoidosis, Idiopathic Pulmonary Fibrosis, Chronic Fatigue Syndrome and other complex disorders with a chronic autoimmune inflammatory component (Hui K Y et al. 2018; Sci. Transl. Med. 10, eaai7795; Hütlova A et al. al. 2018. The EMBO Journal e98694).

Accordingly, the present invention relates to a vaccine, peptide, polypeptide, polynucleotide, vector, cell or composition as disclosed herein for use in a method of therapy, in particular in a method or treating or preventing a disease, disorder or symptoms associated with or caused by a MAP infection. These molecules of the invention may thus also be used in the manufacture of a medicament for treating or preventing such a disease, disorder or condition. Thus, the present invention also encompasses the use of a vaccine, peptide, polypeptide, polynucleotide or vaccine vector according to the invention in the manufacture of a medicament for treating or preventing MAP infection or a condition or symptom associated with MAP infection. In particular, the molecules of the invention are proposed for the treatment or prevention of a chronic inflammation of the intestine, preferably in a mammal such as a human, cow, sheep or goat. The invention thus also provides a method of treating or preventing any such disease, disorder or symptom comprising administering to a subject in need thereof a polypeptide, polynucleotide, expression cassette, vector, cell, antibody or composition of the invention.

The present invention is broadly applicable to vaccination methods and is relevant to the development of prophylactic and/or therapeutic vaccines (including immunotherapeutic vaccines). It is to be appreciated that all references herein to treatment include curative, palliative and prophylactic treatment.

According to the present invention, the peptide, polynucleotide, vector, or vaccine may be employed alone as part of a composition, such as but not limited to a pharmaceutical composition or a vaccine composition or an immunotherapeutic composition to prevent and/or treat a condition associated with MAP infection. The administration of the composition may be for either "prophylactic" or "therapeutic" purpose. As used herein, the term "therapeutic" or "treatment" includes any of following: the prevention of infection or reinfection; the reduction or elimination of symptoms; and the reduction or complete elimination of a pathogen. Treatment may be effected prophylactically (prior to infection) or therapeutically (following infection).

Prophylaxis or therapy includes but is not limited to eliciting an effective immune response to a polypeptide of the invention and/or alleviating, reducing, curing or at least partially arresting symptoms and/or complications resulting from or associated with a MAP infection. When provided prophylactically, the composition of the present invention is typically provided in advance of any symptom. The prophylactic administration of the composition of the present invention is to prevent or ameliorate any subsequent infection or disease. When provided therapeutically, the composition of the present invention is typically provided at or shortly after the onset of a symptom of infection or disease. Thus the composition of the present invention may be provided either prior to the anticipated exposure to MAP or onset of the associated disease state or after the initiation of an infection or disease.

The vaccine is typically considered to be prophylactically effective if it reduces the MAP load in a vaccinated subject compared to an un-vaccinated subject after post-vaccination challenge with MAP. Where the subject is infected with MAP prior to vaccination, the vaccine is typically considered to be effective if MAP load is reduced compared to before vaccination. MAP load in blood or tissues may be determined. The MAP and/or MAP components, e.g. peptides or proteins, may be present on the surface of cells or intracellularly within the cytoplasm. MAP expression may be determined by antibody staining (WO 2018/130836).

The effectiveness of the vaccine may be determined in any suitable way. For example, changes in cytokine expression, T-cell activation, antibody production and/or peripheral blood mononuclear cell (PBMC) MAP-killing may be used to determine the effectiveness of the vaccine. Where cytokine expression is monitored, for example, a decrease in inhibitory cytokine production, such as IL-10 production, is a desirable effect. The generation of T-cells specific for epitopes in the vaccine may, for example, be detected by stimulating T-cells ex vivo with a peptide present in the vaccine and detecting IFN-γ release, for example using an ELISpot or ELISA assay. Suitable assays for detecting antibodies specific to the polypeptide in the vaccine, for example, antibodies to one or more peptides present in the vaccine, are known in the art. Similarly, ex vivo assays for monitoring PBMC MAP-killing are known.

Subject to be Treated

The present invention relates in particular to the treatment or prevention of diseases or other conditions which are associated with infection by MAP. These treatments may be used on any animal which is susceptible to infection by MAP.

The subject to be treated may be any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly. If a mammal, the subject will preferably be a human, but may also be a domestic livestock, laboratory subject or pet animal.

The subject to be treated may thus be any vertebrate that is susceptible to infection by MAP. Numerous animals have been shown in the art to be capable of such infection, including livestock such as cattle, goat and sheep, primates such as macaques and humans, other mammals including alpaca, antelope, ass, elk, horses, deer, dogs, gerbils and rabbits, and birds including the chicken. The compositions of the present invention may thus be used in the treatment of any such species.

Combined Therapy

In one embodiment, the method of treating or preventing MAP infection or a condition associated with MAP infection may comprise administering a further therapeutic agent which has activity against MAP or a further therapeutic agent used in the treatment of a condition which is associated with MAP infection to the subject.

The further therapeutic agent may be another polynucleotide, vector or polypeptide, for example, one or more antimicrobial agent, such as a combination including Rifabutin and Clarithromycin, is administered to the patient, either alone or in combination with one or more additional therapeutic agents. The treatment may be a prophylactic or therapeutic MAP vaccine. The treatment may comprise passive immunotherapy administering to the subject anti-MAP monoclonal antibodies such as the antibodies and peptides described herein.

The therapeutic agent may be, for example an agent which has activity against MAP, or an agent used in the treatment of a condition which is associated with MAP infection. The vaccine, peptide, polypeptide, polynucleotide or vaccine vector of the invention is preferably administered in an amount which is sufficient to augment the anti-MAP effects of the other therapeutic agent or vice versa. Numerous other agents may be used in the treatment of MAP or conditions which are associated with MAP infection. These include the rifamycins such as rifabutin and rifaximin, clarithromycin and other macrolides, azathioprine, methotrexate, Humira, 6-mercaptopurine and/or Infliximab. Various anti-tuberculosis drugs may also be used.

The other therapeutic agent may be an agent which potentiates the effects of the molecule of the vaccine, peptide, polypeptide, polynucleotide or vaccine vector the invention. For example, the other agent may be an immunomodulatory molecule or an adjuvant which enhances the immune response to the polypeptide. Alternatively, the other molecule may increase the susceptibility of MAP present in the subject to attack, such as attack from the immune system.

In one embodiment, therefore, the vaccine, peptide, polypeptide, polynucleotide or vaccine vector of the invention is used for therapy in combination with one or more other therapeutic agents.

The vaccine, peptide, polypeptide, polynucleotide or vaccine vector may be administered separately, simultaneously or sequentially. The vaccine, peptide, polypeptide, polynucleotide or vaccine vector may be administered in the same or different compositions. Accordingly, in a method of the invention, the subject may also be treated with a further therapeutic agent.

A composition may therefore be formulated which comprises the vaccine, peptide, polypeptide, polynucleotide or vaccine vector of the invention and also one or more other therapeutic molecules. For example, a vector of the invention may be formulated with another vector which encodes one or more other antigens or therapeutic molecules. The vaccine, peptide, polypeptide, polynucleotide or vaccine vector of the invention may alternatively be formulated with one or more therapeutic proteins.

The present invention also encompasses the use of a vaccine, peptide, polypeptide, polynucleotide or vaccine vector according to the invention in combination with an additional therapeutic agent in the manufacture of a medicament for treating or preventing MAP infection or a condition or symptom associated with MAP infection.

Delivery Methods

Once formulated the vaccine compositions can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, and active or passive transdermal delivery techniques. Particularly in relation to the present invention, compositions may be administered directly to the gastrointestinal tract.

Alternatively, the compositions can be administered ex vivo, for example delivery and reimplantation of transformed cells into a subject are known (e.g., dextran-mediated transfection, calcium phosphate precipitation, electroporation, and direct microinjection into nuclei).

Delivery Regimes

The compositions are administered to a subject in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed.

As used herein, the term "prophylactically or therapeutically effective dose" means a dose in an amount sufficient to elicit an immune response to one or more epitopes of a polypeptide of the invention and/or to alleviate, reduce, cure or at least partially arrest symptoms and/or complications from a disease, such as an inflammatory bowel disorder, which is associated with a MAP infection.

Prophylaxis or therapy can be accomplished by a single direct administration at a single time point or by multiple administrations, optionally at multiple time points. Administration can also be delivered to a single or to multiple sites. Those skilled in the art can adjust the dosage and concentration to suit the particular route of delivery. In one embodiment, a single dose is administered on a single occasion. In an alternative embodiment, a number of doses are administered to a subject on the same occasion but, for example, at different sites. In a further embodiment, multiple doses are administered on multiple occasions. Such multiple doses may be administered in batches, i.e. with multiple administrations at different sites on the same occasion, or may be administered individually, with one administration on each of multiple occasions (optionally at multiple sites). Any combination of such administration regimes may be used.

In one embodiment, different compositions of the invention may be administered at different sites or on different occasions as part of the same treatment regime. It is known that improved immune responses may be generated to an antigen by varying the vectors used to deliver the antigen. There is evidence that in some instances antibody and/or cellular immune responses may be improved by using two different vectors administered sequentially as a "prime" and a "boost".

For example, the same peptide, polypeptide, or polynucleotide of the invention may be administered as a "prime" in one composition, and then subsequently administered as a "boost" in a different composition. The two vaccine compositions used for the "prime" and "boost" may differ. For example, they may differ in the choice of vector comprising the polynucleotide. For example, two or more of different vectors each selected from plasmid vectors, poxvirus vectors, adenovirus vectors or other vectors as described herein may be administered sequentially.

In one embodiment, a "prime" is effected by administering a polynucleotide of the invention in a plasmid vector such as pSG2. A "boost" is then effected at a later time using a polynucleotide of the invention in a poxvirus vector such as MVA.

In an alternative embodiment a "prime" is effected by administering a polynucleotide of the invention in an adenovirus vector such as Ad5. A "boost" is then effected at a later time using a polynucleotide of the invention in a poxvirus vector such as MVA.

The vaccine composition used for the "prime" may differ from the vaccine composition used for the "boost" in that one composition may comprise a peptide or polypeptide and the other composition may comprise a polynucleotide. For example, in one embodiment, the "prime" may be effected by administering a peptide or polypeptide and the "boost" may be effected by using a polynucleotide. As a specific example of this, the "prime" may comprise administering a peptide or polypeptide, for example a peptide comprising, consisting essentially of or consisting of the sequence shown in any one of SEQ ID NOs: 3 to 6, and the "boost" may be effected by administering a polynucleotide comprising an N-terminal fragment of P900, such as a polynucleotide comprising an N-terminal fragment of P900 and one or more of an ahpC polypeptide, a gsd polypeptide, a p12 polypeptide and a MPA polypeptide. The polypeptide may have one of the specific sequences shown in SEQ ID NO: 41 and SEQ ID NO: 42, in which the MAP P900 N-terminal fragment is inserted at the junction between the aphC, and gsd polypeptides, between the gsd and p12 polypeptides, between the p12 and mpa polypeptides, before the aphC polypeptide and/or after the mpa polypeptide. It is envisaged that such an immunisation protocol may be particularly beneficial in immunising livestock, such as cattle or sheep, particularly where a phosphorylated form of the MAP P900 N-terminal fragment is used, such as a peptide comprising, consisting of, or consisting essentially of the amino acid sequence shown in SEQ ID NO: 4 or 6.

In such a prime-boost protocol, one or more administrations of the prime and/or the boost may be performed. For example, the prime and/or boost step may be achieved using a single administration or using two or more administrations at different sites and/or on different occasions. In one embodiment, two administrations on different occasions are given for the prime step and a single administration on a later occasion is given for the boost step.

Different administrations may be performed on the same occasion, on the same day, one, two, three, four, five or six days apart, one, two, three, four or more weeks apart. Preferably, administrations are 1 to 5 weeks apart, more preferably 2 to 4 weeks apart, such as 2 weeks, 3 weeks or 4 weeks apart. The schedule and timing of such multiple administrations can be optimised for a particular composition or compositions by one of skill in the art by routine trials.

Dosages for administration will depend upon a number of factors including the nature of the composition, the route of administration and the schedule and timing of the administration regime. Suitable doses of a molecule of the invention may be in the order of up to 15 µg, up to 20 µg, up to 25 µg, up to 30 µg, up to 50 µg, up to 100 µg, up to 500 µg or more per administration. For some molecules of the invention, such as plasmids, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route. In the case of a viral vector, a dose of about $10^6$, $10^7$, $10^8$, $10^9$, $10^{10}$ or more pfu may be given per administration. For example, a dose of $10^9$ pfu or 25 µg of a vector of the invention may be administered in a 50 µl dose at multiple sites and/or on multiple occasions.

Kits

The invention also relates to a combination of components described herein suitable for use in a treatment of the invention which are packaged in the form of a kit in a container. Such kits may comprise a series of components to allow for a treatment of the invention. For example, a kit may comprise two or more different vectors of the invention, or one or more vectors of the invention and one or more additional therapeutic agents suitable for simultaneous administration, or for sequential or separate administration such as using a prime and boost protocol. The kit may optionally contain other suitable reagent(s), control(s) or instructions and the like.

EXAMPLES

Example 1: Efficacy of hAd5 HAV Prime and MVA HAV Boost Vaccination in Bovine Calves A BBSRC-funded trial of HAV vaccination in protection against experimental MAP infection was carried out (2010-2014) by St George's University of London, The Jenner Institute University of Oxford, The Roslin Institute University of Edinburgh, Animal Health and Welfare and the Agri-Food and Biosciences Institute of Northern Ireland.

The amino acid sequence of the HAV vaccine insert with leader peptide and PK tail at either end in bold is shown below. The sequences from its four MAP genes 1589c (AhpC), 1234 (Gsd), 2444c (p12) and 1235 (mpa) which have been described above, comprise the peptide sequences in between. The junctions between the HAV vaccine components are marked *.

MQIFVKL*PLLTIGDQFPAYELTALIAGDLSKVDAKQPGDYFTTVTSEDHAGKWRVVFFWPKDFTGPEIAT
FGKLNDEFEDRDAQVLGVSIDSEFVHFNWRAQHEDLKNLPFPMLSDIKRELSLATGVLNADGVADRATFI

VDPNNEIQFVSVTAGSVGRNVEEVLRVLDALQSDELCACNWRKGDPTLNATELLKASAL*GSIVGQTYREV

EVVLVDGGSTDRTLDIANSFRPELGSRLVVHSGPDDGPYDAMNRGVGVATGEWVLFLGADDTLYEPTTLA

QVAAFLGDHAASHLVYGDVVMRSTKSRHAGPFDLDRLLFETNLCHQSIFYRRELFDGIGPYNLRYRVWAD

WDFNIRCFSNPALITRYMDVVISEYNDMTGFSMRQGTDKEFRKRLPMYFWVAGWETCRRMLAFLKDKENR
RLALRTRLIRVKAVSKERSAEP*RIRRHRHAEIILSMPGFGVILGAEFLAATGGDMAAFASADRLAGVAGL
APVPRDSGRISGNLKRPRRYDRRLLRACYLSALVSIRTDPSSRTYYDRKRTEGKRHTQAVLALARRRLNV

LWAMLRDHAVYHPATTTAAARL*KLRRGERPMSLGQVFDPRANALHSFPLTGRMPWAPFIVSSWLRNPHPA

QYFTARCLRILPGLWIGAQGGSAAKLLMSGAPIEYVLKDSAVWMFKFDIGGTPRDIPVAGIWNGSLWTPA

WGGIHAIASNAYQFRNVIPARWSVSSAVLPNYRLVAALPMAYHNQRMRFRTDLSYGVYGFAEINPIALVE

KPALSWKSRLRRKNSSIALANMEDGGSVGRSNDIPGRRARFIGEKAEDPPAPSPR*PALRIPNPLLGLD

The underlined sequence is that of p12, the carboxyterminal region of the P900 protein encoded by the positive strand of the IS900 element. The p12 portion within HAV has a short cytoplasmic domain followed by the highlighted predicted transmembrane-like sequence, followed by the remaining extracellular portion of the P900 protein. The extracellular carboxyterminal portion of P900 is exported by the MAP cell and further cleaved by limited proteolysis to traffic between host cells in exosome like vesicles. The IS900 derived component of the HAV vaccine has the highest level of cellular immunogenicity of the 4 HAV vaccine components.

Six Holstein Friesian calves were given the priming dose of $10^9$ viral particles (vp) of hAd5 HAV (the AhpC, gsd, p12 and mpa antigen expressing adenovirus vaccine described in WO 2007/017635) in 1 mL sterile PBS by intradermal injection (id) into the skin of the neck. Five control calves were given the same dose of hAd5 expressing Green Fluorescent Protein (GFP). At 6 weeks calves in the test group received the boosting dose of $10^9$ plaque forming units (pfu) of MVA HAV in 1 mL sterile PBS id. Control calves received the same id dose of MVA GFP.

At 12 weeks all animals received $5\times10^8$ live virulent MAP strain R0808 given orally in 20 ml PBS on 2 consecutive days. They were then followed for 38 weeks. No adverse effects of vaccination or inflammatory disease over the period of the study were seen in any of the animals. Blood and faecal samples were obtained before and after each prime and boost vaccination and MAP challenge. Observations were continued with monthly blood and faecal sampling for a period of 38 weeks at the end of which the animals were euthanized.

Shortly after oral MAP challenge all animals in the control group shed MAP in their faeces and continued throughout the study. In all test animals HAV vaccination prevented detectable faecal shedding of MAP throughout the study. All six calves in the test group responded with an increased PBMC release of IFN-γ following PPD-J stimulation not seen in the control group. This was accompanied by a rise in the percentage of CD4+IFN-γ+ and CD8+IFN-γ+ secreting cells which was absent from the control group. Specific cellular immune responses to HAV vaccine peptides were seen in all HAV vaccinated but not in control animals two weeks after boosting and were maintained throughout the study.

Immediately prior to the oral administration of MAP, laboratory tests of the ability of PBMC from control calves to kill MAP were the same as those of PBMC from HAV vaccinated calves. Within 1 week of challenge the in vitro MAP killing capacity of PBMC from control calves dropped dramatically by 30% but was unchanged in HAV vaccinated calves. At the same time circulating PBMC from 5/6 HAV vaccinated and 4/5 control calves tested PCR positive for MAP.

A significant impairment of the in vitro capacity of PBMC from control calves to kill MAP remained and by week 14 the proportion of these animals with MAP positive PBMC in their blood remained at 4/5. At the same time MAP positive PBMC in blood of vaccinated calves had fallen to 2/6. These trends in blood continued so that over the 19 week second half of the study following MAP infection 3/5 control animals became consistently MAP positive and the other 2 intermittently positive. By contrast PBMC from 4/6 HAV vaccinated calves remained consistently MAP negative. Each of the other 2 animals had only 1 of 5 MAP PCR tests positive over the last 19 week period of observation. ELISpot responses of PBMCs to stimulation with HAV specific peptide antigens which were absent from the control group of animals, continued throughout the study in all vaccinated animals.

At autopsy, full thickness tissue samples were taken from 11 sites throughout the length of the small intestine comprising 2 from the duodenum, 6 from the jejunum and 3 from the ileum together with 4 mesenteric lymph nodes (MLN) and tissue from the spleen. MAP loads in tissues at autopsy were measured by specific qPCR. In the 5 control calves all tissue samples were positive for MAP with microbial loads of up to 5 logs per gram of sample. As a group these tissue samples comprised totals of 10 from the duodenum, 30 from the jejunum, 15 from the ileum, 20 from mesenteric lymph nodes (MLN) and 1 sample each for the 5 spleens.

By contrast, in the 6 HAV vaccinated calves 10 of 12 tissue samples from the duodenum, 28 of 36 from the jejunum, 12 of 18 from the ileum, 7 of 24 from MLN and 3 of the 6 spleens tested negative for MAP. In the residual MAP positive samples, HAV vaccination was associated microbial loads substantially lower than corresponding samples in the control group. As with other chronic enteric human pathogens such as Tuberculosis, *Yersinia, Legionella* and others, MAP demonstrates an ability to persist in MLN for which further strategies may be devised.

This study was necessarily designed to test the ability of HAV vaccination in a protective role against MAP infection in bovine calves. Both the control and HAV Vaccinated group of calves became MAP positive in blood after MAP challenge. All control calves remained MAP positive in blood and shed MAP in their faeces throughout the study. All HAV vaccinated calves appeared to eliminate MAP from blood and blocked detectible faecal shedding.

Example 2: Phases of Development of MAP Antibodies

Phase 1. Mapping Mouse Antibody Binding Peptide Domains in P900

IS900 (NCBI accession: AE016958.1) is a DNA insertion element of 1451-53 bp discovered by the present inventor and colleagues late in 1985 in three Crohn's disease isolates of MAP (E. Green et al Nucleic Acids Research 1989; 17: 9063-73). It is present in MAP in 14-18 identical copies inserted at highly conserved sites throughout the MAP genome. This multicopy element has its own promoter, is abundantly expressed in humans and contributes to the broad pathogenic phenotype.

The positive strand of IS900 predicts a protein (P900) of 406 amino acids. Its full length amino acid sequence is unique to MAP but there are P900 'look-alikes' in closely related mycobacteria and actinomycetes which cover most of the P900 molecule.

Full length P900 protein encoded by the positive strand of IS900 is toxic for *E. coli* cells. A less toxic truncated version consisting of amino acids 49 to 377 of P900 was made and expressed as the recombinant protein in *E. coli*.

Ten mice were immunised with the recombinant truncated P900 protein adherent to magnetic beads because the free recombinant protein was found not induce a satisfactory immune response. The sera from immunised mice were screened by ELISA against immobilised P900 and 4 positive mice were identified. Spleen cells from these mice were used for hybridoma fusion resulting in 10 parental clones. Supernatants from these and their successive subclones were screened against a library of 64 synthetic 15 amino acid peptides overlapping by 10 amino acids spanning the truncated P900 amino acid sequence from ELIAAVTTLADG-GEV . . . to . . . DRKRTEGKRHTQAVL. The antibodies were all IgM and the clones eventually proved unstable. Despite the inability to obtain the desired monoclonal reagents, 8 peptides or peptide clusters were identified as immunogenic within the truncated P900 protein. In the peptide library these involved peptides No. 2-VTTLADG-GEVTWAID, 27-NKSRAALILLTGYQT, 41-AKEV-MALDTEIGDTD, 42-ALDTEIGDTDAMIEE and a cluster within the sequence GRISGNLKRPRRYDRRLLRACYL-SALVSIRTDPSSRTYYD.

Phase 2. Preparation of Polyclonal Antibodies to P900 Sequences in Rabbits and their Testing on Humans and Animals.

Polyclonal Antibody Preparation

Initial peptides designated A1-VTTLADGGEVTWAID-LNA, A2-NKSRAALILLTGYQTPDA, A3-NLKRPRRY-DRRLLRAGYL, and A4-YLSALVSIRTDPSSR were identified. These were prepared as synthetic branched octapeptide immunogens on polylysine cores and used to immunise rabbits. Suitable titres of polyclonal antibodies were readily achieved for A1, A3, and A4. A2 was not immunogenic the rabbit. A2 was also intracellular in MAP and was not studied further.

Antibodies in A1 and A3 sera reacting with Freund's complete adjuvant (*M tuberculosis* H37Ra, Difco, USA) were abstracted to completion using excess antigen. Only Freund's incomplete antigen was used as the adjuvant with A4. Rabbit polyclonal reagents A1, A3 and A4 were applied in preliminary studies to explore their ability to detect their target sequences and therefore MAP immunoreactivity in human and animal tissues and human blood.

MAP Immunoreactivity in Human Tissues

In an initial study, fresh intestinal mucosal biopsies were obtained from 14 patients diagnosed with Crohn's disease (CD) attending the endoscopy clinic at St Thomas' Hospital, London, UK and 10 control patients without inflammatory bowel disease (nIBD) attending for screening or follow up. Ethical approval was given by the Local Ethics Committee (EC03/053). Biopsies were embedded in Jung tissue freezing medium and snap frozen in liquid nitrogen in the endoscopy suite. They were then taken to the laboratory where they were coded and stored −80° C. prior to use.

Orientated biopsies were subsequently cut in 6 μm sections and mounted on PTFE coated slides and stained with A1, A3 and A4 polyclonal antibodies at a dilution of 1:400 to 1:800. Host cell phenotypic markers were CD3 for T cells, CD8 for monocytes/macrophages, CD19 for B cells, CD66b for neutrophils, CD83 for Dendritic cells, PgP9.5 for Glial cells and CD31 for endothelium. Secondary antibodies were rabbit anti-mouse TRITC (R0270 Dako, UK), rabbit anti-mouse FITC (F0261, Dako), swine anti-rabblt TRITC (R0156, Dako), swine anti-rabbit FITC (F0205, Dako) and goat anti-mouse FITC (F0479). Slides were washed x3 in PBS and mounted in Fluoromount agent (F4680 Sigma-Aldrich, UK) followed by a coverslip.

Use of antibodies A1, A3 and A4 alone at concentrations of 1:500 to 1:800 resulted in staining of cells within the epithelium and in the underlying lamina propria. Antibodies were then used in pairs with A1 labelled with TRITC (red) and A3 or A4 with FITC (green).

The A1 site is located on the extracellular aminoterminal domain of the P900 protein adjacent to the first transmembrane region and right up against the surface of the microbial cell. The A1 peptide appeared to remain attached to MAP.

The A3 and A4 sites are located at the centre of the longer carboxyterminal extracellular domain either side of Cysteine 344. The carboxyterminal domain may either be attached or released by limited proteolytic cleavage close to the second transmembrane region.

Use of A1 (red) and A4 (green) with the carboxyterminal peptide still attached resulted in colocalisation (gold) not only in the same cells but also on submicrometre particles within the cytoplasm of infected cells. Release of the carboxyterminus resulted in a progressive gradient of colour change from gold to orange to red and the visible migration of the released peptide (green) in the cytoplasm of the affected cell. Other cells were seen to contain green only suggesting the ability of released carboxyterminal peptide to traffic to other cells which did not themselves contain MAP. This was supported by the appearance in tissues of intercellular vesicles filled green consistent with endosomes.

In the surface epithelium MAP was seen to infect enterocytes as well as intra-epithelial cells consistent with lymphocytes and macrophages. MAP was seen to cluster often in a 'necklace' around the base of the mucus vacuole of goblet cells releasing green carboxyterminal peptides which migrated in the cytoplasm to the apex of these cells as well as within the mucus vacuole itself.

MAP was also seen to infect cells widely in the lamina propria and particularly clusters of cells around the bases of crypts. Staining involved particularly macrophages, polymorphs and B-lymphocytes but not T-lymphocytes although the presence of T-lymphocytes adjacent to MAP clusters was frequently noted.

Abundant MAP infection in endoscopic mucosal biopsies was seen in all 14 patients with Crohn's disease. Scant clusters of immunoreactive MAP were seen in 8 out of the 10 control subjects. The other 2 control subjects contained no MAP staining at all. The addition of specific peptide to the operational buffer completely blocked staining of tissues by the corresponding antibody. Use of other peptides had no effect on antibody binding. Together with colocalisation this specific blockade reinforced the precision and specificity of the MAP detection system.

PCR Verification of A1 Antibody Binding to MAP in Human Tissues:

Lasermicrodissection pressure catapulting (LMPC) of A1 immunoreactive loci was carried out to determine whether antibody recognition in tissues equated with the presence of MAP using IS900 PCR. Fresh endoscopic mucosal biopsies were obtained from 11 consenting patients and 4 control subjects without inflammatory bowel disease. Tissues were snap frozen in liquid nitrogen and 6 µm cryostat sections were cut as previously described. Sections were transferred to PTFE-coated microscope slides for routine H&E staining. Those for LMPC were immobilised on PEN-membrane slides (Carl Zeiss MicroImaging GmbH, Germany).

Immunoreactive MAP regions were identified in sections with A1 rabbit polyclonal antibody using biotinylated alkaline phosphatase H tagged $2^{nd}$ antibody to rabbit immunoglobulin. After washing slides in PBS, Vectastain Universal ABC-AP kit (Vector Laboratories UK) was used for localisation of immunoreactive MAP regions according to the manufacturer's instructions. Secondary antibodies were localised using the Vector Blue Alkaline Phosphatase Substrate Kit 1 (Vector Laboratories UK).

Lasermicrodissection and pressure catapulting was used to isolate immunoreactive (IR) and non-immunoreactive (nIR) MAP regions using the Zeiss PALM MicroBeam Laser microdissection system. Prior to microdissection, particular care was taken to ensure that sections were completely air dried so that excised regions readily detached. IR and nIR regions were identified visually and the adhesive cap tube positioned above the selected area. Samples were accumulated onto the cap of the adhesive tube. DNA extraction was carried out as described (T. Bull et al. 2003 J Clin Microbiol 2003; 41:2915-23). Briefly, 200 µL of *Mycobacterium* Lysis Buffer (MLB), 8.6 ml molecular-grade water, 800 µL 5M NaCl, 1M 10× Tris-EDTA (TE) and 600 µL 10% SDS was added to each tube and incubated overnight at 37 deg C. 10 µL of 10 mg/ml Proteinase K (Sigma), 5 µL of 100 mg/ml Lysozyme (Sigma) and 4 µL of 120 mg/ml Lipase (Sigma) in MLB were added to each tube and incubated at 37° C. for a further 3 hours. Samples were transferred to Lysing Matrix B ribolyser tubes and 400 µL 1×TE added. Tubes were mechanically disrupted at 6.5 $ms^2$ for 45 seconds on a FastPrep Ribolyser instrument. Standard phenol-chloroform-isoamyl DNA extraction procedure was carried out. Purified DNA was resuspended in 50 µL 1×TE. Nested PCR using 2 µL of template DNA was carried out using L1 and L2 first round primers and AV1 and AV2 second round primers. The expected 298 bp PCR amplicon was visualised using 1% agarose gel electrophoresis. Stringent precautions were taken as described to exclude amplicon contamination.

All 4 control subjects tested negative by IS900 PCR. Immunoreactive regions from 7 of the 11 patients in the CD group were positive for MAP by IS900 PCR, confirmed by amplicon sequencing in 5. All the nIR regions sampled in CD patients were PCR negative. All 7 patients testing positive for MAP by IS900 PCR were undergoing treatment with azathioprine alone. The 4 PCR negative samples came from Crohn's disease patients receiving treatment with azathioprine in combination with Humira or 6-mercaptopurine and Infliximab.

Phase 3. Preparation of Murine Monoclonal Antibodies to Optimised P900 Peptide Sequences within the Selected A0, A1, A3 and A4 Sites and Phosphorylated Derivatives.

At this stage, an additional target site for monoclonal antibody production designated A0 was introduced comprising the sequence MVINDDAQRL, residues 26-39 in the extracellular aminoterminal domain of P900. Few identical matches to this sequence were found in NCBI databases.

The production of murine monoclonal antibodies was first attempted in the following manner. Immunogen peptides in each case incorporating a solitary Cys thiol for linkage to KLH were prepared for A0 (MVINDDAQRL-C), A3 (C-NLKRPRRYDR) and A4 (C-VSIRTDPSSR) and 5 mice were immunized in each group. Despite good immunological responses in some of the mice in each group, no monoclonals recognising their native targets in tissues were obtained. This was found to be due to the exclusive use of the target peptide for screening ELISAs and clonal selection being coated directly on to ELISA plate wells. This resulted in substantial artifact and the project was a comprehensive failure.

On the other hand the inventor found that it was essential for the target synthetic peptides used in screening ELISAs to be alpha-n Biotinylated and attached to wells coated with streptavidin. This increased the steric accessibility of the attached mobile peptides and permitted the adoption of the appropriate configuration of the peptide for antibody in the liquid phase. There was close correlation between antibody binding to target peptide in this form in ELISAs and to the native peptide in target tissues.

The essential Streptavidin coating and Biotinyl-peptide immobilisation in ELISA wells was adopted and used throughout the next project. During this project, mouse sera and culture supernatants were selected for binding to Reference peptide but not Negative peptides. Selected samples were subsequently tested by immunofluorescence on human and animal tissues and cells infected with MAP.

Immunogens were synthesised using the peptide sequences A0X MVINDDAQRLLSQR-C, A1 VTTLADG-GEVTWAID-C, and XA4 YLSALVSIRTDPSSR-C in each case the Cys thiol was used to link to KLH using standard methods. These constructs were used to immunise groups of 5 to 10 BalbC mice. Good serological responses to immunisation occurred in all groups and promising candidate clones were obtained for each group. Despite additions to immunisation protocols including in vitro immunisation and follow on immunisation using different immunogen adducts together with much additional work, no suitable final stable IgG clones could be obtained.

The materials used initially in the next project were as follows:

| Immunogen Peptide | A0 ac-MVINDDAQRL-8branchedPolylysineOctamer |
|---|---|
| Reference peptide | Biotinyl-MVINDDAQRL-amide |
| Negative peptide 1 | Biotinyl-MVINDDLQR-amide |
| Negative peptide 2 | Biotinyl-MVINNDAE-amide |
| Immunogen peptide | A1 ac-VTTLADGGEVT-8branchedPolylysineOctamer |
| Reference peptide | Biotinyl-VTTLADGGEVT-amide |
| Negative peptide 1 | Biotinyl-VATMADGGEVT-amide |
| Negative peptide 2 | Biotinyl-VTRLADGGEVT-amide |
| Immunogen peptide | A3 ac-NLKRPRRYDR-8branchedPolylysineOctamer |
| Reference peptide | Biotinyl-NLKRPRRYDR-amide |
| Negative peptide 1 | Biotinyl-NLKRPRR-amide |
| Negative peptide 2 | Biotinyl-NLRRPRRYHR-amide |
| Negative peptide 3 | Biotinyl-NLHRPRRYHR-amide |
| Negative peptide 4 | Biotinyl-NMRRPRRYNR-amide |
| Negative peptide 5 | Biotinyl-NLRRPKRYNR-amide |
| Negative peptide 6 | Biotinyl-NLQRPRRYNR-amide |
| Immunogen peptide | A4 ac-VSIRTDPSSR-8branchedPolylysineOctamer |
| Reference peptide | Biotinyl-VSIRTDPSSR-amide |
| Negative peptide 1 | Biotinyl-VSIRTDP-amide |
| Negative peptide 2 | Biotinyl-SIRSDPSSR-amide |
| Negative peptide 3 | Biotinyl-YSIRSDPASR-amide |
| Negative peptide 4 | Biotinyl-VSVRYDPSSR-amide |
| Negative peptide 5 | Biotinyl-IAIRTDPASR-amide |

Groups of 5 Swiss Webster mice were immunised with the immunogen peptide constructs in Freund's Complete Antigen on day 1 followed by 2 booster shots on day 14 and day 21 using Freund's Incomplete antigen. Boosting was continued but it was clear that none of the 4 groups were responding satisfactorily. Fresh peptide immunogens ac-MVINDDAQRL-C, ac-VTTLADGGEVT-C, ac-NLKRPR-RYDR-C, and ac-VSIRTDPSSR-C were synthesised, coupled via the C- to KLH and immunisations continued.

Transient responses in the A0 and A1 groups were not sustained. Both flatlined and were terminated.

Serum from one mouse in each of the A3 and A4 groups achieved a sufficient titre to proceed to fusion and development of parental clones. A satisfactory subclone was not subsequently obtained for A3 and this project was terminated. A satisfactory subclone was achieved for A4 which recognised the reference peptide and none of the 5 negative peptides and was taken through final production and Protein A affinity purification.

At this stage three further modifications were introduced into the protocol:
1. The use of Balb/C mice.
2. Adoption of the technique of administering the immunogen at the base of the tail vein followed by direct fusion of pooled cells from inguinal lymph nodes.
3. Redesigned projects with the following new peptide immunogens.

| Immunogen peptide | A0X C-MVINDDAQRLLSQR-amide |
|---|---|
| Reference peptide | Biotinyl-MVINDDAQRLLSQR-amide |
| Negative peptide 1 | Biotinyl-MVINDDLQRIILFL-amide |
| Negative peptide 2 | Biotinyl-MSINDDAQKLKDRL-amide |
| Immunogen peptide | A0XP C-MVINDDAQRLL[pS]QR-amide BSA conjugated |
| Reference peptide | Biotinyl-MVINDDAQRLL[pS]QR-amide |
| Negative peptide 1 | Biotinyl-MVINDDAQRLLSQR-amide |
| Immunogen peptide | XA1 ac-AAVTTLADGGEVTWAIDGKK-C BSA conjugated |
| Reference peptide | Biotinyl-KKGAAVTTLADGGEVTWAID-amide |
| Negative peptide 1 | Biotinyl-KKGAAGTTLADGGEVTWAID-amide |
| Negative peptide 2 | Biotinyl-KKGSTVATMADGGEVTWAID-amide |
| Negative peptide 3 | Biotinyl-KKGQAVTRLADGGEVTWAVD-amide |
| Negative peptide 4 | Biotinyl-KKGFEVTTLADGTEVATSPL-amide |

The addition of the two Alanine residues to the amino terminus at this site was designed to increase immunogenicity and specificity. The addition of the charged –GKK residues at the carboxyterminus of the immunogen peptide was designed to overcome its increased hydrophobicity. In the event that the immunogen peptide formed micelles during the coupling reaction the presence of the charged GKK moiety adjacent to the Cysteine thiol would favour its accessibility to the BSA. The inclusion of mirror image KKG—at the aminoterminus of the reference peptide would favour the selection of antibody specific for the target sequence itself.

| Immunogen peptide | XA4P C-YLSALVSIRTDPS[pS]R-amide BSA conjugated |
|---|---|
| Reference peptide | Biotinyl-YLSALVSIRTDPS[pS]R-amide |
| Negative peptide 1 | Biotinyl-YLSALVSIRTDPSSR-amide |
| Negative peptide 2 | Biotinyl-YLSALYSIRSDPA[pS]R-amide |
| Negative peptide 3 | Biotinyl-YLSALVSVRYDPS[pS]R-amide |
| Negative peptide 4 | Biotinyl-YLSAQIAIRTDPA[pS]R-amide |

All five A0X, A0XP, XA1, A4 and XA4P projects incorporating clonal selection for Reference peptide recognition by ELISA with limited or no binding to Negative Control peptides, followed by tissue and cell staining by selected clonal supernatants binding to tissues and cells, have been brought to successful conclusions. Affinity purified A0X, A0XP, XA1, A4 and XA4P monoclonals were obtained.

Example 3: Uses of the Diagnostic Technology for the Detection and Characterisation of MAP Infections in Samples from Humans and Animals and in Food Safety 1. Detection and Measurement of MAP Infecting Human Gut Tissues Endoscopic biopsies were studied from 45 people with Crohn's disease and some other disorders such as Irritable Bowel Syndrome (Scanu et al. *Mycobacterium avium* subspecies paratuberculosis infection in cases of Irritable Bowel Syndrome and comparison with Crohn's disease and Johne's disease: common neural and immune pathogenicities. J Clin Microbiol 2007: 45:3883-90). Samples were immediately fixed in formalin, followed by standard processing and embedding in paraffin Histopathology blocks. Preliminary work was carried out which identified 2 μm sections as optimal. Sections were treated with a standard antigen retrieval protocol. They were then stained with dilutions of monoclonal antibodies in the range 1 in 500 to 1 in 5000. Both direct fluorophore labelling of primary antibodies as well as the use of secondary antibodies labelled with fluorophore were employed. Tissues were stained with each of the primary antibodies A0X, A0XP, XA1, A4, XA4P used alone and viewed with using a Zeiss AxioSkop 2 microscope at magnifications of ×100 and ×200 to obtain a general impression of the distribution of MAP and then subsequently at ×400 and ×1000. MAP in humans is a Ziehl-Neelsen (Z-N) staining negative form and appears to be in the size range 0.3-1 μm. Higher magnification is required for satisfactory resolution.

A0X, XA1, A4 and XA4P all stained MAP in human gut, more specifically in endoscopic biopsies of the gut in all of the 45 people with Crohn's disease tested. However, staining of human gut tissues by A0XP was not seen in humans other than the occasional fluorescent signal from the lumen of a tissue blood vessel containing an A0XP positive cell in the blood. Unlike in animals, phosphorylation of A0X does not appear to occur widely in human gut. Phosphorylated A0XP however is seen in human blood in MAP infections. Staining of MAP by A0X, A0XP, XA1, A4 and XA4P is seen in human blood in MAP infection and in all people with Crohn's disease tested.

Antibodies were also used in combinations and viewed by confocal microscopy. Preferably antibodies were used in pairs. Preferred pairs were A0X with A0XP or XA1 from the amino terminus of the parent MAP molecule, and A4 with XA4P from the carboxyterminal end. Preferred pairs were also A0X with A4 and XA1 with A4 labelled with a red or green fluorophore respectively. This provided gold staining when the reagents colocalised specifically in the cytoplasm, not only of the same cells, but on the sub-micrometre MAP particles within the cytoplasm of infected cells. Such colocalisation provided strong confirmation of the specificity of MAP detection.

The use of antibody pairs comprising XA1 with A4 and A0X with A4 revealed a further aspect of the method. This is because whereas A0X and XA1 appeared to remain attached to the MAP organism itself or released to remain in the cell or displayed on the cell surface, A4 is frequently released from MAP to become displayed on the cell surface as well as released from the infected cell to traffic between cells. When A0X or XA1 are labelled with a red fluorophore and A4 labelled with a green one, the original gold colocalisation is progressively depleted to orange, and then to red as the green labelled A4 traffics to and enters other cells. Membrane bound structures filled with A4 green were seen, consistent with the presence of intercellular vesicles.

Biopsy samples from all the patients with Crohn's disease tested positive for MAP. This was observed in cells of the mucosal compartment, particularly the basal portion of the epithelial cells and the cytoplasm surrounding the basal portion of the mucus in goblet cells. Other MAP containing cells in the mucosal compartment were intra-epithelial macrophages and dendritic cells as well as intra-epithelial lymphocytes. MAP containing cells and free bacilli were also observed in the luminal mucus gel layer. In the lamina propria MAP infection was common in macrophages, polymorphs and B-lymphocytes. T-lymphocytes were rarely seen to be involved themselves, but frequently occurred adjacent to MAP filled macrophages. MAP positive cells were frequently seen in the lumen of small blood vessels. In duodenal biopsies MAP staining of Brunner's glands was limited only to the occasional macrophage filled with MAP while the glandular cells themselves were unaffected. However MAP containing cells were present in the interstitial connective tissue of Brunner's glands. A0XP in cells within tissues appeared to concentrate around the nucleus. These images of MAP in human tissues can be adapted to become quantitative and enable monitoring of the MAP infective load.

Surgical resection samples were also available from 4 patients with Crohn's disease. These samples permitted the examination not only the deeper layers of the gut through to the serosa, but also larger blood vessels, lymphatic vessels, extra intestinal fat wrapping and regional lymph nodes in the gut mesentery. As with the biopsy tissues the mucosa and sub-mucosa of each of these 4 patients were strongly positive for MAP. It was also found that the MAP infection extended right through the wall of the gut involving lymphatic vessels, the tissue between muscle layers and the serosa itself. In some sections lymphatic vessels full of stained MAP organisms were seen.

It has long been known that one of the pathological features of Crohn's disease is a vasculitis deemed to be autoimmune. The diagnostic antibodies showed that the thickened walls of such blood vessels were extensively infiltrated with MAP which also involved the surrounding perivascular connective tissues. Another characteristic pathological feature of Crohn's disease is the increase in fatty tissue around the gut. This is particularly well seen in the terminal ileum where it is termed 'fat wrapping'. The adipocytes of this fat are known to be a rich source of the inflammatory marker CRP (C-reactive protein). The diagnostic method showed that the thin cytoplasm of the adipocytes in this tissue were extensively infected with MAP. Abundant MAP was also seen in cells of the interstitial connective tissues within the fat. MAP was also seen to involve regional lymph nodes.

The gut tissues of all 5 people diagnosed with Irritable Bowel Syndrome (IBS) who were tested were also seen to be widely infected with MAP in a manner very similar to CD. Positive MAP staining of gut endoscopic biopsies was also seen in cases of Thyroditis and Psoriasis.

2. Animal Gut Tissues

Gut tissue samples were studied from 3 cows, 1 sheep, 1 goat, 1 red deer and 2 fallow deer all diagnosed with Johne's disease (JD). Autopsy samples were processed and stained with the primary antibodies, as described for humans. Tissues from all the animals were extensively infected with MAP which was generally present in the Ziehl-Neelsen positive phenotype. MAP in the guts of these animals diagnosed with Johne's disease stained with the A0X, A0XP, A4 and XA4P antibodies as well as with XA1. The microscopic appearance of MAP in animals was usually that of the classical Z-N positive mycobacterial phenotype but the monoclonal antibodies of the present work also demonstrated the pathogens in the paucimicrobial form.

The infective load of MAP in animals with Johne's disease was heavier than that found in humans in keeping with the well-recognised common pluribacillary form of JD. The MAP phenotype itself was consistent with ZN-positive cells. There was extensive involvement of mucosa and lamina propria and all layers of the gut. Cords of cells were seen which resulted from microvasculature full of MAP infected leucocytes. In addition, the thickened walls of vasculitic blood vessels and perivascular tissues were infiltrated with MAP infected cells as was seen in humans. MAP infection was also seen in neurovascular bundles affecting ganglion cells as well as nerve sheathes. This is consistent with the well described damage to the enteric nervous system of animals diagnosed with JD, much as in humans diagnosed with CD. A conspicuous difference between the gut tissues of these 5 ruminant species and humans is that A0XP is widely present in these animal gut tissues but appeared to be absent from human gut tissues.

3. Human Blood

Unlike in human gut tissues, A0XP, the phosphorylated form of A0X, is widely expressed in human blood. A0XP (MVINDDAQRLL[pS]QR) is the Serine phosphorylated form of A0X peptide in the extracellular amino terminal region of the IS900 protein. XA4P (YLSALVSIRTDPS[pS]R) is the A4 peptide in the extracellular carboxyterminal region of the IS900 protein with the distal of its two adjacent Serine residues phosphorylated. In CD both A0XP and XA4P are expressed within and on the surface of MAP-containing cells in human blood.

This provides 2 pairs of sterically accessible mutually exclusive antibodies on the P900 polypeptide for use in flow cytometry with A0X/A0XP on the amino terminal extracellular domain and A4/XA4P on the carboxy terminal extracellular domain. Each pair exists in a dynamic equilibrium as substrate and product, the sum of which provides a robust signal for determining the percentage of peripheral blood leucocyte populations infected with intra-cellular MAP. A0X/A0XP either remain attached to MAP or can be released within the cell and on the infected host cell's surface. A4/XA4P provide a similar signal but A4 can exit MAP infected cells and traffic between cells so that the cell populations containing A4/XA4P comprise those containing MAP organisms with an additional smaller population in which the A4/XA4P has been acquired by inter-cellular trafficking.

Flow cytometry on routine EDTA clinical blood samples was performed on 42 people with Crohn's disease using direct fluorophore labelled A0X-FITC/A0XP-PC5.5 and A4-FITC/XA4P-PC5.5 in an exploratory study. All people tested positive for MAP, with the proportion of the total circulating white blood cell population positive for MAP ranging from 3.9% to 47.1%. Use of phenotypic markers of the principal blood cell lineages enables a breakdown according to host cell type. These proportions were generally greater with A4/XA4P than they were with A0X/A0XP. The ratios A0X/A0XP and A4/XA4P provided a measure of phosphorylation activity. A high ratio of XA4P/A4 tended to characterise people with Crohn's disease in a higher state of activity. In such people intact monocytes in blood completely coated with segregated masses of A4/XA4P could be seen.

A second flow cytometry was carried out in 24 consecutive patients with Crohn's disease to determine the proportion (%) of total circulating white blood cells containing MAP.

Blood samples were collected into standard EDTA Vacutainer tubes. 1000 of blood was then added to the required number of 12×75 mm round bottomed Falcon tubes. These were incubated for 5 minutes with 50 Human Seroblock (Bio-Rad). Anti-human CD45 APC conjugated antibody (Beckman Coulter) was added to all tubes to enable gating on the leucocyte populations. Half of the tubes (labelled 'surface stained') were then treated with the anti-MAP monoclonal antibodies for 15 minutes at room temperature in the dark. 0.5 mls OptiLyse C (Beckman Coulter) red blood cell lysis buffer was then added to all these tubes and incubated for 10 minutes at room temperature in the dark.

The cells were then washed by adding 0.5 mls of PBS and centrifuged at 325 G for 5 minutes and the supernatant discarded.

All tubes were then fixed with 100 µl Fixation Medium A (Thermo Fisher Scientific) for 5 minutes then washed as above. The tubes that had not been stained with anti-MAP antibody (labelled 'Termeabilised') were incubated with Invitrogen Permeabilised Medium B (Thermo Fisher Scientific) to the pellet, anti-MAP monoclonal antibodies were added and incubated for 15 minutes at room temperature in the dark, followed by PBS washing as above. All tubes were then made up to 1 ml with flow buffer (PBS (Ca and Mg free), 0.2% sodium azide and 2% Bovine Serum Albumin (BSA). The samples were then acquired on a CytoFLEX flow cytometer (Beckman Coulter) gated on SSC vs CD45 and subsequently the data was an analysed using CytExpert software (Beckman Coulter).

The results of the second study in 24 people with Crohn's disease are shown in the table below (Table 2). There were 8 women and 16 men between the ages of 18 and 49 years. The numbers in the table along the rows indicate the % of the total circulating white blood cell population in each person stained by the corresponding MAP antibody A0X alone, A0XP alone or both A0X+A0XP as well as A4 alone, XA4P alone or both A4+XA4P. Because the A0 antibodies remain attached to their target peptides for longer than the A4 antibodies, the SUM of the A0 data in an individual person were taken as the measure of the % of circulating WBCs containing MAP (highlighted centre column). This SUM varies with the progress, clinical course and responses to treatment of Crohn's disease providing a direct access to the contribution to pathogenicity made by this unique multicopy insertion element.

The Flow Cytometry data from A4, XA4P and A4+XA4P provides a second direct insight into a probable contribution to pathogenicity of MAP by recording a further aspect of the in vivo function of P900. This is the ability to observe the phosphorylation and trafficking of the attached and released carboxy terminus both with the phosphorylation of the downstream serine as in the present work and that of the upstream partner and the presence and effect of dual phosphorylation.

Table 1 summarises the Flow Cytometry data obtained from 24 patients with Crohn's disease based on the use of the monoclonal antibodies A0X and A0XP on the extracellular amino-terminus of P900 on the left of the table and A4 and XA4P on the extracellular carboxy-terminus of P900 on the right. The data for each patient in each row separate into binding to the surface of white blood cells (surf) and binding to whole permeabilised cells (perm). The total proportion of cells infected by MAP is given by the sum of the percentages % in separate permeabilised cell populations identified by A0X alone, A0XP alone and A0X+A0XP (highlighted). This is the preferred measurement because A0X peptides tend to remain bound to the host intracellular mycobacterial cells longer than A4 peptides. On the right of the table are the results using A4, XA4P and A4+XA4P stained cell populations. In this study the strongly predicted phosphorylation of the distal serine in XA4P is used but similar studies may target the phosphorylated proximal serine of the pair or in dual phosphorylation.

The potential of the data comes together when we look at detail. The % total MAP loading across the group of 24 patients ranges from 1.52% to 48.9% and appears at the present stage to vary with the activity of the disease. Peaks or troughs in the % of MAP positive cells may follow the onset of anti-MAP treatments. More data will come as larger numbers of people are tested and with different diseases particularly in the "autoimmune and auto inflammatory" group, and with access to the loading of individual cell types. More data will also be obtained from studying the clinical correlates of phosphorylation events and monitoring the effects of different treatments.

The data show that the proportion of cells with A0X/A0XP or both on their surfaces is about half. In the permeabilised cells, the total cell percentage with A0X/A0XP is in close agreement with that using A4/XA4P, whereas the sum of A4/XA4P on the cell surface is considerably less than with A0X/A0XP. This would be consistent with a greater loss of A4/XA4P from the cell surface which is in keeping with its recognised greater mobility. Studies of the effect of these phosphorylation events will require larger clinical studies.

The flow cytometry system is the first example to be developed for paratuberculosis infection in Crohn's disease. This can now be used to study MAP infection in other diseases including especially psoriasis, thyroiditis, Parkinson's disease, type 1 diabetes, arthritis, ankylosing spondylitis, irritable bowel syndrome, ulcerative colitis, inflammatory bowel disease, Alzheimer's disease, multiple sclerosis, sarcoidosis, idiopathic pulmonary fibrosis and/or chronic fatigue syndrome. With Crohn's disease as with these other diseases, particularly "autoimmune conditions", whether or not the presence of MAP is contributing to disease causation or progression will come from whether or not specific anti-MAP therapy leads to remission or healing of the disease. At present, the therapeutic T-cell vaccine against MAP is in early clinical trials.

TABLE 2

| MAP Monoclonal | | | A0X | A0XP | A0X + A0XP | A0X/A0XP | A0X | A0XP | A0X + A0XP | A0X/A0XP |
|---|---|---|---|---|---|---|---|---|---|---|
| Patient | M/F | Age | surf | surf | surf | SUM | perm | perm | perm | SUM |
| 1 | F | 32 | 5.67 | 0.7 | 1.49 | 7.86 | 25.02 | 2.93 | 1.11 | 29.06 |
| 2 | M | 48 | 2.37 | 4.94 | 4.85 | 12.16 | 7.52 | 12.42 | 10.87 | 30.81 |
| 3 | M | 29 | 7.59 | 0.05 | 1.30 | 8.94 | 7.66 | 5.71 | 8.33 | 21.70 |
| 4 | M | 28 | 1.50 | 0.19 | 3.07 | 4.76 | 4.90 | 1.12 | 0.29 | 6.31 |
| 5 | M | 37 | 0.90 | 0.77 | 1.37 | 3.04 | 11.02 | 10.33 | 0.19 | 21.54 |
| 6 | F | 40 | 16.15 | 0.76 | 0.37 | 17.28 | 20.62 | 0.30 | 0.76 | 21.68 |
| 7 | F | 25 | 10.43 | 0.38 | 0.73 | 11.54 | 23.13 | 0.41 | 1.09 | 24.63 |
| 8 | M | 39 | 1.32 | 6.62 | 2.08 | 10.02 | 2.32 | 8.12 | 5.01 | 15.45 |
| 9 | M | 20 | 37.93 | 0.17 | 0.02 | 38.12 | 45.82 | 0.44 | 1.83 | 48.09 |
| 10 | M | 33 | 14.81 | 1.45 | 0.31 | 16.57 | 23.05 | 2.88 | 13.98 | 39.91 |
| 11 | F | 48 | 3.95 | 1.8 | 1.49 | 7.24 | 4.92 | 1.97 | 1.71 | 8.60 |
| 12 | F | 26 | 1.06 | 0.74 | 1.89 | 3.69 | 2.39 | 1.65 | 2.00 | 6.04 |
| 13 | M | 27 | 1.39 | 1.65 | 2.00 | 5.04 | 3.42 | 2.61 | 2.02 | 8.05 |
| 14 | M | 29 | 2.28 | 2.3 | 1.86 | 6.44 | 2.31 | 5.01 | 2.36 | 9.68 |
| 15 | M | 29 | 1.95 | 12.86 | 4.99 | 19.80 | 3.40 | 15.85 | 5.71 | 24.96 |
| 16 | M | 25 | 0.02 | 1.32 | 0.03 | 1.37 | 0.11 | 1.41 | 0.00 | 1.52 |
| 17 | M | 37 | 0.24 | 0.33 | 0.05 | 0.62 | 11.40 | 11.39 | 5.81 | 28.60 |
| 18 | M | 18 | 1.26 | 1.96 | 6.63 | 9.85 | 1.78 | 3.41 | 5.39 | 10.58 |
| 19 | F | 48 | 1.79 | 2.79 | 2.96 | 7.54 | 2.62 | 5.96 | 5.15 | 13.73 |
| 20 | F | 18 | 0.92 | 5.15 | 0.64 | 6.71 | 1.22 | 5.67 | 1.20 | 8.09 |
| 21 | M | 20 | 11.78 | 0.36 | 8.85 | 20.99 | 15.41 | 0.30 | 9.28 | 24.99 |
| 22 | M | 49 | 0.35 | 1.27 | 0.80 | 2.42 | 1.58 | 1.97 | 2.76 | 6.31 |
| 23 | M | 19 | 0.77 | 0.68 | 3.83 | 5.28 | 1.76 | 1.72 | 4.01 | 7.49 |
| 24 | F | 48 | 0.05 | 4.09 | 0.02 | 4.16 | 0.94 | 6.83 | 0.21 | 7.98 |
| SUM | | | | | | 231.44 | | | | 425.80 |
| average | | | | | | 9.64 | | | | 17.74 |

| MAP Monoclonal | | | A4 | XA4P | A4 + XA4P | A4/XA4P | A4 | XA4P | A4 + XA4P | A4/XA4P |
|---|---|---|---|---|---|---|---|---|---|---|
| Patient | M/F | Age | surf | surf | surf | SUM | perm | perm | perm | SUM |
| 1 | F | 32 | 3.14 | 6.63 | 5.98 | 15.75 | 3.91 | 19.76 | 6.88 | 30.55 |
| 2 | M | 48 | 5.47 | 1.19 | 0.13 | 6.79 | 7.54 | 1.27 | 2.29 | 11.10 |
| 3 | M | 29 | 3.09 | 3.70 | 1.44 | 8.23 | 9.05 | 4.23 | 2.82 | 16.10 |
| 4 | M | 28 | 3.54 | 1.00 | 0.34 | 4.88 | 5.85 | 0.23 | 1.25 | 7.33 |
| 5 | M | 37 | 0.31 | 1.42 | 0.90 | 2.63 | 6.85 | 19.24 | 2.94 | 29.03 |
| 6 | F | 40 | 1.20 | 0.14 | 0.21 | 1.55 | 1.25 | 2.77 | 1.88 | 5.90 |
| 7 | F | 25 | 2.59 | 0.14 | 0.50 | 3.23 | 2.89 | 12.09 | 31.62 | 46.60 |
| 8 | M | 39 | 8.35 | 8.73 | 6.09 | 23.17 | 11.92 | 10.83 | 12.83 | 35.58 |
| 9 | M | 20 | 0.41 | 0.00 | 0.12 | 2.50 | 19.89 | 5.76 | 3.01 | 28.66 |
| 10 | M | 33 | 21.26 | 0.03 | 1.23 | 22.52 | 7.90 | 0.84 | 41.03 | 49.77 |
| 11 | F | 48 | 2.20 | 0.02 | 0.28 | 2.50 | 2.35 | 4.17 | 1.72 | 8.24 |
| 12 | F | 26 | 0.45 | 0.15 | 0.10 | 0.70 | 2.77 | 0.96 | 0.81 | 4.54 |
| 13 | M | 27 | 2.17 | 0.96 | 0.81 | 3.94 | 3.04 | 1.46 | 1.35 | 5.85 |
| 14 | M | 29 | 0.30 | 6.31 | 2.50 | 9.11 | 2.33 | 11.74 | 7.91 | 21.98 |
| 15 | M | 29 | 0.00 | 0.56 | 2.45 | 3.01 | 0.00 | 6.98 | 8.26 | 15.24 |
| 16 | M | 25 | 0.68 | 0.64 | 0.46 | 1.78 | 1.38 | 1.37 | 0.47 | 3.22 |
| 17 | M | 37 | 0.05 | 2.24 | 0.14 | 2.43 | 2.27 | 4.31 | 1.09 | 7.67 |
| 18 | M | 18 | 0.36 | 9.11 | 1.53 | 11.00 | 0.42 | 13.6 | 1.76 | 15.78 |
| 19 | F | 48 | 1.04 | 3.40 | 3.60 | 8.04 | 2.43 | 4.88 | 8.14 | 15.45 |
| 20 | F | 18 | 5.12 | 0.53 | 2.61 | 8.26 | 5.62 | 0.85 | 5.61 | 12.08 |
| 21 | M | 20 | 0.85 | 2.70 | 0.36 | 3.91 | 19.92 | 4.1 | 6.84 | 30.86 |
| 22 | M | 49 | 8.80 | 0.31 | 7.08 | 16.19 | 9.06 | 0.58 | 9.12 | 18.76 |
| 23 | M | 19 | 0.38 | 0.21 | 0.21 | 0.80 | 2.06 | 0.76 | 0.41 | 3.23 |

TABLE 2-continued

| 24 | F | 48 | 0.00 | 6.76 | 4.62 | 11.38 | 0.49 | 7.81 | 4.91 | 13.21 |
|---|---|---|---|---|---|---|---|---|---|---|
| SUM | | | | | | 174.30 | | | | 436.73 |
| average | | | | | | 7.26 | | | | 18.20 |

3.2 Cytology

Cells isolated from peripheral blood were stained with a combination of two directly conjugated monoclonal antibodies: A0X (FITC/Green)+A0XP (Cy 5.5/Red) or A4 FITC/Green)+XA4P (Cy 5.5/Red). Confocal images were viewed using a Leica SP-2 confocal microscope, recorded and stored in JPEG format.

Results: peripheral blood cells showed considerable heterogeneity in their staining pattern with cells either negative, positive for a single antibody only, or positive for both antibodies. This latter observation is demonstrated by the clear co-localisation of the fluorescent reporter molecules. Although the phenotype of positive cells is yet to be established DIC (differential interference contrast) imaging and Flow cytometry data indicate that positive cells are non-lymphocytic in origin.

4. Animal Blood 4.1 Cats

A domestic cat (Cat 1) became unwell with weight loss, diarrhoea, distended abdomen and poor general condition. Ultrasound scan of the abdomen of the clinically affected animal showed thickening of the wall throughout the colon. Endoscopy and biopsy by the veterinarian showed clinically and histologically that the animal had Inflammatory Bowel Disease. Flow cytometry was performed on 2 EDTA blood samples over a period of 4 months. The proportion of total circulating white blood cells infected with MAP in the cat was 7.6% and 9.8%. Immunofluorescence microscopy on the endoscopic biopsy samples from Cat 1 confirmed the presence of MAP with a histological appearance similar to that seen in both animals with Johne's disease and humans with Crohn's disease.

During this period, a new kitten (Cat 2) was introduced to the same household. It was clinically well at the time of purchase from the breeder. A week following introduction to the household, the kitten developed bloody diarrhoea. Routine stool microbiology was negative. Flow cytometry was again performed on 2 EDTA blood samples over a period of 4 months. The proportion of circulating white cells infected with MAP was 16.4% and 14.3%. These data confirmed that both animals had a systemic MAP infection.

4.2 Dairy Cows

EDTA blood samples were obtained from 4 dairy cows. These animals were part of a closed dairy herd of more than 20 years standing with no known clinical cases of Johne's disease. Intermittent ELISA testing of individual milk samples from the herd had shown that one of the 4 sampled cows had had 2 positive ELISA readings and 2 other sampled cows had had 1 positive ELISA reading amongst multiple negative results. The fourth cow had had no raised ELISA readings on milk at all. Flow cytometry was performed on the 4 blood samples using A0X/A0XP and A4/XA4P pairs of monoclonal antibodies. The results showed that the proportions of the total circulating white blood cell populations in these animals infected with intracellular MAP, were 10.9%, 36.3%, 40.1%, and 45.2%. These results are a further indication of the ability of a significant systemic MAP infection to persist in a subclinical state. They also demonstrate that the present diagnostic technology has a much greater sensitivity than conventional diagnostic methods with the ability to reveal the true scale of the long term threat to animal and human health posed by these pathogens.

5. Human Breast Milk

A 3 month old male child presented with rectal bleeding and episodes of abdominal pain. He was investigated including upper and lower Gastrointestinal endoscopy with multiple biopsies, which led to the establishment of a diagnosis of Crohn's disease at 8 months. MAP tests, subsequently requested and carried out on his paraffin embedded histopathology blocks showed extensive infection with MAP of the stomach and duodenum and in all biopsies from the terminal ileum to the rectum. His mother, who did not have Crohn's disease, had never fed him anything except her own milk. However she had been diagnosed with auto-immune thyroiditis which is linked genetically to Crohn's disease. MAP testing requested by her on a 50 ml sample of expressed breast milk showed abundant MAP infected cells in the centrifugal pellet.

6. Human Skin Samples in Psoriasis 3-4 mm punch biopsy full thickness skin samples were obtained under local anaesthesia from 2 adults each diagnosed with Psoriasis. Samples were taken from the central region of a psoriatic skin lesion and an additional sample from the periphery of the lesion overlapping with normal skin. A normal skin sample between lesions was also obtained. Samples were formalin fixed, processed and embedded in routine histopathology blocks, following standard procedures. Sections of 2 μm were cut, immobilised on Vectabond microscope slides, treated for antigen retrieval, and stained with XA1/A4 monoclonal antibodies and examined by confocal microscopy.

Biopsies taken from within the psoriatic lesions were positive for MAP in both adults. Gold colocalisation of XA1 and A4 was seen in inflammatory cells in the thickened epidermal layer with staining persisting into the stratum corneum. Staining was also conspicuous in the germinal layer. Positive MAP staining extended throughout inflammatory cells in the rete and in inflammatory cells within the dermis. MAP positive cells were also seen around the hair follicles. A conspicuous associated feature was the presence of MAP within the pilo-sebaceous unit.

An abnormality of sebaceous glands might contribute to the dry, scaly nature of the superficial layers of psoriatic plaques. A further conspicuous feature in the dermis was MAP involvement of neurovascular bundles with colocalising XA1/A4 staining of these pathogens within thickened arterial walls and perivascular connective tissues. MAP staining of adjacent nerve bundles was also seen. Staining from biopsies taken at the periphery of psoriatic plaques showed that MAP staining stopped at the boundary between the plaque and normal skin. MAP was also absent from biopsies of normal looking skin between plaques. This would be consistent with a role for MAP in psoriatic plaque formation.

7. Measuring the Proportion of MAP Positive Cells in Synovial Joint Fluid in Arthritis An adult female human with Psoriasis presented with discomfort and an acute effusion in her right knee joint. There was no history of trauma. The joint was warm and distended but was not acutely tender. Other joints were unaffected. A 20 ml sample of straw coloured slightly opalescent fluid was aspirated and the cells separated by centrifugation. These were washed, stained with fluorophore labelled A0X/A0XP and examined by flow cytometry. The proportion of cells containing MAP in the joint fluid was 8.56%. This was similar to the % of MAP-positive peripheral white blood cells in her blood at the time.

Example 4: Construction of New ChAdOx2 Vaccines

Based on the above results, the hAd5 HAV vaccine described in Example 1 has been developed to include additional MAP peptides at the amino terminus. Two new vaccines have been produced: HAVX1 and HAVX2. HAVX1 and HAVX2 are five gene vaccines, whilst HAV (Bull et al. 2007 PLoS ONE 2(11): e1229; Bull et al. 2014 Veterinary Research 45:112; Example 1 above) is a four gene vaccine. HAVX1 encodes the sequence:

MTVTEVVVAQPVWAGVDAGKADHYCMVINDDAQRLLSQRVANDEAALL

ELIAAVTTLADGGEVTWAIDLNAGGAALLIALLIAAGQRLLYIPGATV

HHAAGSYRGE followed by the 2A sequence (APVKQTLNFDLLKLAGDVESNPGP)

followed by HAV.

(SEQ ID NO: 41)

The HAVX1 represents the normal extra-mycobacterial region, the transmembrane region and the first intra-mycobacterial portion of the P900 sequence stopping short of the active site mechanism of the putative transposase. It has no known toxicity and is abundantly expressed in vivo.

HAVX2 encodes the sequence:

MVINDDAQRLLSQRVDAGKADHYAVTTLADGGEVTWAIDLNAGGAALL

IALLIAAGQRLLYIPGATVHHAAGSYRGE followed by the 2A sequence (APVKQTLNFDLLKLAGDVESNPGP)

followed by HAV.

(SEQ ID NO: 41)

The HAVX2 disrupts the normal sequence, places emphasis on the N-terminal epitope and exposes a further T-cell epitope just before it dips into the transmembrane sequence.

These rearrangements are not predicted to introduce any risk and are compatible with the safe handling of new ChAdOx2 HAVX1 and ChAdOx2 HAVX2 vaccine constructs.

The invention claimed is:

1. A *Mycobacterium avium* subspecies *paratuberculosis* (MAP) vaccine comprising a polypeptide comprising a fragment of MAP P900 of up to 150 amino acids in length comprising an amino acid sequence of at least 9 contiguous amino acids from the region of MAP P900 shown in SEQ ID NO: 2.

2. The MAP vaccine of claim 1, wherein the polypeptide comprises the amino acid sequence MVINDDAQRLLSQR (SEQ ID NO: 3).

3. The MAP vaccine of claim 2, wherein the polypeptide comprises the amino acid sequence MVINDDAQRLL[PS]QR (SEQ ID NO: 5), wherein [pS] is phosphorylated serine.

4. The MAP vaccine of claim 1, which comprises two or more polypeptides comprising an amino acid sequence of at least 9 contiguous amino acids from the region of MAP P900 shown in SEQ ID NO: 2.

5. The MAP vaccine of claim 4, which comprises a polypeptide comprising the amino acid sequence MVINDDAQRLLSQR (SEQ ID NO: 3) and a polypeptide comprising the amino acid sequence MVINDDAQRLL[PS]QR (SEQ ID NO: 5), wherein [pS] is phosphorylated serine.

6. The MAP vaccine of claim 4, which comprises at least two of the following polypeptides: a polypeptide comprising the amino acid sequence MVINDDAQRLLSQR (SEQ ID NO: 3), a polypeptide comprising the amino acid sequence VTTLADGGEVTWAID (SEQ ID NO:7), and a polypeptide comprising the amino acid sequence EVVVAQPVWAGVDAGKADHY (SEQ ID NO: 9).

7. The MAP vaccine of claim 1, wherein the polypeptide further comprises the amino acid sequence of at least one additional MAP polypeptide, or a fragment thereof.

8. The MAP vaccine of claim 1, further comprising a polypeptide comprising an amino acid sequence of at least one additional MAP polypeptide, or a fragment thereof.

9. A polypeptide which comprises the amino acid sequence MVINDDAQRLLSQR (SEQ ID NO: 3) and an ahpC polypeptide, a gsd polypeptide, a p12 polypeptide and/or a mpa polypeptide, wherein:
   (a) said ahpC polypeptide has the amino acid sequence given in SEQ ID NO: 32;
   (b) said gsd polypeptide has the amino acid sequence given in SEQ ID NO: 34;
   (c) said p12 polypeptide has the amino acid sequence given in SEQ ID NO: 36; and/or
   (d) said mpa polypeptide has the amino acid sequence given in SEQ ID NO: 40.

10. The polypeptide of claim 9, which comprises the amino acid sequence MVINDDAQRLL[PS]QR (SEQ ID NO: 5), wherein [pS] is phosphorylated serine.

11. A kit for treating or preventing MAP infection or a condition or symptom associated with MAP infection, said kit comprising (i) at least one of a polypeptide comprising an amino acid sequence of at least 9 contiguous amino acids from the region of MAP P900 shown in SEQ ID NO: 2 and (ii) at least one other therapeutic agent, for simultaneous, sequential or separate use.

* * * * *